US011759437B2

(12) United States Patent
Cheah et al.

(10) Patent No.: US 11,759,437 B2
(45) Date of Patent: Sep. 19, 2023

(54) PREVENTIVE AND THERAPEUTIC APPROACH FOR ABERRANT CELL DIFFERENTIATION AND ISR-ASSOCIATED DISEASES

(71) Applicant: The University of Hong Kong, Hong Kong (CN)

(72) Inventors: Song Eng Kathryn Cheah, Hong Kong (CN); Danny Chan, Hong Kong (CN); Cheng Wang, Hong Kong (CN); Cheuk Wing Wilson Chan, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 161 days.

(21) Appl. No.: 16/335,395

(22) PCT Filed: Sep. 22, 2017

(86) PCT No.: PCT/IB2017/055783
§ 371 (c)(1),
(2) Date: Mar. 21, 2019

(87) PCT Pub. No.: WO2018/055578
PCT Pub. Date: Mar. 29, 2018

(65) Prior Publication Data
US 2019/0240171 A1  Aug. 8, 2019

Related U.S. Application Data

(60) Provisional application No. 62/398,514, filed on Sep. 22, 2016.

(51) Int. Cl.
| | |
|---|---|
| *A61K 31/136* | (2006.01) |
| *A61K 31/165* | (2006.01) |
| *A61P 19/08* | (2006.01) |
| *C07C 235/14* | (2006.01) |
| *C07C 211/29* | (2006.01) |
| *C07C 235/20* | (2006.01) |
| *A61P 19/00* | (2006.01) |
| *A61K 31/519* | (2006.01) |
| *A61P 3/08* | (2006.01) |
| *A61P 35/00* | (2006.01) |
| *A61P 29/00* | (2006.01) |
| *A61K 31/47* | (2006.01) |
| *A61K 31/4965* | (2006.01) |

(52) U.S. Cl.
CPC .......... *A61K 31/136* (2013.01); *A61K 31/165* (2013.01); *A61K 31/47* (2013.01); *A61K 31/4965* (2013.01); *A61K 31/519* (2013.01); *A61P 3/08* (2018.01); *A61P 19/00* (2018.01); *A61P 19/08* (2018.01); *A61P 29/00* (2018.01); *A61P 35/00* (2018.01); *C07C 211/29* (2013.01); *C07C 235/14* (2013.01); *C07C 235/20* (2013.01)

(58) Field of Classification Search
CPC ... C07C 211/29; C07C 235/20; C07C 235/14; A61K 31/165; A61K 31/47; A61K 31/4965; A61K 31/519; A61K 31/136; A61P 19/00; A61P 19/08
See application file for complete search history.

(56) References Cited

FOREIGN PATENT DOCUMENTS

| | | |
|---|---|---|
| CN | 102917588 A | 2/2013 |
| WO | WO 2011/119663 A1 * | 9/2011 |
| WO | WO 2014144952 A2 | 9/2014 |
| WO | WO 2015120350 A2 | 8/2015 |
| WO | WO 2016025635 A2 | 2/2016 |

OTHER PUBLICATIONS

Patterson, "Mechanisms and Models of Endoplasmic Reticulum Stress in Chondrodysplasia", Developmental Dynamics 243: 875-893. (Year: 2014).*
Atkins, "Characterization of a Novel PERK Kinase Inhibitor with Antitumor and Antiangiogenic Activity", Cancer Res; 73(6); 1993-2002. (Year: 2013).*
Sidrauski, "The small molecule ISRIB reverses the effects of eIF2α phosphorylation on translation and stress granule assembly", eLife, 4, e05033/1-e05033/16 (Year: 2015).*
Akiyama et al.; Genes Dev. Nov. 1, 2002;16(21):2813-28.
An et al.; Intervertebral disc degeneration: biological and biomechanical factors; J Orthop Sci. Oct. 2006;11(5):541-52.
Ashburner et al.; Gene ontology: tool for the unification of biology. The Gene Ontology Consortium; Nat Genet. May 2000;25(1):25-9.
Balwierz et al.; ISMARA: automated modeling of genomic signals as a democracy of regulatory motifs; Genome Res. May 2014;24(5):869-84.

(Continued)

*Primary Examiner* — Sahar Javanmard
(74) *Attorney, Agent, or Firm* — Law Offices of Albert Wai-Kit Chan, PLLC

(57) ABSTRACT

The present invention describes a method of preventing, ameliorating and/or treating disorders or diseases associated with the integrated stress response (ISR) involving the p-eIF2α pathway arising from various cellular stresses such as oxidative stress, hypoxia and ER stress, chronic or prolonged bio-mechanical stress. In one embodiment, the present invention provides a method which prevents or alleviates aberrant cell differentiation that is caused by the activation of the integrated stress response and thereby prevents or alleviates conditions, disorders or diseases resulting therefrom. In one embodiment, ISR-associated diseases subject to the present invention include but are not limited to skeletal disorders including disc degeneration, MCDS and other skeletal dysplasias, cancers, inflammatory diseases, diabetes, fibrosis, obesity and neurodegenerative diseases. In another embodiment, the present invention provides a method of using a p-eIF2α-modulator for the prevention or treatment of conditions, disorders or diseases described herein.

7 Claims, 71 Drawing Sheets
Specification includes a Sequence Listing.

(56) References Cited

OTHER PUBLICATIONS

Bateman et al.;Genetic diseases of connective tissues: cellular and extracellular effects of ECM mutations; Nat Rev Genet. Mar. 2009;10(3):173-83.
Bell et al.; SOX9 directly regulates the type-II collagen gene; Nat Genet. Jun. 1997;16(2):174-8.
Briggs et al.; Hum Mutat. May 2002;19(5):465-78.
Brostrom et al.; J Biol Chem. Oct. 4, 1996;271(40):24995-5002.
Buenrostro et al.; ATAC-seq: A Method for Assaying Chromatin Accessibility Genome-Wide; Curr Protoc Mol Biol. Jan. 5, 2015;109:21.29.1-9.
Cameron et al.; PLoS One. 2011 ;6(9):e24600.
Cameron et al.; XBP1-Independent UPR Pathways Suppress C/EBP-β Mediated Chondrocyte Differentiation in ER-Stress Related Skeletal Disease; PLoS Genet. Sep. 15, 2015;11(9):e10055.
Campbell et al.;Genome wide gene expression analysis of the posterior capsule in patients with osteoarthritis and knee flexion contracture; J Rheumatol. Nov. 2014;41(11):2232-9.
Cheresh et al.; Oxidative stress and pulmonary fibrosis; Biochim Biophys Acta. Jul. 2013; 1832(7):1028-40.
Cong et al.; Multiplex Genome Engineering Using CRISPR/Cas Systems; Science. Feb. 15, 2013;339(6121):819-23.
Cucoranu et al.; Circ Res. Oct. 28, 2005;97(9):900-7.
Cuddapah et al.; Genome Res. Jan. 2009;19(1):24-32.
De Sousa-Coelho et al.; Activating transcription factor 4-dependent induction of FGF21 during amino acid deprivation; Biochem J. Apr. 1, 2012;443(1):165-71.
Dennis et al.; DAVID: Database for Annotation, Visualization, and Integrated Discovery; Genome Biol. 2003;4(5):P3. Epub Apr. 3, 2003.
Denoyelle et al.; Nat Cell Biol. Oct. 2006;8(10):1053-63.
Dever et al.;Cell. Feb. 7, 1992;68(3):585-96.
Di Prisco et al.; Translational control of mGluR-dependent long-term depression and object-place learning by eIF2α; Nat Neurosci. Aug. 2014;17(8):1073-82.
Dy et al.; Sox9 directs hypertrophic maturation and blocks osteoblast differentiation of growth plate chondrocytes; Dev Cell. Mar. 13, 2012;22(3):597-609.
García et al.;The dsRNA protein kinase PKR: virus and cell control; Biochimie. Jun.-Jul. 2007;89(6-7):799-811. Epub Mar. 12, 2007.
Ghosh et al.; PAI-1 in tissue fibrosis; J Cell Physiol. Feb. 2012;227(2):493-507. doi: 10.1002/jcp.22783.
Hadjipavlou et al.; The pathophysiology of disc degeneration: a critical review; J Bone Joint Surg Br. Oct. 2008;90(10):1261-70.
Han et al.; ER-stress-induced transcriptional regulation increases protein synthesis leading to cell death; Nat Cell Biol. May 2013;15(5):481-90.
Han et al.;EMBO J. Dec. 3, 2001;20(23):6909-18.
Harding et al.; An integrated stress response regulates amino acid metabolism and resistance to oxidative stress; Mol Cell. Mar. 2003;11(3):619-33.
Harding et al.; Protein translation and folding are coupled by an endoplasmic-reticulum-resident kinase; Nature. Jan. 21, 1999;397(6716):271-4.
Harding et al.; Regulated translation initiation controls stress-induced gene expression in mammalian cells; Mol Cell. Nov. 2000;6(5):1099-108.
Hart et al.;ER stress-mediated autophagy promotes Myc-dependent transformation and tumor growth; J Clin Invest. Dec. 2012;122(12):4621-34.
Heinz et al.; Mol Cell. May 28, 2010;38(4):576-89.
Hetz et al.; Targeting the unfolded protein response in disease; Nat Rev Drug Discov. 2013; 12: 703-719.
Hiyama et al.; Hypoxia activates the notch signaling pathway in cells of the intervertebral disc: implications in degenerative disc disease; Arthritis Rheum. May 2011;63(5).
Ho et al.; Fibrosis—a lethal component of systemic sclerosis; Nat Rev Rheumatol. Jul. 2014;10(7):390-402.

Horiuchi et al.; The unfolded protein response in skeletal development and homeostasis; Cell Mol Life Sci. Aug. 2016;73(15):2851-69.
Hotta et al.; Endocrinology. Oct. 2009;150(10):4625-33.
Ionescu et al.; FoxA family members are crucial regulators of the hypertrophic chondrocyte differentiation program; Dev Cell. May 15, 2012;22(5):927-39.
Jain et al.; Data clustering: 50 years beyond K-means; Pattern Recognition Letters. 2010; 31(8): 651-666.
Jo et al.;The versatile functions of Sox9 in development, stem cells, and human diseases; Genes Dis. Dec. 2014;1(2):149-161.
Jousse et al.; Inhibition of a constitutive translation initiation factor 2alpha phosphatase, CReP, promotes survival of stressed cells; J Cell Biol. Nov. 24, 2003;163(4):767-75.
Kanazawa et al.; Efficacy of growth hormone therapy for patients with skeletal dysplasia; J Bone Miner Metab. 2003;21(5):307-10.
Kang et al.;Sox9-Positive Progenitor Cells Play a Key Role in Renal Tubule Epithelial Regeneration in Mice; Cell Rep. Feb. 2, 2016;14(4):861-871.
Kearns et al.; Functional annotation of native enhancers with a Cas9-histone demethylase fusion; Nat Methods. May 2015;12(5):401-403.
Kharitonenkov et al.; FGF-21 as a novel metabolic regulator; J Clin Invest. Jun. 2005;115(6):1627-35.
Kim et al.; FGF21 as a mediator of adaptive responses to stress and metabolic benefits of anti-diabetic drugs; J Endocrinol. Jul. 2015;226(1):R1-16.
Kim et al.; Autophagy deficiency leads to protection from obesity and insulin resistance by inducing Fgf21 as a mitokine; Nat Med. Jan. 2013;19(1):83-92.
Kim et al.; The Role of Oxidative Stress in Neurodegenerative Diseases; Exp Neurobiol. Dec. 2015;24(4):325-40.
Koziel et al.; Gli3 acts as a repressor downstream of Ihh in regulating two distinct steps of chondrocyte differentiation; Development. Dec. 2005;132(23):5249-60.
Langmead et al.; Ultrafast and memory-efficient alignment of short DNA sequences to the human genome; Genome Biol. 2009;10(3):R25.
Leung et al.; Matrix remodeling during intervertebral disc growth and degeneration detected by multichromatic FAST staining; J Histochem Cytochem. Mar. 2009;57(3):249-56.
Leung et al.; PLoS Genet. Nov. 2011;7(11):e1002356.
Lie et al.; Limb lengthening in short-stature patients using monolateral and circular external fixators; Hong Kong Med J. Aug. 2009; 15(4):280-4.
Lindholm et al.; ER stress and neurodegenerative diseases; Cell Death Differ. Mar. 2006;13(3):385-92.
Lisse et al.; ER stress-mediated apoptosis in a new mouse model of osteogenesis imperfecta; PLoS Genet. Feb. 2008;4(2):e7.
Liu et al.; Oxidative stress and glutathione in TGF-beta-mediated fibrogenesis; Free Radic Biol Med. Jan. 1, 2010;48(1):1-15.
Lu et al.; Opposing unfolded-protein-response signals converge on death receptor 5 to control apoptosis; Science. Jul. 4, 2014;345(6192):98-101.
Lupiáñez et al.; Disruptions of topological chromatin domains cause pathogenic rewiring of gene-enhancer interactions; Cell. May 21, 2015;161(5):1012-1025.
Madisen et al.; Transgenic mice for intersectional targeting of neural sensors and effectors with high specificity and performance; Neuron. Mar. 4, 2015;85(5):942-58.
Marciniak et al.; CHOP induces death by promoting protein synthesis and oxidation in the stressed endoplasmic reticulum; Genes Dev. Dec. 15, 2004;18(24):3066-77.
Moreno et al.; Sustained translational repression by eIF2α-P mediates prion neurodegeneration; Nature. May 6, 2012;485(7399):507-11.
Mäkitie et al.; Schmid type of metaphyseal chondrodysplasia and COL10A1 mutations—findings in 10 patients; Am J Med Genet A. Sep. 1, 2005;137A(3):241-8.
Nel-Themaat et al.; Morphometric analysis of testis cord formation in Sox9-EGFP mice; Dev Dyn. May 2009;238(5):1100-10.
Ng et al.; SOX9 binds DNA, activates transcription, and coexpresses with type II collagen during chondrogenesis in the mouse; Dev Biol. Mar. 1, 1997;183(1):108-21.
Nundlall et al.; Cell Stress Chaperones. Nov. 2010;15(6):835-49.

(56) References Cited

OTHER PUBLICATIONS

Olsen; Mutations in collagen genes resulting in metaphyseal and epiphyseal dysplasias; Bone. Aug. 1995;17(2 Suppl):45S-49S.

Oslowski et al.; Measuring ER stress and the unfolded protein response using mammalian tissue culture system; Methods Enzymol. 2011;490:71-92.

Palam et al.; Integrated stress response is critical for gemcitabine resistance in pancreatic ductal adenocarcinoma; Cell Death Dis. Oct. 15, 2015;6:e1913.

Palii et al.; Biochem J. May 1, 2006;395(3):517-27.

Patterson et al.; Mechanisms and models of endoplasmic reticulum stress in chondrodysplasia; Dev Dyn. Jul. 2014;243(7):875-93.

Pennuto et al.; Ablation of the UPR-mediator CHOP restores motor function and reduces demyelination in Charcot-Marie-Tooth 1B mice; Neuron. Feb. 7, 2008;57(3):393-405.

Piróg et al.; Mild myopathy is associated with COMP but not MATN3 mutations in mouse models of genetic skeletal diseases; PLoS One. Nov. 27, 2013;8(11):e82412.

Piróg et al.; Abnormal Chondrocyte Apoptosis in the Cartilage Growth Plate is Influenced by Genetic Background and Deletion of CHOP in a Targeted Mouse Model of Pseudoachondroplasia PLoS On Feb. 18, 2014;9(2):e85145.

Posey et al.; Chondrocyte-Specific Pathology During Skeletal Growth and Therapeutics in a Murine Model of Pseudoachondroplasia; J Bone Miner Res. May 2014; 29(5): 1258-1268.

Posey et al.; Chop (Ddit3) Is Essential for D469del-COMP Retention and Cell Death in Chondrocytes in an Inducible Transgenic Mouse Model of Pseudoachondroplasia. Am J Pathol. Feb. 2012;180(2):727-37.

Pritchett et al.;Osteopontin is a novel downstream target of SOX9 with diagnostic implications for progression of liver fibrosis in humans; Hepatology. Sep. 2012;56(3):1108-16.

Pritchett et al.;Understanding the role of SOX9 in acquired diseases: lessons from development; Trends Mol Med. Mar. 2011;17(3):166-74.

Provost et al.; Viral 2A peptides allow expression of multiple proteins from a single ORF in transgenic zebrafish embryos; Genesis. Oct. 2007;45(10):625-9.

Quackenbush et al.; Computational analysis of microarray data; Nat Rev Genet. Jun. 2001;2(6):418-27.

Ridanpää et al.; Genetic changes in the RNA components of RNase MRP and RNase P in Schmid metaphyseal chondrodysplasia; J Med Genet. Oct. 2003;40(10):741-6.

Ron et al.;Translational control in the endoplasmic reticulum stress response; J Clin Invest. Nov. 2002;110(10):1383-8.

Rutkowski et al.; Regulation of basal cellular physiology by the homeostatic unfolded protein response; J Cell Biol. May 31, 2010;189(5):783-94.

Ryan et al.; HIF-1 alpha is required for solid tumor formation and embryonic vascularization; Embo J. Jun. 1, 1998;17(11):3005-15.

Rzymski et al.;Regulation of autophagy by ATF4 in response to severe hypoxia; Oncogene. Aug. 5, 2010;29(31):4424-35.

Savarirayan et al.; Schmid type metaphyseal chondrodysplasia: a spondylometaphyseal dysplasia identical to the "Japanese" type;Pediatr Radiol. Jul. 2000;30(7):460-3.

Schipani et al.; Hypoxia in cartilage: HIF-1alpha is essential for chondrocyte growth arrest and survival; Genes Dev. Nov. 1, 2001;15(21):2865-76.

Sekine et al.; Stress responses. Mutations in a translation initiation factor identify the target of a memory-enhancing compound; Science. May 29, 2015;348(6238):1027-30.

Sidrauski et al.; Pharmacological brake-release of mRNA translation enhances cognitive memory; Elife. May 28, 2013;2:e00498.

Sidrauski et al.; Pharmacological dimerization and activation of the exchange factor eIF2B antagonizes the integrated stress response; Elife. Apr. 15, 2015;4:e07314.

Siegel et al.; Psychological impact of significantly short stature; Acta paediatrica Scandinavica. 1991; Supplement 377: 14-18.

Smith et al.; Degeneration and regeneration of the intervertebral disc: lessons from development; Dis Model Mech. Jan. 2011;4(1):31-41.

Southwood et al.; The unfolded protein response modulates disease severity in Pelizaeus-Merzbacher disease; Neuron. Nov. 14, 2002;36(4):585-96.

Stricker et al.; Role of Runx genes in chondrocyte differentiation; Dev Biol. May 1, 2002;245(1):95-108.

Sudhakar et al.; Biochemistry. Oct. 24, 2000;39(42):12929-38.

Suleman et al.; A novel form of chondrocyte stress is triggered by a COMP mutation causing pseudoachondroplasia; Hum Mutat. Jan. 2012;33(1):218-31.

Suzuki et al.; Excessive reactive oxygen species are therapeutic targets for intervertebral disc degeneration; Arthritis Res Then Nov. 5, 2015;17:316.

Symmons et al.; Functional and topological characteristics of mammalian regulatory domains; Genome Res. Mar. 2014;24(3):390-400.

Thompson et al.; Medical and social aspects of the life course for adults with a skeletal dysplasia: a review of current knowledge; Disabil Rehabil. 2008; 30(1):1-12.

Tsang et al.; In vivo cellular adaptation to ER stress: survival strategies with double-edged consequences ;J Cell Sci. Jul. 1, 2010;123(Pt 13):2145-54.

Tsang et al.; Surviving endoplasmic reticulum stress is coupled to altered chondrocyte differentiation and function; PLoS Biol. Mar. 2007;5(3):e44.

Urban et al.;Degeneration of the intervertebral disc; Arthritis Res Ther. 2003;5(3):120-30. Epub Mar. 11, 2003.

Wai et al.; Disrupted expression of matrix genes in the growth plate of the mouse cartilage matrix deficiency (cmd) mutant; Dev Genet. 1998;22(4):349-58.

Walter et al.; The unfolded protein response: from stress pathway to homeostatic regulation; Science. Nov. 25, 2011;334(6059):1081-6.

Wang et al.; Apoptosis. Oct. 2011;16(10):990-1003.

Wang et al.; Development. Dec. 1, 2005; 136(24): 4143-4153.

Wek et al.;Coping with stress: eIF2 kinases and translational control; Biochem Soc Trans. Feb. 2006;34(Pt 1):7-11.

Wingender et al.; TRANSFAC: a database on transcription factors and their DNA binding sites; Nucleic Acids Res. Jan. 1, 1996;24(1):238-41.

Wynn et al.;Cellular and molecular mechanisms of fibrosis; J Pathol. Jan. 2008;214(2):199-210.

Yang et al.; Hypertrophic chondrocytes can become osteoblasts and osteocytes in endochondral bone formation; Proc Natl Acad Sci U S A. Aug. 1, 2014;111(33):12097-102.

Ye et al.;The GCN2-ATF4 pathway is critical for tumour cell survival and proliferation in response to nutrient deprivation; Embo J. Jun. 16, 2010;29(12):2082-96.

Zeng et al.; An inducible and reversible mouse genetic rescue system; PLoS Genet. May 9, 2008;4(5):e1000069.

Zhao et al.; Both endoplasmic reticulum and mitochondria are involved in disc cell apoptosis and intervertebral disc degeneration in rats; Age (Dordr). Jun. 2010;32(2):161-77.

Zinszner et al.; CHOP is implicated in programmed cell death in response to impaired function of the endoplasmic reticulum; Genes Dev. Apr. 1, 1998;12(7):982-95.

International Search Report, dated Jul. 31, 2019, for The University of Hong Kong, International Application No. PCT/IB2019/052321, dated Mar. 21, 2019.

Written Opinion, dated Jul. 31, 2019, for The University of Hong Kong, International Application No. PCT/IB2019/052321, dated Mar. 21, 2019.

International Search Report, dated Jan. 17, 2018, for The University of Hong Kong, International Application No. PCT/IB2017/055783, dated Sep. 22, 2017.

Written Opinion, dated Jan. 17, 2018, for The University of Hong Kong, International Application No. PCT/IB2017/055783, dated Sep. 22, 2017.

Bateman et al.; Mutations of COL10A1 in Schmid metaphyseal chondrodysplasia; Hum Mutat. Jun. 2005;25(6):525-34.

Das et al.; Preventing proteostasis diseases by selective inhibition of a phosphatase regulatory subunit; Science. Apr. 10, 2015;348(6231):239-42.

(56) References Cited

OTHER PUBLICATIONS

Dougan et al.; Derlin-2-deficient mice reveal an essential role for protein dislocation in chondrocytes; Mol Cell Biol. Mar. 2011;31(6):1145-59.

Eisen et al.; Cluster analysis and display of genome-wide expressioni patterns; Proc Natl Acad Sci U S A. Dec. 8, 1998;95(25):14863-8.

Fitts; Ethics and animal numbers: informal analyses, uncertain sample sizes, inefficient replications, and type I errors; J Am Assoc Lab Anim Sci. Jul. 2011;50(4):445-53.

Franke et al.; Formation of new chromatin domains determines pathogenicity of genomic duplications; Nature. Oct. 13, 2016;538(7624):265-269 Epub Oct. 5, 2016.

Gawron et al;Endoplasmic reticulum stress in chondrodysplasias caused by mutations in collagen types II and X; Cell Stress Chaperones. Nov. 2016;21(6):943-958. Epub Aug. 1, 2016.

Gentleman et al.; Bioconductor: open software development for computational biology and bioinformatics; Genome Biol. 2004;5(10):R80. Epub Sep. 15, 2004.

Guimarães-Camboa et al.; HIF1α Represses Cell Stress Pathways to Allow Proliferation of Hypoxic Cardiomyocytes; Dev Cell. Jun. 8, 2015;33(5):507-21.

Kheradpour et al.; Systematic discovery and characterization of regulatory motifs in ENCODE TF binding experiments; Nucleic Acids Res. Mar. 2014;42(5):2976-87.

Lacraz et al.;Tomo-Seq Identifies SOX9 as a Key Regulator of Cardiac Fibrosis During Ischemic Injury; Circulation. Oct. 10, 2017;136(15):1396-1409 Epub Jul. 19, 2017.

Liu et al.; Transcriptional control of chondrocyte specification and differentiation; Semin Cell Dev Biol. Feb. 2017;62:34-49 Epub Oct. 19, 2016.

Lv et al.;Osteoarthritis Cartilage. Oct. 2016;24(10):1826-1836 Epub May 11, 2016.

López-Hernández et al.; Br J Pharmacol. Jun. 2015;172(11):2838-51.

Matys et al.; TRANSFAC: transcriptional regulation, from patterns to profiles; Nucleic Acids Res. Jan. 1, 2003;31(1):374-8.

Myszczyszyn et al.; The Role of Hypoxia and Cancer Stem Cells in Renal Cell Carcinoma Pathogenesis; Stem Cell Rev. Dec. 2015;11(6):919-43.

Pakos-Zebrucka et al.; The integrated stress response; EMBO Rep. Oct. 2016; 17(10):1374-1395. Epub Sep. 14, 2016.

Rutishauser et al.; Endoplasmic reticulum storage diseases; Swiss Med Wkly. May 4, 2002;132(17-18):211-22.

Samartzis et al.;Osteoarthritis Cartilage. Oct. 2016;24(10):1753-1760. Epub Apr. 30, 2016.

Sandelin et al.; JASPAR: an open-access database for eukaryotic transcription factor binding profiles; Nucleic Acids Res. Jan. 1, 2004;32(Database issue):D91-4.

Smith et al.; Tissue-specific regulatory elements in mammalian promoters; Mol Syst Biol. 2007;3:73. Epub Jan. 16, 2007.

van den Beucken et al.; Translational control of gene expression during hypoxia; Cancer Biol Ther. Jul. 2006;5(7):749-55. Epub Jul. 1, 2006.

Wang et al.; Sequence features and chromatin structure around the genomic regions bound by 119 human transcription factors; Genome Res. Sep. 2012;22(9):1798-812.

Weber et al.; Expression of translation initiation factor IF2 is regulated during osteoblast differentiation; J Cell Biochem. 2001;81(4):700-14.

Wouters et al.; Hypoxia signalling through mTOR and the unfolded protein response in cancer; Nat Rev Cancer. Nov. 2008;8(11):851-64. doi: 10.1038/nrc2501. Epub Oct. 10, 2008.

Yang et al.; ATF4 is a substrate of RSK2 and an essential regulator of osteoblast biology; implication for Coffin-Lowry Syndrome; Cell. Apr. 30, 2004;117(3):387-98.

Sara E. Patterson et al., "Mechanisms and Models of Endoplasmic Reticulum Stress in Chondrodysplasia", Developmental Dynamics 243:875-893, 2014.

Oct. 27, 2021 CN First Office Action, Application No. 201780058349.2.

* cited by examiner

Figure 1E

|  | Wild type (n=12) | 13del (n=14) |
|---|---|---|
| Tibia (cm) | 1.72 ± 0.04 | 1.47 ± 0.04 |
|  |  | 85% of Normal |
| Femur (cm) | 1.35 ± 0.04 | 1.22 ± 0.06 |
|  |  | 90% of Normal |
| Spine* (cm) | 2.08 ± 0.06 | 1.98 ± 0.10 |
|  |  | 95% of Normal |
| Ratio |  |  |
| Tibia / spine | 0.82 ± 0.03 | 0.65 ± 0.03 |
|  |  | 79% of Normal |
| Femur / spine | 0.74 ± 0.03 | 0.62 ± 0.04 |
|  |  | 83% of Normal |

Figure 1F

| Features | MCDS Patients | 13del Mice |
|---|---|---|
| Short Stature | ✓<br>< 3rd Percentile at the age of 5 years<br>(< 85% of 97th Percentile) | ✓<br>~85% of Normal |
| Short Limbs | ✓ | ✓ |
| Flaring of Metaphyses | ✓ | ✓ |
| Genu Varum (bowing legs) | ✓ | ✓ |
| Coxa Vara | ✓ | ✓ |
| Hip Deformation | ✓ | ✓ |
| Platyspondyly (Flat Vertebral Bodies) | ✓ | ✓ |
| Abnormal Vertebral Endplates | ✓ | ✓ |
| Widen Growth Plate | ✓ | ✓ |
| Hyperostosis |  | ✓ |

Figure 2I
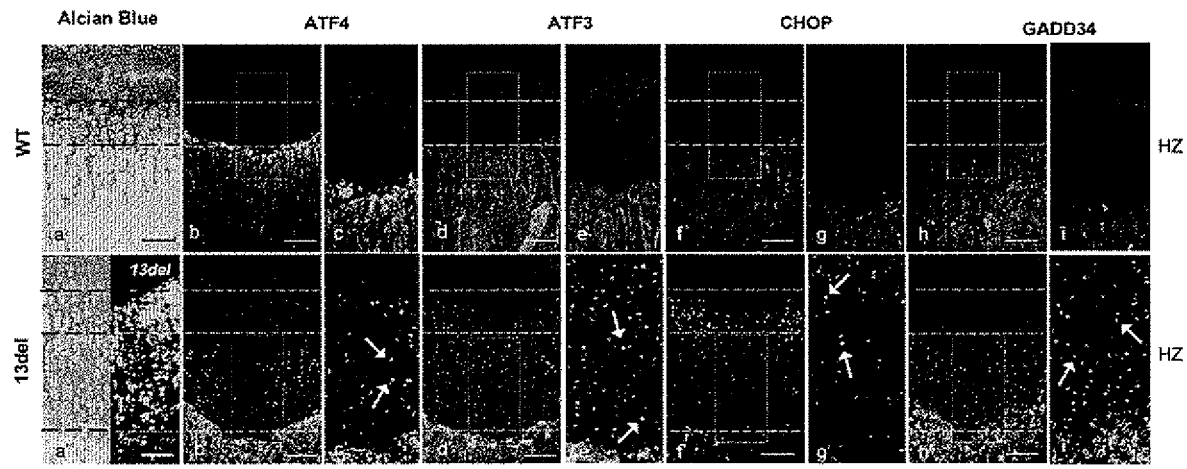
Figure 2J
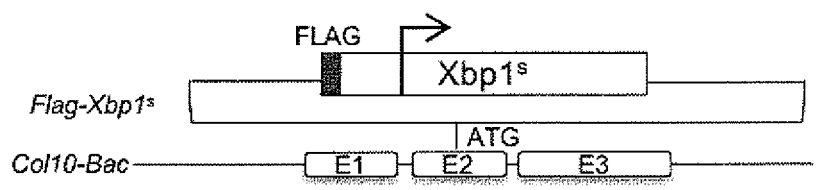
Figure 2K

| TF | Expression Trend | | ATF4 Binding Peak | | |
|---|---|---|---|---|---|
| | WT | 13del | ATF4 Peak Loci | Regulatory Region | Distance to TSS |
| SOX9 | | | Chr11: 112642927- 112643074 | promoter | 450 bp |
| SOX5 | | | Chr6: 143916666- 143916879 | intron | 240 kb |
| SOX6 | | | Chr7: 122876412- 122876588 | intron | 310 kb |
| MEF2C | | | - | - | - |
| MEF2D | | | - | - | - |
| RUNX2 | | | Chr17: 44846891-44847128 | intron | 106 kb |
| RUNX3 | | | - | - | - |
| GLI1 | | | - | - | - |
| GLI2 | | | Chr1: 120950226-120950319 | promoter | 50 bp |
| GLI3 | | | Chr13: 15554627-15554793 | promoter | 300 bp |
| FOXA2 | | | - | - | - |
| FOXA3 | | | - | - | - |

**$p < 0.005$

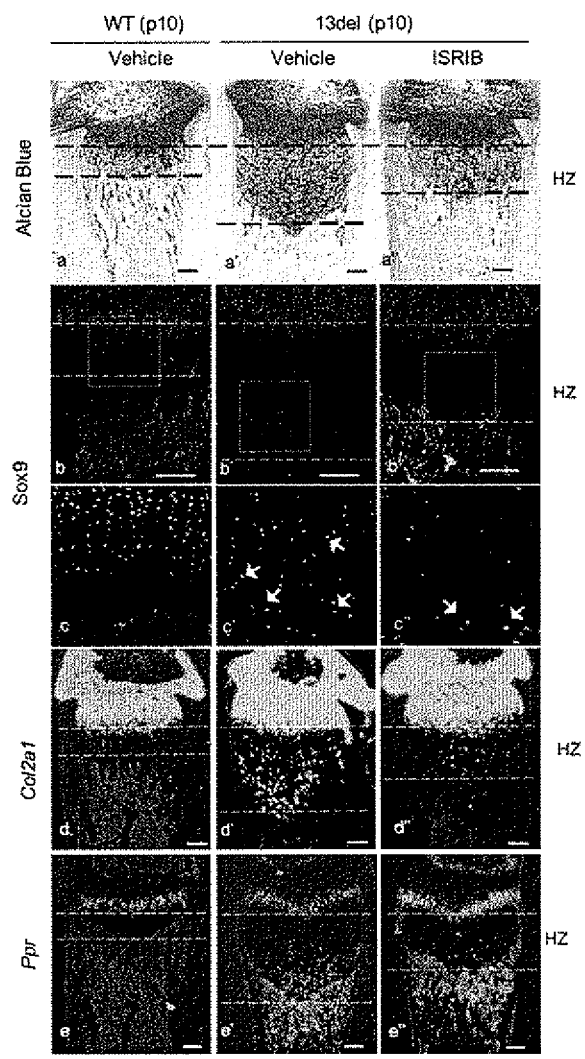

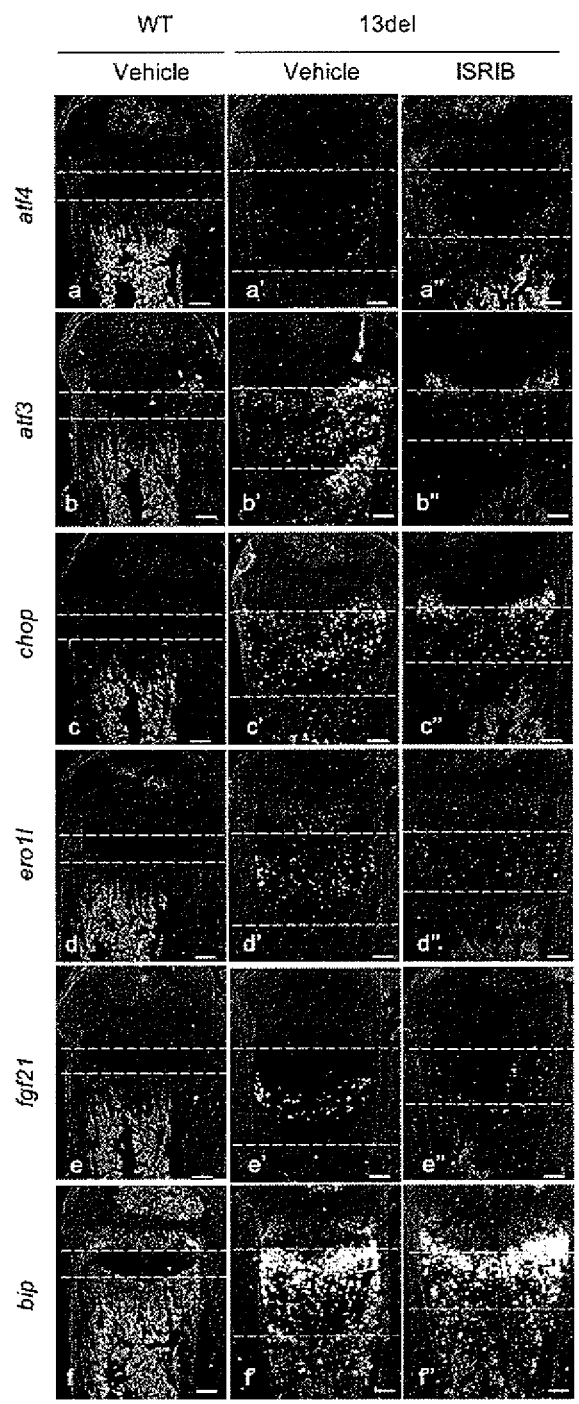

6-month (human 34yrs)

HIF 1α

13DEL/EF5

PREVENTIVE AND THERAPEUTIC APPROACH FOR ABERRANT CELL DIFFERENTIATION AND ISR-ASSOCIATED DISEASES

CROSS-REFERENCE TO RELATED APPLICATIONS

This application claims the benefit of U.S. Ser. No. 62/398,514, filed Sep. 22, 2016, the entire contents and disclosures of which are hereby incorporated by reference into this application. This application also cites various publications, the entire contents of which are incorporated herein by reference into this application.

FIELD OF THE INVENTION

This invention relates to a method of preventing, ameliorating and/or treating diseases and disorders associated with the integrated stress response arising from cellular stresses involving the phosphorylated eukaryotic initiation factor 2α (p-eIF2α) pathway. In one embodiment, the present invention provides a method which prevents or alleviates aberrant cell differentiation associated with the p-eIF2α pathway.

BACKGROUND OF THE INVENTION

Congenital skeletal disorders in human lead to physical disabilities and generate difficulties in education, employment and social life (1). In particular, children with significantly short stature are vulnerable to diverse developmental, social and educational problems (2). These barriers are highly likely to exert a strong influence on quality of life. However, current treatment options in skeletal disorders are extremely limited and may involve controversial surgical procedures such as limb lengthening (3).

It is well established that mutations in genes encoding extracellular matrix (ECM) components cause skeletal disorders. For example, mutations in genes encoding collagen I cause osteogenesis imperfecta (OI) (4); Metaphyseal chondrodysplasia, type Schmid (MCDS) is associated with heterozygous mutations in the COL10A1 gene (5); Pseudoachondroplasia (PSACH) and multiple epiphyseal dysplasia result from mutations in COMP, matrilin-3 or collagen IX (6-8). However, it has long been debated whether these disorders arise because of haploinsufficiency of the ECM or because of the intracellular dominant negative impact of these mutant proteins. Recent molecular evidence supports the notion that the underlying pathology is the consequence of retention of such mutant ECM proteins in the endoplasmic reticulum (ER), which induces ER stress and the adaptive unfolded protein response (UPR) (9, 10). Targeting the UPR is therefore a strategy for the treatment of skeletal disorders associated with ER stress.

MCDS patients are characterized by short stature, waddling gait, and genu varum (bowing legs). Radiographic analyses also reveal coxa vara (the angle between the proximal head and the shaft of the femur is less than 120°), wider and irregular growth plates, mild spinal syndromes including platyspondyly (flat vertebral bodies), and abnormal vertebral endplates (11). Previously, a transgenic mouse model (13del) has been generated to carry an equivalent human mutation (13 bp deletion) in the Col10a1 transgene and recapitulates phenotypic features of MCDS (10) and in addition generalized hyperostosis (U.S. Pat. No. 6,369,295). The 13-bp deletion causes a frameshift in the NC1 coding domain of collagen X (FIG. 1A), and results in misfolding of this protein in the ER and activation of UPR in 13del-HCs (FIG. 1B).

Significant dwarfism can be observed in 13del mice (FIG. 1C). In human, the average height of MCDS children is approximately 85% of normal at the age of five (12). In 13del mice, the body length is about 90% of normal at p10 (equivalent to 5 years old in human), and progresses to 85% of normal after weaning. The 13del mice also feature disproportionate dwarfism, coxa vara (FIGS. 1D and 1E), and other MCDS-like phenotypes (summarized in FIG. 1F). The most characteristic skeletal phenotype of MCDS mice is the expansion of the hypertrophic zone in the growth plates of long bones. This phenotype is consistent with a reverted chondrocyte differentiation program, marked by re-expression of premature chondrocyte markers (Ppr, Sox9 and Col2a1) (FIG. 1G) (10). Although chronic ER stress would normally trigger cell apoptosis to eliminate stressed cells (13), 13del-HCs survive the ER stress (FIG. 1H) (10).

The subject invention disclosed a model in which induction of the UPR in hypertrophic chondrocytes (HCs) changes the differentiation program to a less differentiated state that allows them to adapt and survive. As a consequence, the changed differentiation program causes the growth plate abnormalities and consequent skeletal deformities in MCDS (10).

As discussed in the following sections, the present model places the UPR as the underlying molecular pathology of MCDS and raises the possibility of using the 13del mice as a preclinical animal model to develop potential interventions to alleviate the MCDS phenotype. A prerequisite of such pilot intervention is to demonstrate a direct molecular link between the UPR and the 13del phenotype.

Sustained activation of UPR has been implicated in the progression of a variety of diseases, including cancer, diabetes, inflammatory disease and neurodegenerative disorders (14). In the past few years, UPR is becoming an attractive target for drug discovery. Bioactive small molecules targeting the UPR pathway have been tested in chondrodysplasia animal models (15, 16). However, the disease phenotypes were not improved (15) or even worsened (16) after the administration of chemical chaperones or ER-stress reducing reagents. These findings suggest that UPR contributes to chondrodysplasia not just through the protein folding pathway, and the pathogenesis of this ER stress/UPR associated disease might involve additional UPR pathway effector(s) that is critical for normal skeletal physiology and homeostasis.

Upon ER stress, UPR activates three independent ER stress sensors: inositol-requiring 1 (IRE1), PKR-like ER kinase (PERK), and membrane-tethered activating transcription factor 6 (ATF6) (17). Amongst, activation of the PERK signaling pathway is likely to be the first line of defense against ER stress and is a central part of more general integrated stress response (ISR), activated by diverse stress stimuli and is implicated in many diseases including cancer, diabetes, obesity, neurodegeneration, skeletal disorders (18). Recently, ISR has been implicated in intervertebral disc degeneration (19, 20), which is very common in humans, and often causes low back pain (LBP).

In the past decades, surgical therapy has been undertaken to correct bone deformities in patients with short stature, including achondroplasia, hypochondroplasia, MCDS and other skeletal dysplasias. Current treatment of disc degeneration and LBP is mainly surgical, often involving removal of the disc and spinal fusion (21). Currently, there are no effective pharmacological therapies for abovementioned skeletal diseases. Growth hormone (GH) therapy has been used to treat dwarfism but is clarified to be ineffective for height gain in most congenital skeletal dysplasias, and in some cases with severe spinal deformities, it even results in worsened kyphosis and lordosis (22). Studies have also been reported to test the feasibility of chemical chaperone or ER-stress reducing reagents in animal models of ER stress related chondrodysplasia. Mouse models of chondrodysplasia have been treated with various ER stress reducing reagents: lithium, valproate, or phenylbutyric acid (PBA) and found to be ineffective (15, 16).

Integrated stress response (ISR) has a central role in many forms of cellular stress such as oxidative stress, hypoxia, ER stress and its induction is associated with diverse common diseases, such as cancer, diabetes, fibrosis, obesity, neurodegeneration and skeletal disorders (18). With activation of the PERK pathway as an immediate early response of the UPR and the ISR, PERK modulators have the potential in the treatment of cancer and neurodegenerative diseases (78-80). In particular to neurodegenerative diseases, although restoring protein synthesis through pharmacological inhibition of PERK in prion-infected mice using GSK2606414 could be neuroprotective, long term benefit could not be assessed because of side effects of weight loss and pancreatic toxicity (79). Pharmacological inhibition of PERK mediated phosphorylation of tau in a transgenic model of Frontotemporal Dementia was shown to be protective against further neuronal loss (81). These approaches address the postnatal impact of activating the UPR and PERK in neurodegeneration and also highlight the importance of determining the precise mechanism of causality of the UPR under specific scenarios of degeneration versus cell differentiation in development (82).

While stress responses commonly result in apoptosis, understanding how cells adapt, survive and a molecular understanding on the consequences of inducing the ISR on cell fate and differentiation in vivo is lacking. The majority of molecular mechanistic insights of the impact of the ISR are based on cell based assays not in vivo. Through an in vivo model of human chondrodysplasia, the present invention for the first time provides a mechanistic insight into the question of impacts of the ISR on cell fate and importantly addressed the possibility of preventive therapy.

BRIEF SUMMARY OF THE INVENTION

The present invention describes a method of preventing, ameliorating and/or treating disorders or diseases associated with the integrated stress response (ISR) involving the phosphorylated eukaryotic initiation factor 2α (p-eIF2α) pathway arising from various cellular stresses such as oxidative stress, hypoxia and ER stress, chronic or prolonged bio-mechanical stress. In one embodiment, the present invention provides a method which prevents or alleviates aberrant cell differentiation that is caused by the activation of the integrated stress response and thereby prevents or alleviates conditions, disorders or diseases resulting therefrom. In one embodiment, ISR-associated diseases subject to the present invention include but are not limited to skeletal disorders including disc degeneration, MCDS and other skeletal dysplasias, cancers, inflammatory diseases, diabetes, fibrosis, obesity and neurodegenerative diseases. In another embodiment, the present invention provides a method of using a p-eIF2α-modulator for the prevention or treatment of conditions, disorders or diseases described herein.

BRIEF DESCRIPTION OF THE DRAWINGS

FIGS. 1A-1H show dwarfism, skeletal deformities, histological and molecular defects in 13del transgenic mice. FIG. 1A is a diagrammatic representation of the 10.4 kb Col10a1-13del transgene used for generating the 13del mice. In FIG. 1B, the co-localization of mutant COLX$^{13del}$ protein (green) with the Con A (red) indicates 13del protein is accumulated within ER (left panel), which lead to the activation of UPR-associated factors in 13del HZ (atf4, chop and Bip) (right panel). In FIG. 1C, body lengths of the WT and 13del littermates were monitored from birth to 30 wk stage, and a consistent reduction of body length in 13del mice was observe. In FIG. 1D, radiographic analysis revealed the skeletal abnormality of 13del mice at 4-week stage. In FIG. 1E, statistics showed 13del mice displayed disproportionate dwarfism at 10-week stage (*Spine here indicates the length of 7 continuous vertebrae consisting of the last lumbar, four sacral and two caudal vertebrae). In FIG. 1F, 13del transgenic mice display both MCDS-like and non-MCDS features. In FIG. 1G, growth plate is abnormally expanded in 13del proximal tibia at 10-day stage. Hypertrophic chondrocytes (HCs) in the lower part of hypertrophic zone (HZ) re-expressed markers more typical of pre-HCs (Sox9, Col2a1 and Ppr). In FIG. 1H, TUNEL assay revealed apoptotic cells with yellow nuclei (arrows) were present at the chondro-osseous junction in wild type (left panel). In 13del mice (middle and right panel), no cell death was detected in ER stressed HCs, while a few apoptotic nuclei were found near the bone collar.

FIGS. 2A-2M show PERK signaling pathway regulates reverted chondrocyte differentiation. FIG. 2A shows a schematic PERK signaling pathway in eukaryotes. FIG. 2B is a schematic diagram of the rationale for fractionating the WT and 13del p10 growth plates into different chondrocyte populations (left panel), based on the expression patterns of chondrogenic markers (Col2a1, Ihh, Ppr, Col10a1, Mmp13) and ER stress marker (BiP) (right panel). FIG. 2C shows the clustering analyses of differentially expressed genes in chondrocyte subpopulations in p10 WT and 13del proximal tibia growth plates. Expression levels were normalized from −0.5 (blue) to 0.5 (yellow). Four major clusters I, II, III and IV were identified (left panel). The average expression levels ($Log_2$ scale) of the genes in different clusters revealed significant expression pattern changes in 13del mice (right panel). In FIGS. 2D and 2E, genes in different clusters were functionally categorized using DAVID web tools. The enriched biological processes (FIG. 2D) and enriched pathway (FIG. 2E) were sequentially shown for Cluster I, II, III and IV. In FIG. 2F, PERK signaling and XBP1$^s$ regulating ERAD signaling pathway is highly enriched in KEGG pathway of protein processing in endoplasmic reticulum in Cluster I. Red stars indicated the mapped genes in this cluster. FIG. 2G illustrate the normalized microarray measurements of major components involved in PERK pathway (Atf4, Chop, Aft3, Gadd34 and Ero1l) in each zone of WT and 13del growth plates. FIG. 2H shows histology (a, a') and gene expression analysis of Atf4 (c, c'), Atf3 (d, d'), Chop (e, e'), and Ero1l (f, f') by radioactive in situ hybridization on the wild type and 13del growth plates at p10 stage. Hypertrophic chondrocytes are specifically marked by Col10a1 (b, b'). ER stressed hypertrophic chondrocytes are marked by Bip (g, g'). FIG. 2I refers to the in vivo validation of ATF4 (b, b', c, c'), ATF3 (d, d', e, e'), CHOP (f, f', g, g') and GADD34 (h, h', i, i') by immune-staining on WT and 13del growth plates at p10 stage. In FIG. 2J, enriched motifs on Cluster I genes were analyzed, using sequences of promoter region (+/−2 kb from the TSS) for these genes. Motifs matched to the TFs in the UPR were shown. FIG. 2K shows the scheme of XBP1$^s$ (spliced form) over-expressing vector, together with FLAG-tag, for generation of FXBP1$^s$ transgenic mice. FIG. 2L shows the results of hematoxylin & Eosin staining (a, a', e, e') and immunochemistry of COL10A1 (b, b', f, f'), FLAG (c, c', g, g') and XBP1$^s$ (d, d', h, h') for comparing the growth plate phenotypes between WT and FXBP1$^s$ transgenic mice at p10 and 4-week stages. FIG. 2M illustrate the measurement of HZ length of WT and FXBP1$^s$ at p10 stage.

FIG. 3H shows that ectopic expression of ATF4 does not cause cell death. FIG. 3I shows that ectopic expression of Atf4 in HCs was insufficient for stress response induction, indicated by in situ hybridization of ER stress markers (Bip, Atf3 and Chop).

FIG. 4A shows ectopic expression of Atf4 in HCs leads to accumulation of premature chondrocytes in C10-ATF4 HZ, indicated by chondrogenic markers Col10a1 (a, a', b, b'), Sox9 (c, c', d, d'), Col2a1 (e, e', f, f'), Ppr (g, g', h, h') and Ihh (i, i', j, j') transcripts. FIG. 4B is a presentation of ATF4 ChIP peaks on regulatory region (+/−2 kb from TSS) of vital chondrogenic transcriptional factors (SOX, MEF2, RUNX, GLI and FOXA). The expression trend of these factors in WT and 13del chondrocytes were measured by normalized microarray expression profile. FIG. 4C shows luciferase activities of Sox9 promoter reporter with different lengths (pSox9-2.7K, pSox9-1.8K and pSox9-0.8K) or ATF4 putative binding sites mutants (pSox9-1.8M1, pSox9-1.8M2 and pSox9-1.8M3) responding to different dosages of ATF4 were measured in ATDC5 cells. In FIG. 4D, ChIP-PCR showed the direct binding of ATF4 to the putative motif on the Sox9 promoter in vivo, using the nuclear extracts from E15.5 WT and C10-ATF4 limbs. An ATF4 ChIP-seq peak (dark triangle) around this region has been reported in ER-stressed MEF cells. FIG. 4E is a schematic diagram of generation of C10-ATF4; Sox9$^{C/C}$ and 13del; Sox9$^{C/C}$ mice, by using HC-specific Col10a1-Cre. FIG. 4F represents the genetic rescue of growth plate abnormalities of C10-ATF4 mice with HC-specific knock-out of Sox9 at p10 stage, as shown by histology (A, A'), expression analyses of SOX9 (B, B', C, C'), Col2a1 (D, D') and Col10a1 (E, E'). FIGS. 4G and 4H illustrate the HZ length measurement (FIG. 4G) and Col2a1 positive cells quantification (FIG. 4H) in C10-ATF4; Sox9$^{C/+}$ and C10-ATF4; Sox9$^{C/C}$ mice. FIG. 4I represents genetic rescue of growth plate abnormalities of 13del mice with HC-specific knock-out of Sox9 at p10 stage (n=5), as shown by histology (A, A'), expression analyses of SOX9 (B, B', C, C'), Col2a1 (D, D') and Col10a1 (E, E'). FIGS. 4J, 4K and 4L respectively illustrate the HZ length measurement and Col2a1 and Ppr positive cells quantification in 13del and 13del; Sox9$^{C/C}$ mice. FIG. 4M shows that ablation of Sox9 in WT HCs does not cause any abnormality at p10 stage, as shown by histology (a, a') and expression profiles of Sox9 (b, b'), Col2a1 (c, c'), Ppr (d, d') and Col10a1 (e, e').

FIGS. 5A and 5B indicate that the tibia length is further shortened in 13del; Chop$^{-/-}$ mice at p10 stage. The comparison was performed between 13del and 13del: Chop$^{-/-}$ littermates. In FIG. 5C, exacerbated growth plate abnormalities were observed in 13del mice with global loss of CHOP at p10 stage, shown by histology (a, a'), expression analyses of Col10a1 (b, b'), SOX9 (c, c', d, d'), Col2a1 (e, e') and Ppr (f, f'). FIGS. 5lD and 5E respectively shows the HZ length measurement, and SOX9, Col2a1 and Ppr positive cells quantification in 13del and 13del; Chop$^{-/-}$ mice. FIGS. 5F and 5G show the results of TUNEL assay which revealed increased number of apoptotic cells in 13del: Chop$^{-/-}$ HZ. FIG. 5H shows normalized microarray measurements of PERK signaling components (Chop, Atf3, Gadd34 and Ero1l), Chaperone (Bip, Dnajb9, Dnajb11 and Calnexin) and ER stress sensors (Atf4, Xbp1 and Atf6) in WT, 13del and 13del: chop$^{-/-}$ mice at p10 stage.

FIGS. 6A and 6B indicate HZ expansion is reduced in 13del; GADD34$^{-/-}$ mice. FIGS. 6C and 6D indicate fewer HCs revert to preHC-like cells in 13del; GADD34$^{-/-}$ mice, marking by Ppr. FIGS. 6E and 6F indicate the tibia length is further shortened in 13del;GADD34$^{-/-}$ mice at p10.

FIG. 7A shows the normalized microarray measurement of Fgf21 in 13del growth plate comparing with WT. FIG. 7O illustrates the normalized microarray measurement of Fgf21 in WT, 13del and 13del;Chop$^{-/-}$ chondrocytes.

FIG. 8A is a schematic timeline of the ISRIB (2.5 mg/kg) or vehicle (0.5% DMSO in 0.9% saline) administration. The mice were administrated by intraperitoneal injection, starting from E13.5 to p20 stage. The animals were harvested at indicated time-points. In FIGS. 8E and 8F, the radiographic analyses revealed that skeletal deformities of 13del mice were alleviated at p20 stage by ISRIB treatment, including length of tibia, femur and spine (spine here indicated by the length of 7 continuous vertebrae consisting of the last sacral and six tail vertebrae), pelvic bone deformation (θ1: the angle between ilium and pubis), Coxa Vara (θ2: the angle between the proximal head and the shaft of the femur) and Genu Varum (θ3: the angle between proximal head and distal head of tibia). FIGS. 8G and 8H shows the rescue of growth plate abnormalities in 13del mice by the treatment of ISRIB at p10 stage and p20 stage, as shown by histology (a-a") and in vivo expression profiles of SOX9 (b-b" and c-c"), Col2a1 (d-d") and Ppr (e-e"). FIG. 8O indicates that at p10, the transcripts of Atf4 (a-a"), Atf3 (b-b"), Chop (c-c"), Ero1l (d-d") and Fgf21 (e-e") were down-regulated in HZ from ISRIB-treated 13del mice, while Bip (f-f") was not affected. FIG. 8Q indicates that ISRIB treatment does not induce apoptosis in 13del mice.

FIG. 9A shows the ten-day-old WT, 13del-KI MCDS heterozygous (Col10a1$^{13d/+}$) and homozygous (Col10a1$^{13d/13d}$) mice. FIG. 9B shows that the growth plate expansion is paralleled to the number of reprogramming HCs in 13del-KI MCDS mice.

In FIG. 10A, the radiographic analysis reveals early onset of IDD in 20-years-old MCDS patient. In FIG. 10B, the FAST staining shows swelling of the nucleus pulpous (middle arrow), endplate expansion (upper and lower dashed arrows), and accumulation of chondrocyte-like cells in the inner annulus fibrosus (iAF) in 13del mice, at 4-week stage. In FIG. 10C, the radiographic analysis reveals severe intervertebral disc degeneration in tail region (T5/6, T6/7 and T7/8) in 7-, 9-, 12- and 16-month 13del mice. In FIG. 10D, histologically, the 13del tail intervertebral disc (IVD) exhibited significant characteristics of disc degeneration, including loss of NP/AF boundary, disc bulging and widening of the AF interlamellar space at both 6-month (upper panel) and 16-month (lower panel) stages. Notably, the cycled region clearly showed the inward bulging of inner AF (iAF) lamellae, and significant decreased volume of vascular canals in subchondral region between spinal growth plate and endplate in 6-month 13del mice. Moreover, at 16-month stage, the 13del disc clearly exhibited (a) the altered NP structure and matrix, (b) the inward bulging of AF lamellae and consequently fissure (boxed regions). In FIG. 10E, excessive cell death can be observed in NP of the degenerated tail IVD in 16-month 13del mice. In FIG. 10F, transcriptionally and translationally, the essential ER stress sensor BIP was ectopic upregulated in core region of 13del NP at 6-month stage.

FIGS. 11A-11D show ISRIB ameliorated the IVD syndromes of 13del mice. FIG. 11A shows that treatment of ISRIB (2.5 mg/kg) eased the IVD abnormalities in 13del lumbar spine, including less expanded endplate and more organized iAF structure. FIG. 11B shows that in 13del mice, treatment of ISRIB reduced the number of reprogrammed chondrocytes in the growth plates and endplates. Moreover, the ectopic expression of Opn in NP were greatly prevented. In FIG. 11C, in 13del lumbar IVD, ATF3, a downstream target of ATF4 is significantly activated in the HCs of the growth plate and endplate as well as in the NP (arrows). With the treatment of ISRIB, no ATF3 expression can be detected and there appeared to be fewer ATF3 expressing HCs.

FIGS. 12A and 12B indicate that HIF1α and HIF2α were upregulated in 13del-KI HCs. In FIG. 12C, EF5 staining clearly demonstrated hypoxia stress response was triggered in 13del-KI mice. In FIG. 12D, GFP/MCDS chimera demonstrated hypoxia stress (EF5 positive cells) is highly correlated with the cells expressing 13del protein. FIG. 12E shows that the 13del-expressing cells (green, upper panel) are under hypoxia stress, marked by EF5 (red, middle panel), in the HCS of the talus cartilage. FIGS. 12F and 12G show that HIF1α and HIF2α were upregulated in C10-ATF4 HCs.

FIGS. 13A-13D demonstrate the putative ATF4 binding regions on Sox9 within the topologically associated domains (TAD), indicating the potential ISR-regulation on Sox9 by enhancers. FIG. 13A shows human SOX9 (hSOX9) and mouse Sox9 (mSOX9) are located within the boundary region between 2 sub-TADs and share a highly conserved TAD pattern. FIGS. 13B and 13C demonstrated the highly conserved CCCT C-binding factor (CTCF) insulator binding region presenting in human and mouse Sox9 gene locus. FIG. 13D demonstrated an example of putative ATF4 binding enhancer region on mSox9.

DETAILED DESCRIPTION OF THE INVENTION

Figure 1A:
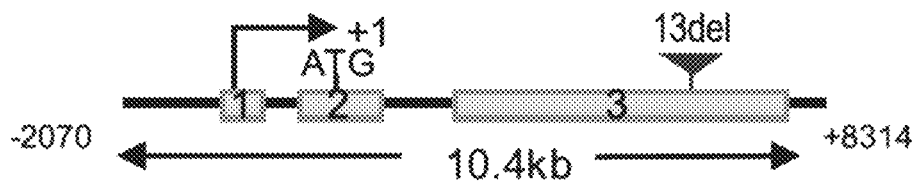
Figure 1B:
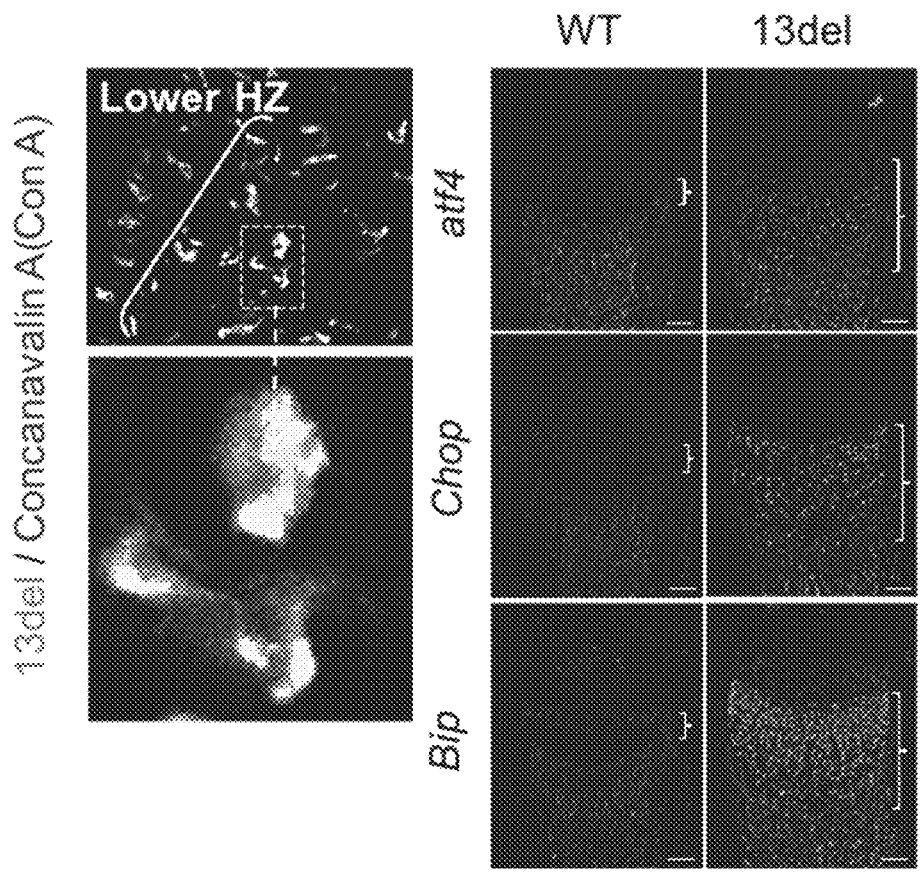
Figure 1C:
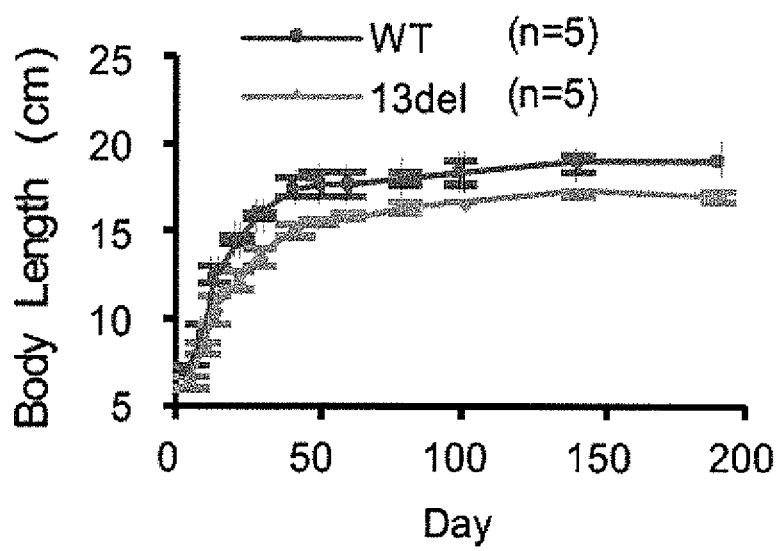
Figure 1D:
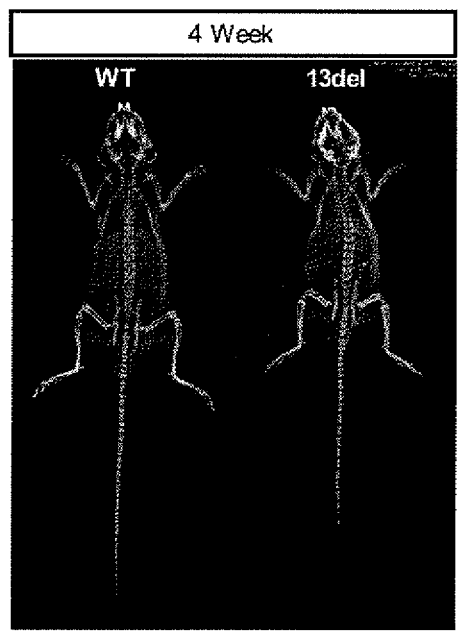
Figure 1G:
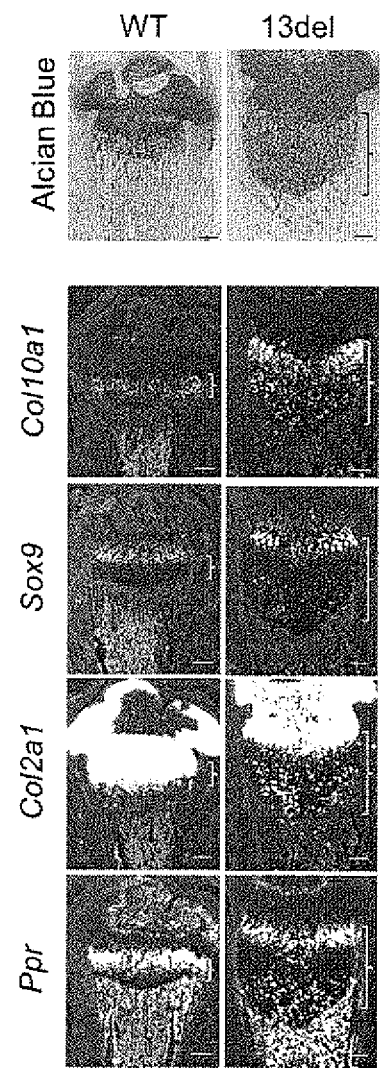
Figure 1H:
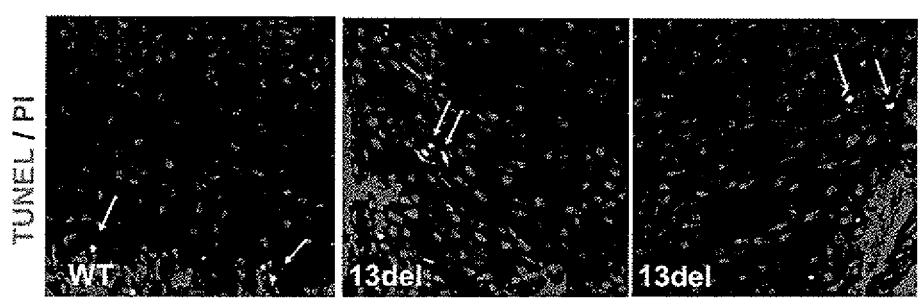

The present invention provides a method of preventing, ameliorating and/or treating conditions, disorders or diseases associated with the integrated stress response (ISR) involving the phosphorylated eukaryotic initiation factor 2α (p-eIF2α) pathway arising from various cellular stresses. As described herein, phosphorylated eukaryotic initiation factor 2α pathways or p-eIF2α pathways include signaling pathways where de-phosphorylated eIF2α or phosphorylated eIF2α is involved, and include signaling pathways which are directly or indirectly affected by the de-phosphorylation or phosphorylation of eIF2α.

ISR-Associated Skeletal Diseases

The first aspect of this invention is to provide a method of preventing, ameliorating and/or treating a skeletal disorder associated with or caused by the activation of the integrated stress response in a subject. Skeletal disorders subject to the present invention can be arising from cellular stresses such as oxidative stress, hypoxia and ER stress, or caused by chronic or prolonged biomechanical stress.

The integrated stress response (ISR) is an adaptive cell-survival pathway that can be activated when misfolded proteins trigger endoplasmic reticulum (ER) stress. It is implicated in development and diseases, with many human genetic skeletal deformities being caused by mutations that trigger the ISR.

In an MCDS transgenic mouse model (13del) which carries a 13 bp deletion in Col10a1 equivalent to the human mutation, misfolded mutant collagen X induces ER stress. Although the chondrocytes survive, their differentiation is reversed by an unknown mechanism to a more juvenile state characterized by the re-expression of prehypertrophic chondrocyte markers (Ppr, Sox9 and Col2a), disrupting endochondral ossification, and skeletal dysplasia ensues. A similar effect on hypertrophic chondrocyte differentiation has been described in other mouse models of dwarfism (70). The skeletal defects caused by mutations that induce stress or inactivate key transducers of the stress response in humans and mouse models implicate components of pathways involved in chondrocyte and osteoblast differentiation. However, the relationship between skeletal dysplasia and the ISR remains unclear.

The present invention represents the first mechanistic study in a model of human chondrodysplasia associated with ER stress that demonstrates causality and a direct link between the ISR and reprogrammed chondrocyte differentiation. Disclosed herein, ISR signalling reverses hypertrophic chondrocyte differentiation via ATF4-directed transactivation of the transcription factor gene Sox9. By genetic and molecular analyses, the present invention established that the major effect of the ISR is the preferential expression of ATF4 which activates the transcription of a potent transcription factor gene Sox9 (a key regulator of chondrocyte differentiation and proliferation) (FIG. 4). The present invention also discloses for the first time the dual action of CHOP and ATF4 in promoting hypertrophic chondrocyte survival, establishing the critical role of CHOP in partnership with ATF4 in enabling chondrocyte survival via the transactivation of Fgf21. The present invention highlights the complex consequences of activating ISR, in part because of the distinct roles of ATF4 in controlling cell differentiation and proliferation depending on cell context.

The present invention further demonstrates that treatment of mutant 13del mice with a small molecule inhibitor of the ISR pathway, ISRIB (trans-N,N'-(Cyclohexane-1,4-diyl)bis (2-(4-chlorophenoxy)acetamide) which targets the interaction between eukaryotic initiation factor 2 (eIF2) and eukaryotic initiation factor 2B (eIF2B) and thereby suppresses ATF4 induction, prevents the differentiation defects and ameliorates chondrodysplasia in the 13del mice (FIG. 8), and ameliorates the degenerative intervertebral disc (IVD) syndromes of the 13del mice (FIG. 1I). The failure of chemical chaperones or ER-stress reducing reagents to rescue chondrodysplasia in mouse models (15) and the benign impact of either absence of (30), or over expressing Xbp1s (this study) emphasizes cell context-dependent effects of the different arms of the UPR. Importantly, the present invention identifies a key causative role for the ISR in MCDS and demonstrates that targeting early in the pathway, i.e., at the level of PERK phosphorylation of eIF2α could be an effective therapeutic approach. As disclosed herein, the effect of ISRIB on the aberrant differentiation of ER-stressed HC reveals the contextual complexity of ISRIB action. On the one hand, it antagonizes ATF4, reversing or preventing the de-differentiation. On the other hand, reduced levels of ATF4 and CHOP enfeeble a cell survival mechanism. In the context of the 13del mutation, the net result improves mouse skeletal development. This may reflect the dominance of de-differentiation in the pathogenesis of the chondrodysplasia. By finding the dose of ISRIB that titrates ATF4-CHOP levels and is protective for de-differentiation without causing death of the stressed chondrocytes, the dualism inherent in the ISR may be exploited therapeutically. In the present invention, a dose of ISRIB is administered to a subject to achieve an optimal level of cell differentiation and cell survival. In one embodiment, 2.5 mg/kg of ISRIB is administered to a subject twice a day, effectively and substantially alleviating the defects. In another embodiment, 5 mg/kg ISRIB is administered to a subject twice a day. In various embodiments, the effective amount of ISRIB is 0.05-0.1, 0.1-1, 1-5, 5-10, 10-20, 20-25, 25-50 or 50-100 mg/kg per day. In one embodiment, the subject is treated for 1 day or up to 365 days. In various embodiments, the subject is treated for 5, 10, 25, 50, 75, 100, 125, 150, 175, 200, 225, 250, 275, 300, 325 or 350 days.

In one embodiment, the present invention provides a method of preventing, ameliorating and/or treating a skeletal disorder (including disc degeneration, MCDS and other skeletal dysplasias) associated with integrated stress response involving the p-eIF2α pathway in a subject using a molecule that targets the underlying p-eIF2α-pathway. In one embodiment, molecules to be used in the present invention are modulators which directly or indirectly suppress the translational or transcriptional expression of ATF4 or SOX9. Without limiting the generality of the foregoing, the following illustrates a few embodiments of the present invention.

Chondrodysplasia and Congenital Dwarfism

There has been no example whereby the impact on cell fate in a congenital disorder such as dwarfism can be prevented or ameliorated by targeting the ISR in vivo.

Therefore, the present invention provides for the first time a feasible approach for the prevention and improvement of congenital dwarfism caused by the activation of ISR.

In one embodiment, the present invention provides a method of preventing, ameliorating and/or treating a skeletal disorder associated with integrated stress response involving the p-eIF2α pathway in a subject. In one embodiment of the present invention, skeletal disorders include but are not limited to osteogenesis imperfecta (OI), metaphyseal chondrodysplasia, type Schmid (MCDS), pseudoachondroplasia (PSACH), and multiple epiphyseal dysplasia. In another embodiment, skeletal disorders subject to the present method are caused by mutation(s) of extracellular matrix (ECM) proteins accumulating in the endoplasmic reticulum, and mutation(s) of key signaling transducer of ISR. In one embodiment, said skeletal disorders are arising from cellular stresses such as oxidative stress, hypoxia, and ER stress. In another embodiment, said skeletal disorders are caused by chronic or prolonged biomechanical stress.

In one embodiment, the present invention provides a method of alleviating and/or reversing aberrant differentiation in a chondrocyte through the inhibition of ectopic expression of Sox9/SOX9 (mouse/human). In another embodiment, the present method prevents and/or alleviates conditions, disorders or diseases resulting from an aberrant chondrocyte differentiation. In one embodiment, the present method includes the use of a molecule which inhibits the ectopic expression of Sox9/SOX9. In another embodiment, the present method includes a use of a molecule which inhibits the ectopic expression of ATF4 which subsequently enhances the ectopic expression of Sox9. In one embodiment, the molecule is a modulator that is capable of directly or indirectly inhibiting the transcriptional or translational expression of ATF4.

In one embodiment, the modulator in the present invention is represented by Formula I:

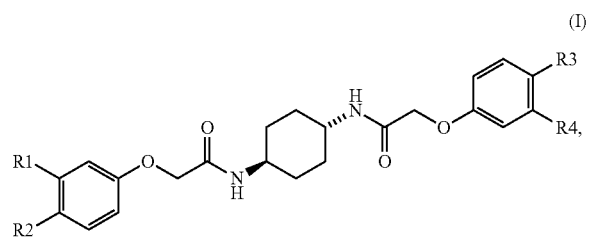

(I)

wherein each of R1, R2, R3 and R4 is independently hydrogen, halogen, —OCH3, —OCH2Ph, —C(O)Ph, —CH3, —CF3, —CCl3, —CN, —S(O)CH3, —OH, —NH2, —COOH, —CONH2, —NO2, —C(O)CH3, —CH(CH3)2, —CCSi(CH3)3, —CCH, —CH2CCH, —SH, —SO3H, —SO4H, —SO2NH2, —NHNH2, —ONH2, —NHC═(O)NHNH2, —NHC═(O)NH2, —NHSO2H, —NHC═(O)H, —NHOH, —OCH3, —OCF3, —OCHF2, —N3, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In one embodiment, the modulator represented by Formula I is ISRIB having the formula

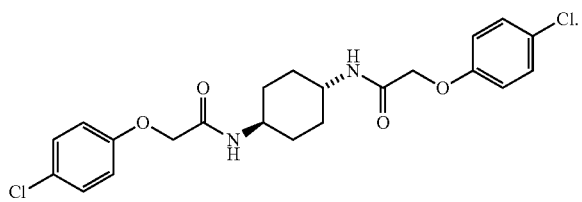 [SMILES: O=C(COc1ccc(Cl)cc1)N[C@H]1CC[C@H](NC(=O)COc2ccc(Cl)cc2)CC1]

In one embodiment, the modulator represented by Formula I includes molecules that are described in WO 2014/144952, the entire contents of which are incorporated herein by reference into this application.

In another embodiment, the modulator represented by Formula I is selected from the following molecules:

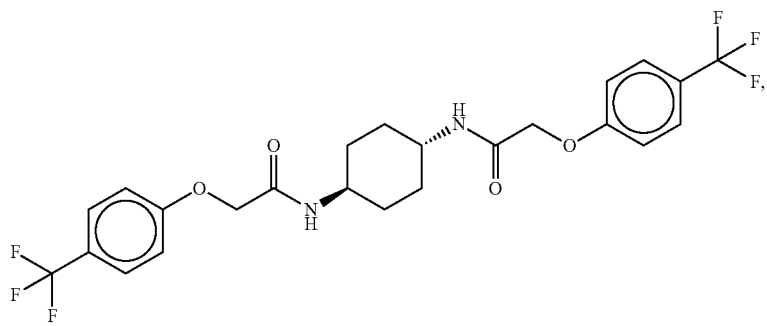

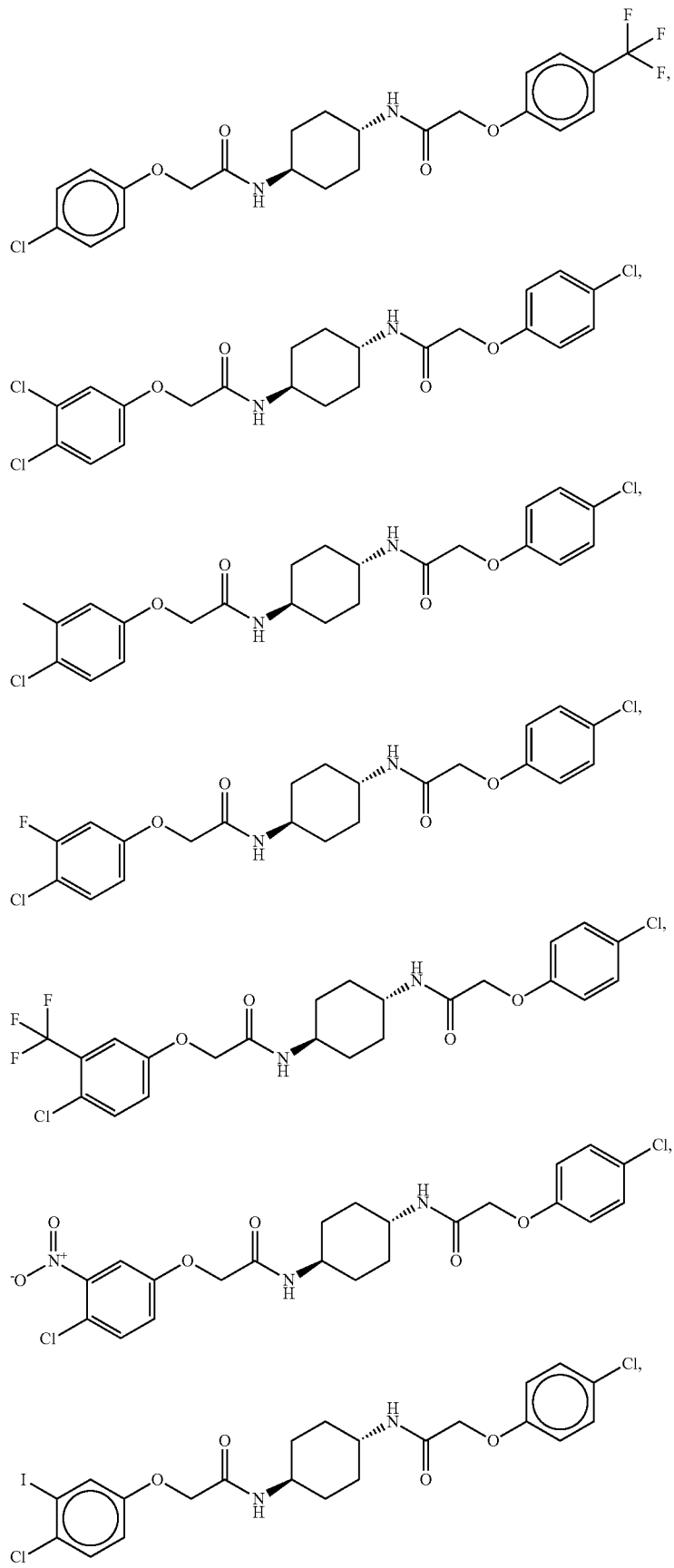

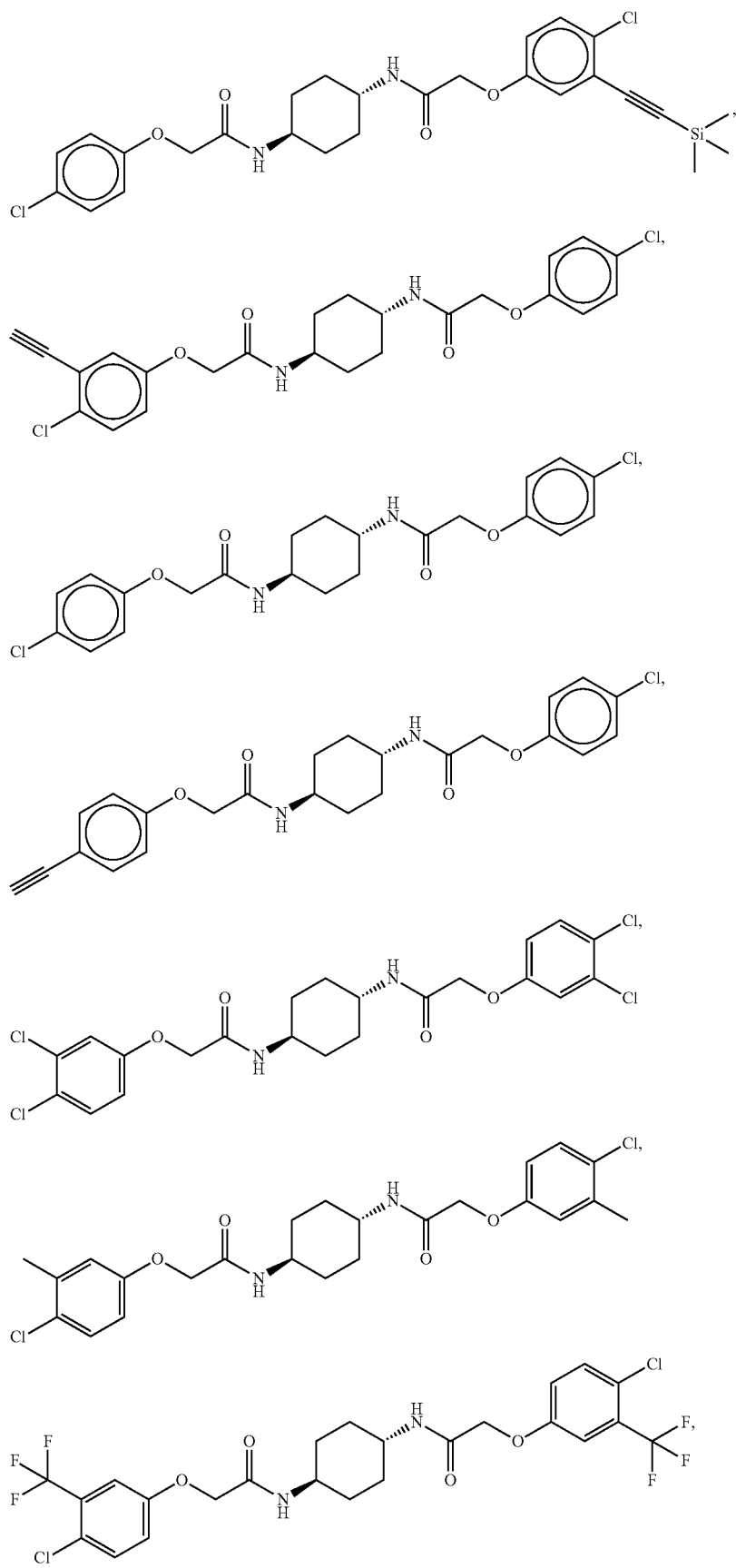

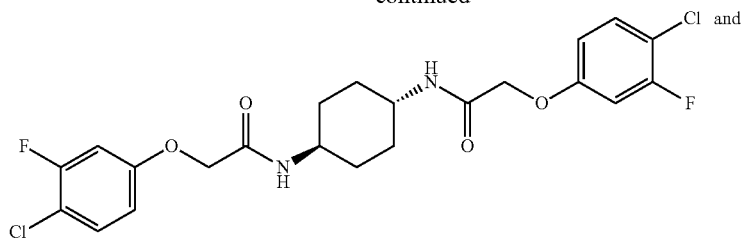

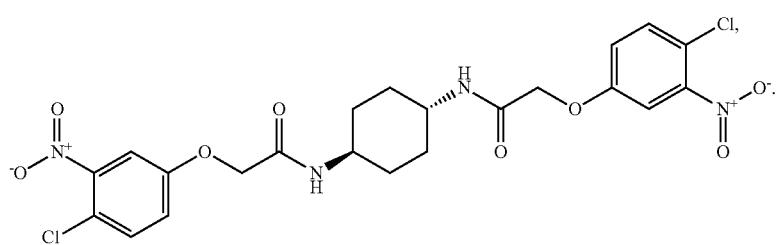

In one embodiment, the modulator subject to the present invention is represented by Formula II:

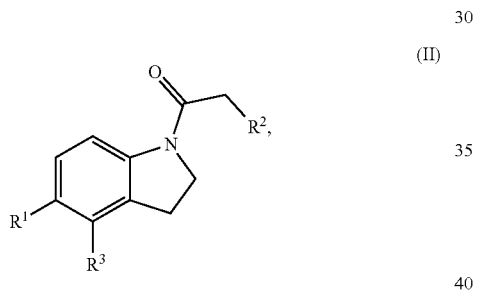

(II)

wherein $R^1$ is bicycloheteroaryl, including but not limited to pyrrolopyrimidine, which may be unsubstituted or substituted with groups such as amino and alkyl; $R^2$ is heteroaryl, including but not limited to pyridyl, pyrrolyl and pyrazolyl, which may be unsubstituted or substituted with groups such as halogen, alkyl and trihaloalkyl, and $R^3$ is hydrogen or halogen. In one embodiment, the modulator is represented by Formula II which includes molecules described in WO2011/119663, the entire contents of which are incorporated herein by reference into this application.

In one embodiment, the modulator represented by Formula II is GSK2656157 having the formula of

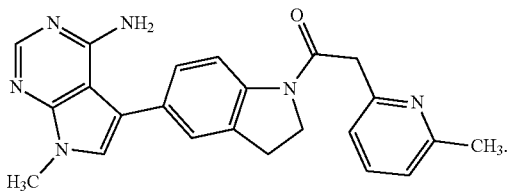 [SMILES: Cc1cccc(CC(=O)N2CCc3cc(-c4cn(C)c5ncnc(N)c45)ccc32)n1]

In various embodiments, the modulator represented by Formula II is selected from the following molecules:

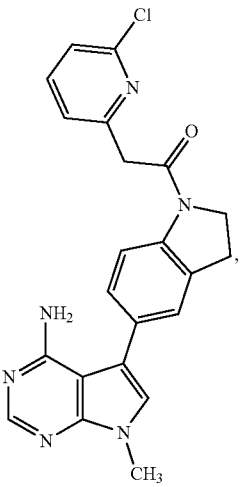

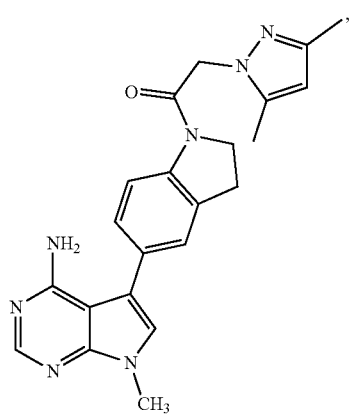

-continued
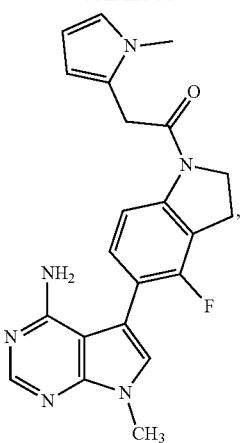
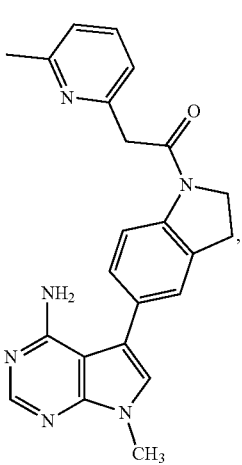
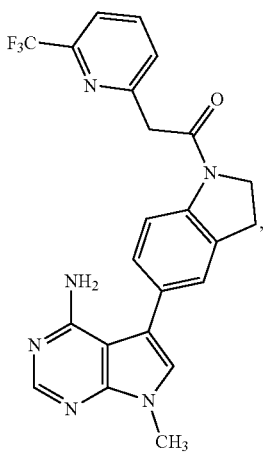
-continued
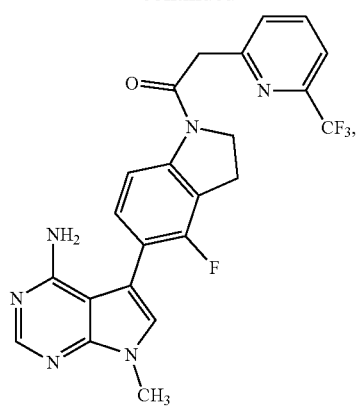
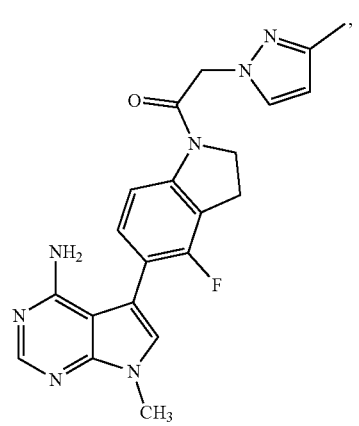
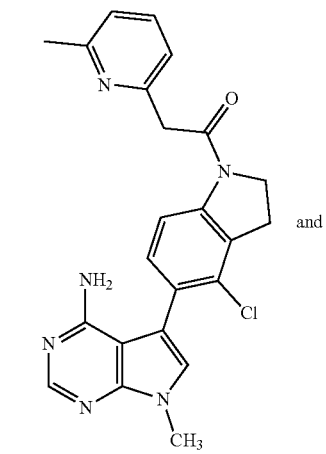
and -continued

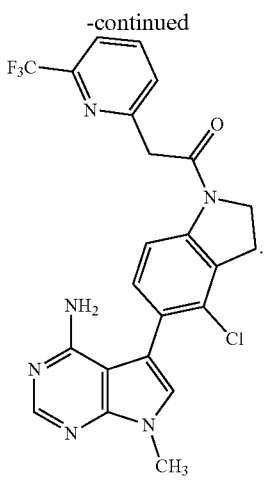

In one embodiment, the present method reduces the number of mature hypertrophic chondrocytes reversing to pre-mature chondrocytes as indicated by the decreased transcriptional or translational expression of immature chondrogenic markers such as Sox9, Col2a1, Ppr and Ihh.

In one embodiment, the present invention provides a method of ameliorating one or more conditions of MCDS or congenital dwarfism by modulating the p-eIF2α-pathway. In one embodiment, the method includes the use of a molecule which inhibits the effects of p-eIF2 on translation regulation or a molecule which inhibits the ectopic translational or transcriptional expression of Sox9 or ATF4 in the defective cells. In one embodiment, the conditions to be ameliorated by the present method include but are not limited to disproportionate dwarfism, short stature or limbs, flaring of metaphyses, genu varum (bowing legs), coxa vara, hip deformation, platyspondyly (flat vertebral bodies), abnormal vertebral endplates, widened growth plate and consequent disc degeneration.

Intervertebral Disc Degeneration (IDD)

In one embodiment, the present invention provides a method of preventing or ameliorating, intervertebral disc degeneration (IDD) caused by the activation of the integrated stress response pathway, which might induced by oxidative stress (23), hypoxia (24), ER stress (19), nutrition deprivation (25), accumulation of toxic metabolites (26) and/or excessive mechanical loading (27). In one embodiment, the present method of preventing or ameliorating, intervertebral disc degeneration (IDD) involves the use of one or more modulators or molecules described in the present invention. In 13del mice, the malformed spinal growth plates and endplates causes decreased volume of vascular canals in subchondral region between growth plates and endplates, consequently lowers the oxygen/nutrition importation and toxic metabolites exportation in nucleus pulpous, triggers oxidative stress (indicating by upregulation of ATF5), and changes cell differentiation indicating by ectopic expressing Sox9, Osteopontin (Opn) and α-SMA. Moreover, the ectopic expressing of matrix protein Opn alter the matrix deposition and induced ER stress, indicating by ectopic expression of ER stress sensor Bip and ATF4, and caused cell death at later stage. On the other hand, caged mouse normally used its tail to help its stand up for food and water, which might cause excessive mechanical loading to the tail of 13del with short stature. Consistently, the early onset of disc degeneration in 13del mice was always first observed in tail IVD (level 6-8), indicating the pathogenesis role of mechanical loading in IDD development. In one embodiment, the present invention uses a molecule that is capable of modulating the activation of ISR or its underlying stresses or causes in intervertebral disc cells for the prevention or treatment of IDD.

ISR-Associated Diseases Involving p-eIF2α Pathway

The second aspect of the present invention is to provide a method of preventing and/or ameliorating aberrant cell differentiation, or modulating cell fate determination through the modulation of ectopic expression of ATF4 and its potential downstream factors, such as Sox9/SOX9, in a cell. The present invention further provides a method of modulating ISR-associated diseases where aberrant cell differentiation is at least part of the underlying mechanism through the modulation of ectopic expression of ATF4 and its potential downstream factors, such as Sox9/SOX9, in a subject. In one embodiment, the present method of preventing and/or ameliorating aberrant cell differentiation, or modulating cell fate determination involves the use of one or more modulators or molecules described in the present invention.

The present invention highlights the potential of manipulating levels of the ISR for the treatment of ISR-associated human diseases resulted from various forms of cellular stress. As discussed above, ISR has a central role in many forms of cellular stress such as oxidative stress, hypoxia, ER stress and its induction is associated with diverse common diseases, such as cancer, inflammatory diseases, diabetes, fibrosis, obesity, neurodegeneration and skeletal disorders. The p-eIF2α signaling pathway, being a part of the ISR, could be a target for the prevention or treatment of these ISR-associated diseases. However, while stress responses commonly result in apoptosis, understanding how cells adapt, survive and a molecular understanding on the consequences of inducing the ISR on cell fate and differentiation in vivo is lacking. The majority of molecular mechanistic insights of the impact of the ISR are based on cell based assays not in vivo. The present invention exploited an in vivo model of a congenital developmental disorder (MCDS) in order to provide mechanistic insight into the question of impacts of the ISR on cell fate and importantly also addressed the possibility of preventive therapy.

Figure 3A:
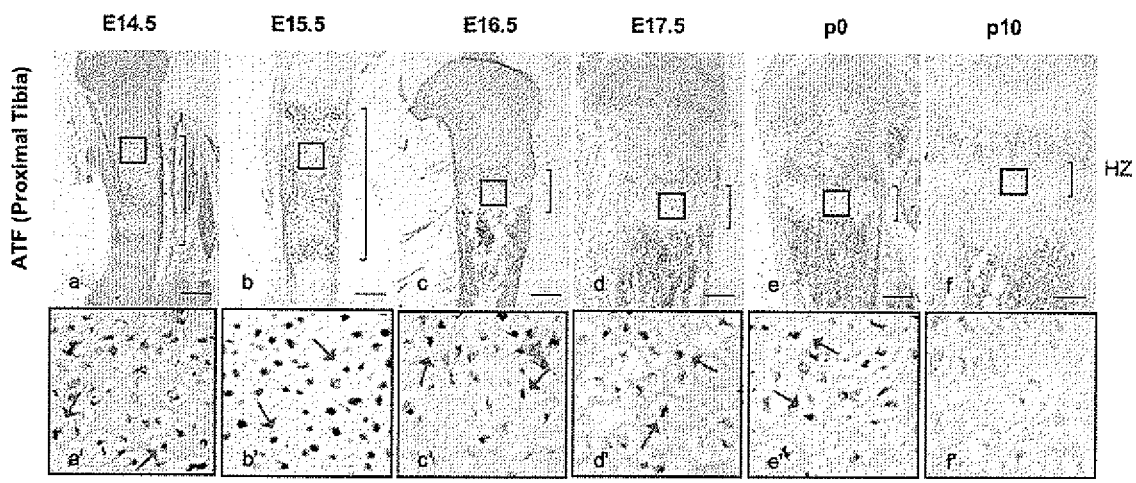
FIG. 3A are expression profiles of ATF4 on WT growth plates from E14.5 to P10 stages.

As reported herein, over-expression of ATF4 as part of the ISR has far reaching consequences in vivo, it directly activates the expression of Sox9 and thereby reverses the differentiation of a mature chondrocyte to a more immature state. SOX9 is a potent transcription factor with key roles in cell fate determination, not only in chondrocyte differentiation, but also in many other cell types, notably stem cells (e.g. dermal papilla, gonads, intestinal, and neural) and its overexpression or dysfunction results in many diseases including fibrosis and cancer (83). By preventing aberrant cell differentiation, titrated inhibition of the ISR emerges as a rationale therapeutic strategy for treating skeletal disorders or other disorders caused by ISR. The present invention revealed that given the importance of ATF4 to normal development, simply preventing its expression globally may not work therapeutically (FIG. 3A). Rather, the present invention introduces for a novel and viable approach to alter cell differentiation or cell fate by targeting the translational control of ATF4 that leads to its over expression.

In one embodiment, the present invention provides a method of modulating cell differentiation or cell fate using a molecule that modulates the ectopic expression of ATF4 and its potential downstream factors, such as Sox9/SOX9. In another embodiment, the present invention provides a method of preventing, ameliorating and/or treating an ISR-associated disease where cell differentiation or development is impacted in a subject, the method comprises a step of administering to said subject an effective amount of a molecule that modulates the ectopic expression of ATF4 and its potential downstream factors, such as Sox9/SOX9. In one embodiment, the present invention is used to prevent, ameliorate and/or treat diseases which are associated with or caused by an impacted cell differentiation or development, which include but are not limited to cancer, fibrosis, neurodegeneration and skeletal diseases. Firstly, it has been implied that cancer cells are selected to resist mild and prolonged ER stress by activating pro-survival UPR and PERK signaling pathway induces resistance to cell death elicited by endoplasmic reticulum stress and chemotherapy (28). Notably, gemcitabine resistance in pancreatic ductal adenocarcinoma is enhanced by activating multiple ISR-dependent pathways, including eIF2, Nrf2, Nupr1, BEX2, and Bcl2A1 (29). Moreover, increased phosphorylation of eIF2α in chronic myeloid leukemia cells contribute to the disruption of bone marrow niche components by cancer cells and in this way support CML progression (30). Secondly, the persistent presence of ER stress can increase cell death in injured tissues, induction of epithelial-mesenchymal transition (EMT) and promote fibrotic remodeling instead of the restoration of normal tissue architecture (31), and increased oxidative stress is a common pathological feature of fibrosis in a variety of organs, including lung (32), liver (33) and heart (34). Thirdly, both ER stress and oxidative stress have suggested to play important roles in neurodegeneration, such as Parkinson's disease, Alzheimer's and prion disease (35, 36). Finally, as discussed above, ER stress is associated with chondrodysplasias caused by mutations in ECM protein and mutations in key factors in ISR signaling pathway (37).

p-eIF2α Modulators

Without limiting the generality of the foregoing, the present invention provides a method of preventing, ameliorating and/or treating the conditions, disorders or diseases discussed herein using a molecule which targets the p-eIF2α pathway (a "p-eIF2α modulator"). In one embodiment, the present invention provides a method of preventing, ameliorating and/or treating a condition, a disorder or a disease associated with integrated stress response involving the p-eIF2α pathway in a subject, comprising the step of administering to said subject an effective amount of a p-eIF2α modulator. In another embodiment, the present invention provides a use of a p-eIF2α modulator for the preparation of a medicament for preventing, ameliorating and/or treating a condition, a disorder or a diseases associated with integrated stress response involving the p-eIF2α pathway. In another embodiment, the present invention provides molecules that are capable of modulating the p-eIF2α pathway for use in the treatment of diseases or modulation of conditions described herein.

In one embodiment, the subject is a human including an adult and a child, or an animal.

In one embodiment, "effective amount" means the amount of a molecule necessary to achieve a desired physiological effect.

In one embodiment, the present invention provides a method of modulating the p-eIF2α pathway in a cell or a population of cells, the method comprising contacting the cell(s) with an effective amount of a p-eIF2α modulator.

In one embodiment, p-eIF2α modulators are small molecules, nucleic acids, proteins or other biomolecules. In one embodiment, p-eIF2α modulators are small molecules which are represented by Formula I or II described above. In one embodiment, p-eIF2α modulators are p-eIF2α inhibitors that inhibit one or more downstream molecules or signaling events under the p-eIF2α pathway such as ISRIB and GSK2656157 and their analogs. In another embodiment, p-eIF2α modulators are molecules that activate one or more downstream molecules or signaling events under the p-eIF2α pathway such as Sulubrinal and Guanzbenz and their analogs. In yet another embodiment, p-eIF2α modulators are molecules that alter one or more downstream molecules or signaling events under the p-eIF2α pathway (for example, those illustrated in FIG. 2), and the p-eIF2α pathway can be part of the cellular stress responses such as oxidative stress, ER stress and hypoxia, or other chronic or prolonged biomechanical stress.

In one embodiment, said p-eIF2α modulators are capable of targeting eIF2α phosphorylation such as ISRIB and its analogs. In another embodiment, p-eIF2α modulators are molecules which are capable of targeting GADD34-Pp1c or promoting the assembly of GADD34-Pp1c. In yet another embodiment, p-eIF2α modulators are molecules which are capable of modulating the expression of ATF4 and its potential downstream factors, such as Sox9.

In one embodiment of the present invention, the effective amount of p-eIF2α modulator such as ISRIB to be given to a subject is 2.5 mg/kg to 20 mg/kg per day. In various embodiments, the effective amount of p-eIF2α modulator is 0.05-0.1, 0.1-1, 1-5, 5-10, 10-20, 20-25, 25-50 or 50-100 mg/kg per day. In one embodiment, the subject is treated for 1 day or up to 365 days. In various embodiments, the subject is treated for 5, 10, 25, 50, 75, 100, 125, 150, 175, 200, 225, 250, 275, 300, 325 or 350 days.

In one embodiment, two or more p-eIF2α pathway modulators are administered concurrently. In another embodiment where two or more p-eIF2α pathway modulators are to be administered, the second or subsequent p-eIF2α pathway modulators are administered immediately or a certain period after the administration of the previous p-eIF2α pathway modulator.

ATF4-Binding Site on Sox9 Locus and Binding Enhancers

In one embodiment, the present invention provides a method of inhibiting the ATF4/ISR mediated activation of transcription of murine Sox9/human SOX9, thereby preventing, alleviating and/or treating conditions resulting from the overexpression of SOX9; the method comprises a step of contacting the cells with, or administering to a subject, a molecule that is capable of blocking the ATF4-binding site on the Sox9/SOX9 locus, or by interfering with molecules that modulate the ATF4-mediated transcription of Sox9// SOX9 (such as a molecule that enhances the binding between ATF4 and Sox9/SOX9 locus, i.e., an ATF4-binding enhancer).

Figure 13A:
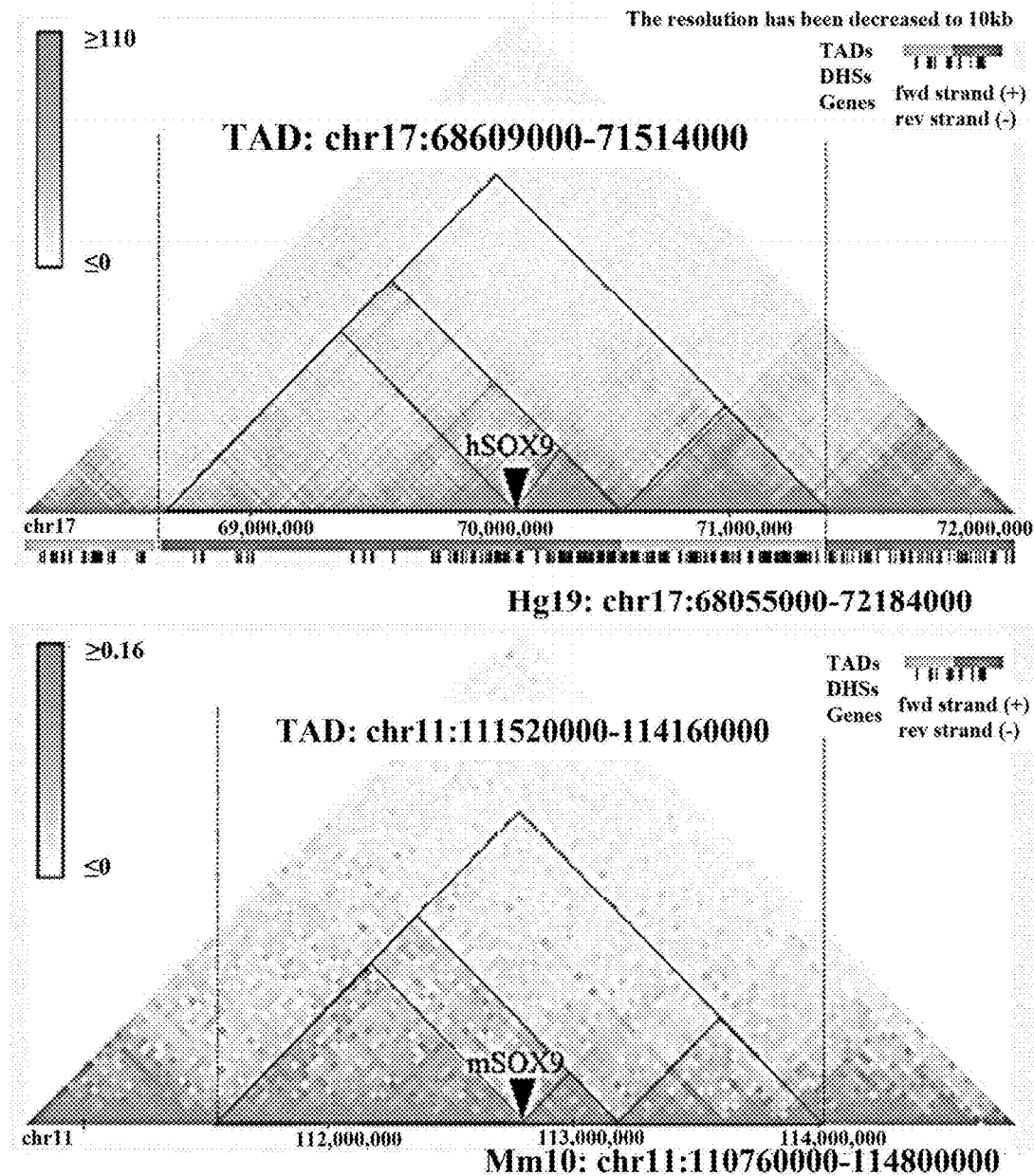
Figure 13B:
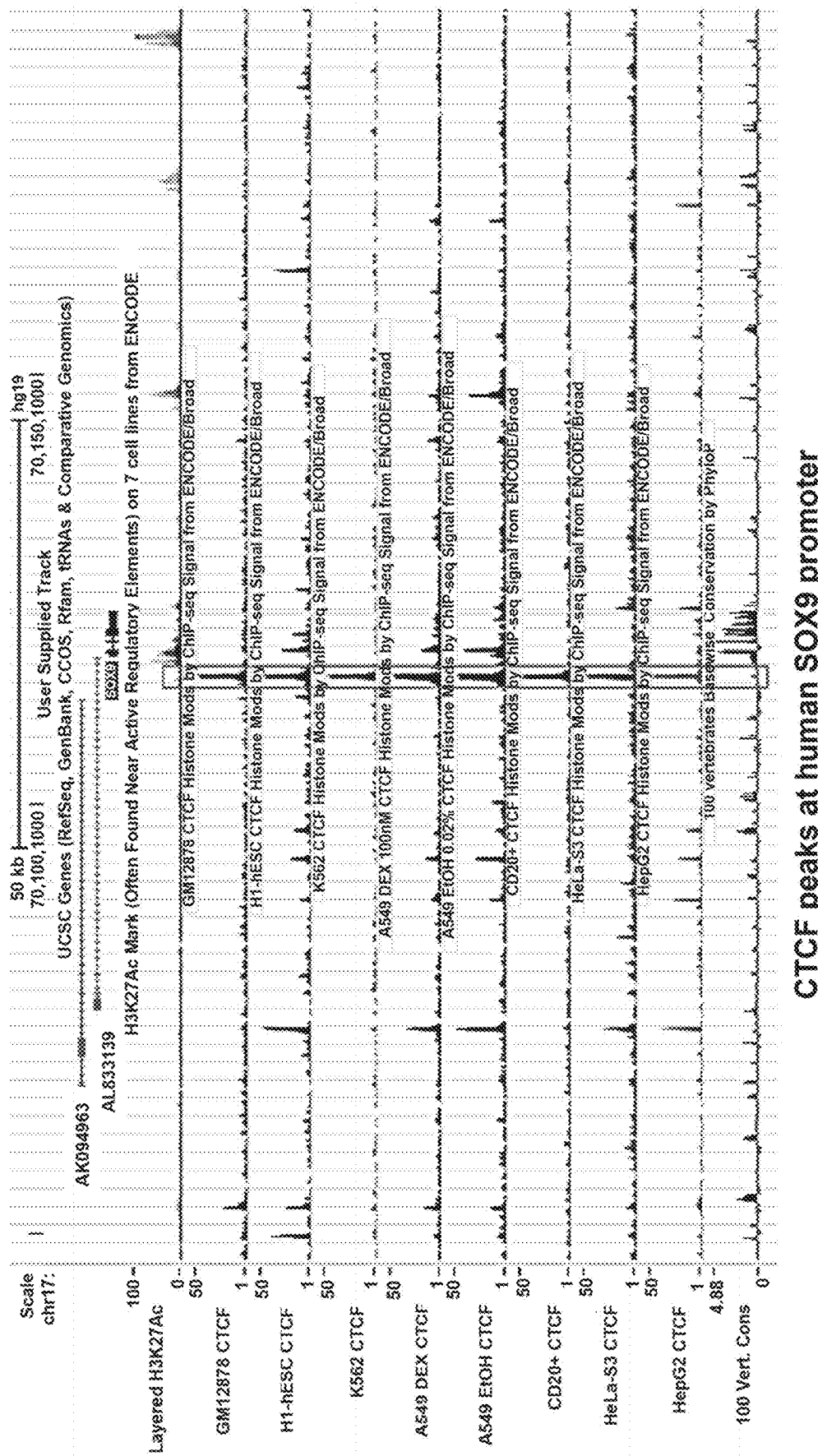

Sox9 was found to be located within the boundary between two sub-TADs (topologically associated domains) within chromosome 11 (chr11: 110760000-114800000), represented by chr11: 111520000-12200000 and chr11: 113160000-114160000 respectively (99, 100) (FIG. 13A, lower panel). Binding sites for ATF4 in mouse embryonic fibroblasts have been reported (44). While in human genome, SOX9 was found to be located in the boundary between two sub-TADs within chromosome 17 (chr17: 68055000-72184000), represented by chr17:68609000-69117000 and chr17:70514000-71514000 respectively (100, 101) (FIG. 13A, upper panel). The Sox9/SOX9 TAD pattern is conserved between human and mouse as indicated in FIG. 13B.

Figures 4A, 4B:
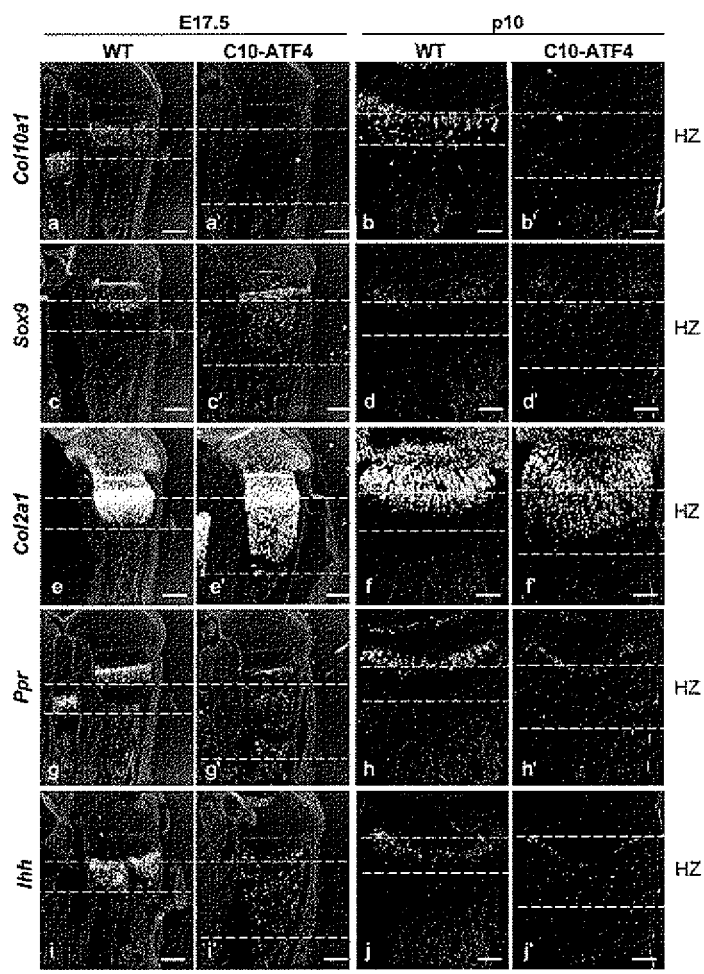
FIGS. 4A-4M show ATF4 modulates chondrocyte reprogramming via directly transactivating Sox9.

The present invention has identified the putative binding site for ATF4 on the Sox9 locus in hypertrophic chondrocytes of mice—a region in chromosome 11 (loci:

112642927-112643074) which covers the promoter region of Sox9 (FIG. 4B). It is thus possible to inhibit the transcription of Sox9 by using molecules that interfere with the entirety or part of the putative ATF4-binding site and thereby modulate conditions resulting from the overexpression of SOX9.

In one embodiment, the present invention provides a method of inhibiting the transcription of murine Sox9 by using a molecule that blocks or interferes with one or more binding sites for ATF4 on the murine Sox9 locus. In one embodiment, said ATF4 binding site is located within mouse chromosome 11 (loci: 112642927-112643074) having the sequence TGTTGCAA (SEQ ID NO: 1). In another embodiment, said ATF4 binding site is located within the binding sites for ATF4 as reported in Han: GTCACCCAAACAT-TTGCTTCCAAAAGACCAT-
TTCTAAGCACTTTTTTTGGAAGCCGGC
AGACTCCAGGCGCAGAAGCCCAGCTCCGCTTT-
GACGAGCAGCTGTTGCAATTTCCA
TTGCTGTAAACGCCAGCGAAGTCCCGGGTACCAC) (SEQ ID NO.: 2), the entire contents of which are incorporated herein by reference into this application (44).

In one embodiment, the present invention further provides a method of inhibiting the transcription of human SOX9 by using a molecule that blocks or interferes with one or more binding sites for ATF4 on the human SOX9 locus. In various embodiments, said ATF4 binding site is located within human chromosome 17 (chr17:68609000-71514000). In one embodiment, said ATF4 binding site is TGTTGCAA (SEQ ID NO.: 3) (38) which is the consensus sequence of ATF4 binding site on human SOX9 locus.

In various embodiments, various approaches including those described in Han (44) are used to identify the functional binding sites of ATF4 on Sox9/SOX9 or other related ATF4 potential downstream factors. In one embodiment, ATF4-binding sites on Sox9/SOX9 or other related ATF4 potential downstream factors are mapped by the core Amino Acid Response Element (AARE) sequence TTgCaTCA (SEQ ID: 4), which is the complementary strand of SEQ ID NO.1.

In one embodiment, open chromatin regions in cells expressing Sox9/SOX9 upon induction of the ISR and/or ATF4 over-expression is identified via ATAC-seq (39). This method applies hyperactive Tn5 transposase, which inserts sequencing adapters into accessible regions of chromatin, to mark accessible regions of DNA which are then sequenced. GFP (or other reporter) are inserted into 3' untranslated region of mouse or human locus and targeted so as to provide a readout of SOX9 activity, alternatively the cells derived from $Sox9^{EGFP/+}$ mice are adopted (40). Cells are subjected to ER stress, hypoxia or other stresses to induce the ISR, or over-expression of ATF4 is induced.

Three biological replicates for ATAC-seq are generated to identify enhancers that are active and distinct to the $So9^{+ve}/SOX9^{+ve}$ population. Approximately 10,000 FACS sorted $EGFP^{+ve}$ and $EGFP^{-ve}$ cells are isolated from $Sox9^{EGFP/+}$ mice and library are prepared via NEBNext High Fidelity 2×PCR Master Mix. The amplified libraries are purified by AMPure beads, quantitated (KAPA biosystems) and sequenced at 10-15 million reads.

Filtered reads are aligned to the mouse and human reference genomes using BWA and subjected to peak calling using MACS2. The regions with enrichment of transposition events indicating for open chromatin are identified. By comparing $Sox9^{+ve}/SOX9^{+ve}$ specific enhancer profiles, we are able to distinguish and capture putative ISR induced and/or ATF4-associated enhancers: a) those for driving Sox9/SOX9 expression under normal non-stressed conditions; and b) those active when the ISR is induced and/or ATF4 is overexpressed. This approach allows us to prioritize amongst the putative enhancers, not only for functional validation but also for generation of a regulatory map of ISR- and/or ATF4-associated Sox9/SOX9 enhancers.

To overcome variability in expression due to position effects, regions in the mouse genome or human genome that are constitutively open and therefore not subject to position effects are used for assaying the enhancer activity (e.g. the TIGRE locus (41, 105)). Reporter locus are targeted in cell lines and transgenic mice with a vector comprising a minimal promoter (such as hsp68 or the minimal SOX9 promoter which has no activity in cells/transgenic mice) linked by a 2A peptide sequence (42) to a fluorescence reporter (e.g. GFP, RFP, YFP etc.) or other factors (e.g. luciferase).

In one embodiment, the enhancer interference assay is used for functional validation of enhancer elements by epigenome inhibition in vivo and in vivo, using a nuclease-deficient Cas9 (dCas9)-histone demethylase (43) fusion to inhibit the activity of candidate enhancer(s) by selectively altering the chromatin state of the target enhancer(s). Removal of H3K4meI/me2 modifications from specific active enhancer(s) using targeted catalytically inactive dead-Cas9 (dCas9) fused to the lysine-specific demethylase 1 (KDM1A/LSD1) results in 'inactivation' of enhancer elements and down-regulation of gene expression from the associated loci. The transgene containing dCas9-LSD1 is targeted via using CRISPR-Cas9 (44), in which a guide RNA (gRNA) is specifically designed to direct LSD1 to the putative Sox9/SOX9 enhancer(s). In this way, the expression of LSD1 on targeting specific enhancer(s) silences the candidate enhancer(s) by demethylation of histone H3K4me2 and destruction of K27 acetylation (H3K27ac).

The targeted enhancer(s), resulting in loss of SOX9 driven EGFP expression when the ISR is activated and/or when ATF4 is over expressed, are first identified in vitro. In vivo, the activities of identified ISR- and or ATF4-inducible SOX9 enhancer(s) are assessed by: a) mutating the enhancer(s) in mice using CRISPR-Cas9; and b) targeting the enhancer(s) to the ISR reporter vector described above comprising a minimal hsp68 promoter and testing for its ability to be activated upon ATF4 or ISR induction in double transgenics where ISR is triggered and/or ATF4 is over-expressed.

Figure 13C:
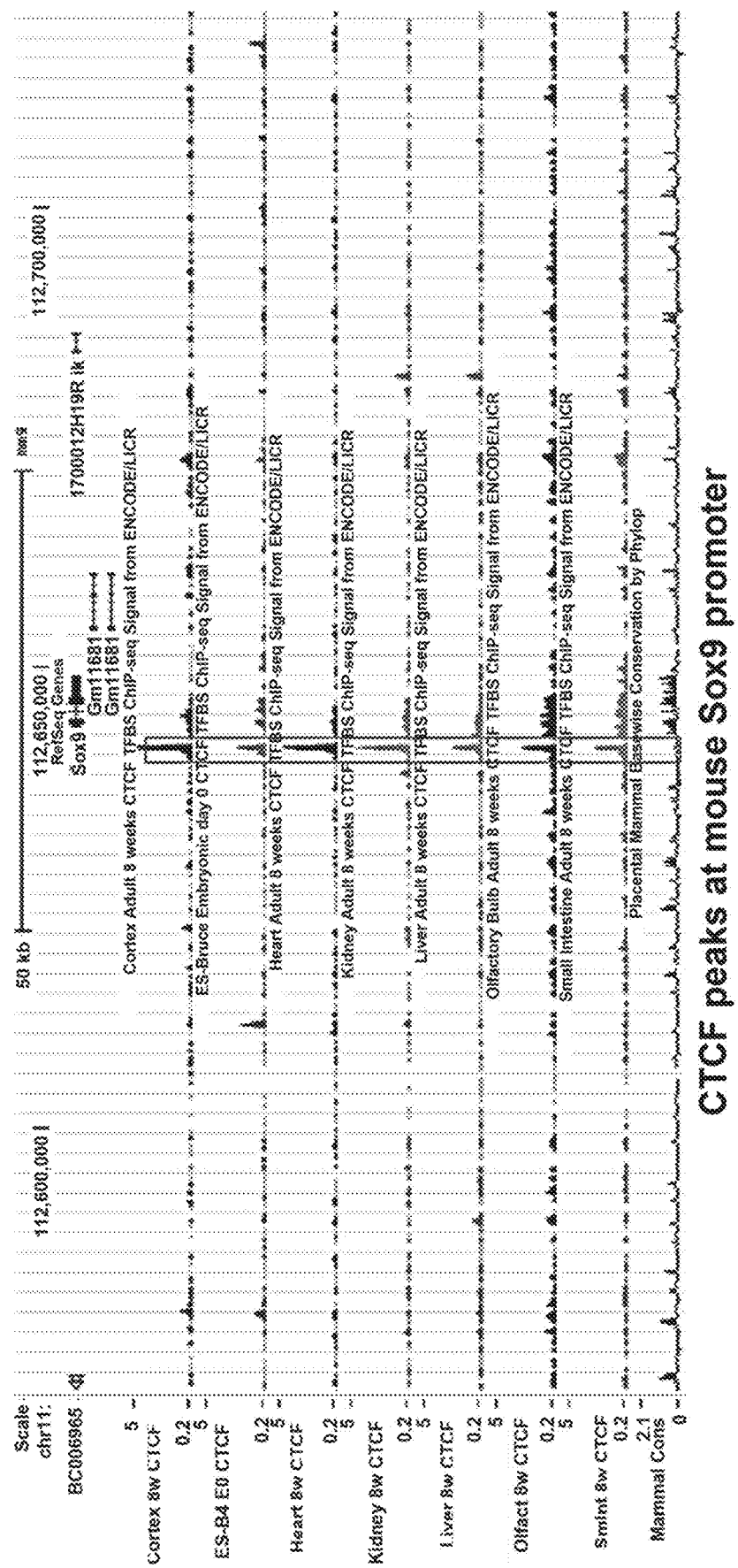

On the other hand, a total of 25 putative ATF4 binding enhancer regions were identified in the mouse Sox9-TAD domain (Table 1) by published ATF4 ChIP-seq (45), and FIG. 13C demonstrates an example of putative ATF4 binding enhancer region of mSox9. Taken together, these findings strongly suggest that ISR-induced ATF4 may regulate the Sox9 expression by enhancers.

In one embodiment, the present invention provides a method of inhibiting the transcription of Sox9/SOX9 (such as murine Sox9/Human SOX9) by using a molecule that blocks or interferes with one or more ATF4 binding enhancers which regulates the transcription of murine Sox9, said ATF4 binding enhancer comprises a sequence selected from the group consisting of SEQ ID NOs.: 5-29.

In another embodiment, the present invention provides a method of inhibiting the transcription of human SOX9 by using a molecule that blocks or interferes with one or more ATF4 binding enhancers which regulate the transcription of human SOX9. To identify the putative ATF4 binding enhancer regions in the human SOX9-TAD domain, ATF4 ChIP-seq is applied in human fibroblasts, cancer cell lines, and chondrocytes (or any other cell lines where stress induces SOX9*) differentiated from human iPS. The cells are treated with an ER stress-inducer such as tunicamycin (46) to activate the preferential translation of ATF4, and three biological replicates for each cell type are generated. In one embodiment, said ATF4 binding enhancers are located within human chromosome 17 (chr17:68609000-71514000).

In various embodiments, the present invention provides a method of inhibiting the transcription of human SOX9 by using a molecule that blocks or interferes with one or more ATF4 binding enhancers which regulate the transcription of human SOX9, said ATF4 binding enhancer comprises a sequence that could be similar/homologous to the murine sequence selected from the group consisting of SEQ ID Nos.: 5-29. In one embodiment, said ATF4 binding enhancer comprises a sequence corresponding to a sequence which is at least 70%, 75%, 80%, 85%, 90% or 95% homologous to the sequence selected from the group consisting of SEQ ID Nos.: 5-29. In another embodiment, said ATF4 binding enhancer in human comprises a sequence corresponding to and showing high consensus to the murine sequence selected from the group consisting of SEQ ID Nos.: 5-29. It is also possible that there will be human specific ATF4 binding enhancers not present in mouse. These will be detected by the ATAC-seq and ATF4 ChIP-seq approaches described above. Functional validation of the human enhancer activity will be tested by linking putative enhancer(s) to reporter (e.g. Luciferase/fluorescent proteins) constructs and testing for their activation upon inducing the ISR in vitro (mouse or human cell-lines) and in vivo, using transgenic mice in which the ISR is induced, such as in 13del.

TABLE 1

Putative ATF4 binding sites on murine Sox9 locus within Chromosome 11 in mice.

| ID | Start position | End position | Sequences | SEQ ID NO. |
|---|---|---|---|---|
| 1 | 111688769 | 111688869 | GAGTTGCCACAGCTTCCCTGGTGGTAGCACAGATGTTGTC TGGCAGACAGAGACAGAGGCTTACAGGACAGTCTCAAGA ACGACCAGAGTCAACCTGAACA | 5 |
| 2 | 111762751 | 111762851 | TACCCCCCAAAAATATAAAATAAAATCCCTTAGTCTAAA ATTCCATGCAATTAACATTGTTTACTTAAGGAGGAAGCTC TCCAGGACAATGTTCACATCTA | 6 |
| 3 | 111792806 | 111792906 | CAGTTCTTTCAGGAAGAAAAACAAACATTCCACTCAAAG TTAAAACTGAATTGTTTCCCATTTGAACAAATTATGACTT TTGATATATAATAGAGAAGACT | 7 |
| 4 | 111857540 | 111857640 | GGAAGTGGGGGTGGTGACAAAGGAGGTGGTAAGGGAGG GGAAATTGTGATCAGGATGTAACATAGGCGAGAATAAAT TCATAATGTTAACTAACAAAAAAA | 8 |
| 5 | 112003191 | 112003291 | CATCCAGAAGGACAATGTCAACATCTAGCCTCAGCATGT GGTCACTGAGACTTCCCACAAGGATTTGATATTTTTAACA TTACCAAAGCACGGTACACAAC | 9 |
| 6 | 112063301 | 112063401 | TTCAACCTTGTACAACTCCAGACTCGGTGACTCTAGACAC AGTAGGAGAGAAGGAAACTAAAGAAGAGTGTGGGAAGC TTACATGCTCACATTCTGACCCA | 10 |
| 7 | 112472513 | 112472613 | ACAGCCATTTCCTCCTTAGCTGCCTCCTACAAAACATCAC ACCCTGGCCTCCATCCTCAGCCCAGTGCCAGGCCCATCAT TGGGGAAGACACCGCACTTCC | 11 |
| 8 | 112546494 | 112546594 | AGTGACAGAGAGTGTCAGGATGTGATGGGGCCTCCAGTG ACCACCTCGCTCACCCGGGAACTTTCCAAATGTCACACAT AAACCCTCTCACTAATTAGCTG | 12 |
| 9 | 112608916 | 112609016 | GAAGAATGCAGGCAAGAAACATAGGAGAGAAGCACTCC TGAATGGAGCCTTCCCGCTCAGAGAGCAATTGTTGCTGCT CACTCTTTTGGAGCTCAACAAAC | 13 |
| 10 | 112613540 | 112613640 | ATTAAATAAAGTTGTAATGATGGCGTTTTGATCCAACAGG CCTCTTTTTTTTTAAATATTTTTATTATTATGTATTTTCCTC AATTACATTTAGAATGCTA | 14 |
| 11 | 112638971 | 112639071 | CCTGAGAGCTTTTCAGACTCAATTATCCCTAAAGCCATAA TGAGAACTGCATCATGGAAAGGAGACTTGGACCCTATGA CATGCAGTAACAAAGAGTCTGC | 15 |
| 12 | 112662091 | 112662191 | CCTTTGCAGATGAAGTAATACACAATCCTGGAAGGTGCA CTAAAAATCCTAGGAAGAAGACAGAGTGATTCAGCCTGA ATATTGAGAAGAGAATCCAGGGA | 16 |
| 13 | 112782311 | 112782411 | AAGAGAGACGAGGTGCAAGTGGCCCCGGTTTCGTTCTCT GTTTTCCCTCCCTCCTCCTCCGCTCCGACTCGCCTTCCCCG GGTTTAGAOCCGGCAGCTGAG | 17 |

TABLE 1-continued

Putative ATF4 binding sites on murine
Sox9 locus within Chromosome 11 in mice.

| ID | Start position | End position | Sequences | SEQ ID NO. |
|---|---|---|---|---|
| 14 | 112805430 | 112805530 | GTCCTTCTTTCTTATTATGGCTGAGGGCTCCAGCCCATCTC TACTTAGAACCACATCCAGCGCATCTCTCATTCCACTCCT CCCCTGTTCTCTCAGTCTCC | 18 |
| 15 | 112837797 | 112837897 | TACACACAAACATATACATACATACACATACATCTTTACA CACATATGTACAAACACACACCAAACACATCCACCACAA TAAATATTTTAAGTTGAAAAGT | 19 |
| 16 | 112849357 | 112849457 | GGGTTTTCTATAAGAGCACTGCATGCTTTAAACCAGAGA GTCCTCTTTCTGTTTCTTCTTTCGTTTTCTAAGAATGAATC TCATGTACCCCAGGCTGACTT | 20 |
| 17 | 112925650 | 112925750 | GTAATTCTTTGACTCTTGACTTCTTGGGATAGCATGCTTG ATAATGATCAAAGCAGCAAACAGACCTGGTTAGGAAAAT GGCCGTTCTCCCTTCCACTGCT | 21 |
| 18 | 112958017 | 112958117 | CTCACATGGTGTTCCCCGGTAGGAGGAATGGCATGGCTG CCTCTACATAAATGCAGGGGGTTGGGAGGGTGCAAGGG CATCTCCTGAAGGAGGACCTGCT | 22 |
| 19 | 113297871 | 113297971 | TCCCAAAGGATGGGATTATAGGTCTATGCCACCACATGC CCCCTGGGCGCTGATTTTTGATCCCTGCCACTGATCCAGT AGGACACTGAGGTGCAGTAGCA | 23 |
| 20 | 113538311 | 113538411 | GCTTCTACTCAGTTGCAATAAGACCTTTAGGCTGATTTTA ATAGAGGGCAATACAAATAAAGTCGCAATTAATATTCCT ATTCAGTTTCTTAAAAGAAATA | 24 |
| 21 | 113568366 | 113568466 | TCTCAGCTCCTCCTGCGCCATGCCTGCCTGGATACTGCCA TGCTCCCACCTTGATGATAATGGACTGAACCTCTGAATCT GTAAGCCAGCCCCAATTAAAT | 25 |
| 22 | 113609981 | 113610081 | AAAAAAAAATAGAGAGAGGTGCCTGTGCGCCATTTAC AACACATTTAAGTAAATCAATAGGAAAAAAATAGCAGAA ATAATTAGAATTGCCTGTCCTTG | 26 |
| 23 | 113671192 | 113671292 | TCAGTGCTCTTACCCGCTGAGCCATCTCGCCAGCCCTCAA CATTTTTAAAATTATGCCCAACTTGGAGCTGGAGAGATGG CTCAACAGTTAAGAGCACTGG | 27 |
| 24 | 113910532 | 113910632 | TGGGTGGCTTGTGTGAAGCCTGCCCTGAGCCTTTTAAAAA TTATACTTTGTATTCATTTCTTTGTGTACGTGTGCACGTGT GTGAGGTCAGAGGACAAGTC | 28 |
| 25 | 113926715 | 113926815 | TACTTTTGTGTGTGTGTGTGCGTGTACATGTGTGCACA TGCATGCTCACTTAATTGACTTTCATTATGCTTGTGAGGG GTTGTTTATCAGCTCATTGAT | 29 |

Drug Screening Platform Using 113Del and 13Del-KI Transgenic Mice

The third aspect of this invention is to provide a method of screening a candidate molecule for the ability to modulate a skeletal disorder or its phenotypes associated with ISR involving the p-eIF2α pathway using transgenic mice disclosed in the present invention.

In one embodiment, the present invention provides a method of screening a candidate molecule for the ability to modulate a skeletal disorder or skeletal abnormalities associated with ISR involving the p-eIF2α pathway, comprising the steps of administering said candidate molecule to a transgenic mouse carrying a Col10a1 transgene or having a DNA sequence encoding the mutated collagen protein Col 10-13del, and expressing a phenotype lacking hyperostosis. In one embodiment, the transgenic mouse represents a direct equivalent model of human 13del MCDS mutation. In one embodiment, the transgenic mouse is 13del mice or 13del-KI mice.

In embodiment, the present screening method further comprises a step of detecting any changes in the mouse that indicate improvement of said skeletal disorders or skeletal abnormalities including but are not limited to disproportionate dwarfism, short stature or limbs, flaring of metaphyses, genu varum (bowing legs), coxa vara, hip deformation, platyspondyly (flat vertebral bodies), abnormal vertebral endplates, widen growth plate and disc degeneration.

In one embodiment, the present screening method comprising the step determining one or more of the following parameters in the mouse treated with said candidate molecule and comparing the results with those from a positive control such as ISRIB and a negative control:

a) the growth curve, including body trunk length and whole body length, during whole period of treatment;
b) limb length, including individual limb bones, after treatment;
c) the spine length and curvature after treatment;
d) the angle between proximal head and distal head of tibia after treatment;
e) pelvic bone orientation (the angle between ilium and pubis) after treatment;

f) the angle between the proximal head and the shaft of the femur after treatment;
g) the heights of growth plates from limb bone and spine;
h) the onset time point of disc degeneration after preventive treatment (administration before IDD observed);
i) the X-ray examination and MicroCT examination of IDD development during the preventive treatment (administration before IDD observed);
j) the X-ray examination and MicroCT examination of IDD development during the therapeutic treatment (administration after IDD observed);
k) the disc histological morphology after or during the preventive (administration before IDD observed) and therapeutic treatment (administration after IDD observed), including the heights of growth plates, the irregularities of endplates, the volume of vascular canals in subchondral region between spinal growth plate and endplate, the disc distance and the calcification of nucleus pulpous (NP);
l) the expression and transcription level of ectopic expressing factors, such as Sox9 in the affected disc after treatment;
m) the cell number of ectopic expressing factors, such as Sox9 in the affected disc after treatment;
n) the expression and transcriptional level of affected factors, such as Col10a1 in the affected disc after treatment;
o) the number of affected factors expressing cell, such as Col10a1 in the affected disc after treatment; and
p) the number of apoptotic cells in the affected disc after treatment.

Discussion

In a transgenic mouse model displaying phenotypes reminiscent of congenital dwarfism [Metaphyseal chondrodysplasia, type Schimd (MCDS), MIM156500] and intervertebral disc changes consistent with early stages of human intervertebral disc degeneration (IDD), it has been shown that synthesis of misfolded collagen X in hypertrophic chondrocytes causes abnormal intracellular retention of secreted proteins and triggers the unfolded protein response (10). Specifically, it has been found that the PERK pathway, which controls protein translation via eIF2α phosphorylation and induction of the transcription factor ATF4, causes the hypertrophic chondrocyte differentiation defect in the growing long bones and spine. In one embodiment of the present invention, ISRIB, a selective modulator of phosphorylated-eukaryotic initiation factor (p-eIF2α) and eIF2B complex, is used to prevent and/or ameliorate the dwarfism and intervertebral disc degeneration caused by induction of the integrated stress response pathway.

Figure 2A:
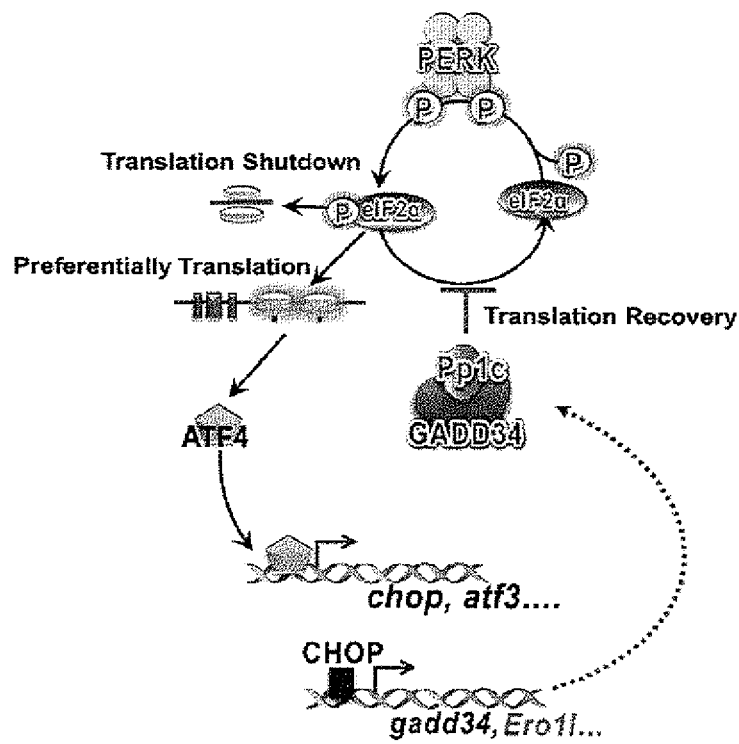

As shown in FIG. 2A, activation of PERK signaling pathway leads to eIF2α phosphorylation, which represses the global protein translation but preferentially facilitates the translation of ATF4 transcripts via bypassing an inhibitory upstream open reading frame (uORF) (47). ATF4 can trans-activate Chop and ATF3, and form a heterodimer with ATF3 to modulate the expression of target genes, such as GADD34. CHOP also acts upstream of GADD34, which encodes a regulatory subunit of the protein phosphatase complex that dephosphorylates p-eIF2α and restores protein translation. Thus ATF4, CHOP and GADD34 form a negative feedback loop to ensure transient attenuation of protein synthesis and later recovery of protein translation during ER stress response (13, 47).

It is observed in the present model that UPR plays a critical role in the pathogenesis of MCDS. The present invention identifies the mechanism(s) underlying the ER stress-associated skeletal defects in the MCDS model. The present invention further discloses a novel approach in preventing or treating ISR-associated diseases, in particular to diseases where aberrant cell differentiation is the underlying cause.

This invention will be better understood by reference to the examples which follow. However, one skilled in the art will readily appreciate that the examples provided are merely for illustrative purposes and are not meant to limit the scope of the invention which is defined by the claims following thereafter.

Throughout this application, it is to be noted that the transitional term "comprising", which is synonymous with "including", "containing" or "characterized by", is inclusive or open-ended, and does not exclude additional, un-recited elements or method steps.

UPR Disrupts Transcriptome Patterns in the Chondrodysplastic Growth Plate

Figure 2B:
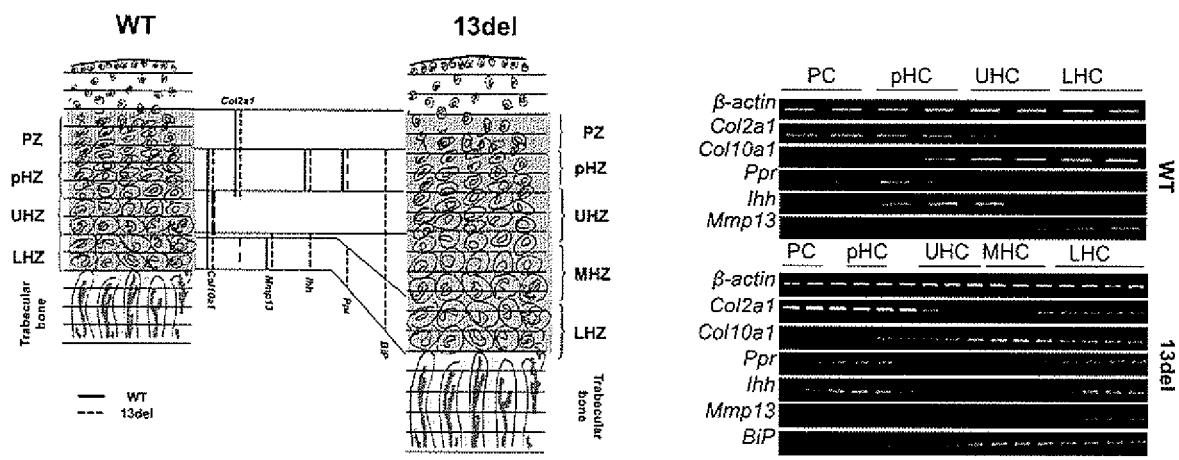
Figure 2C:
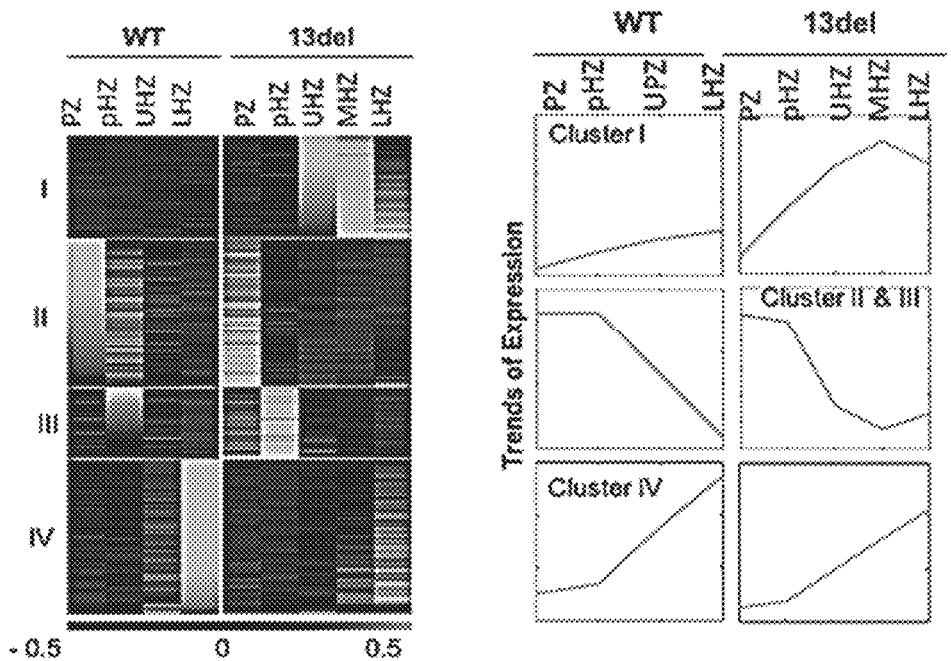
Figure 2D:
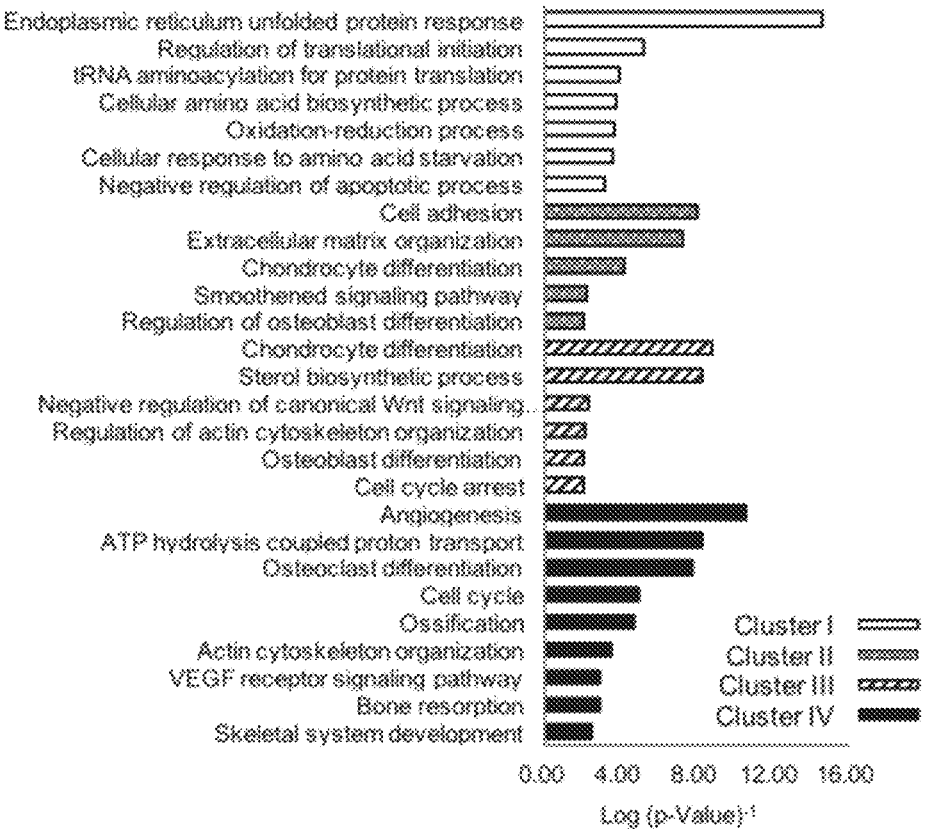
Figure 2E:
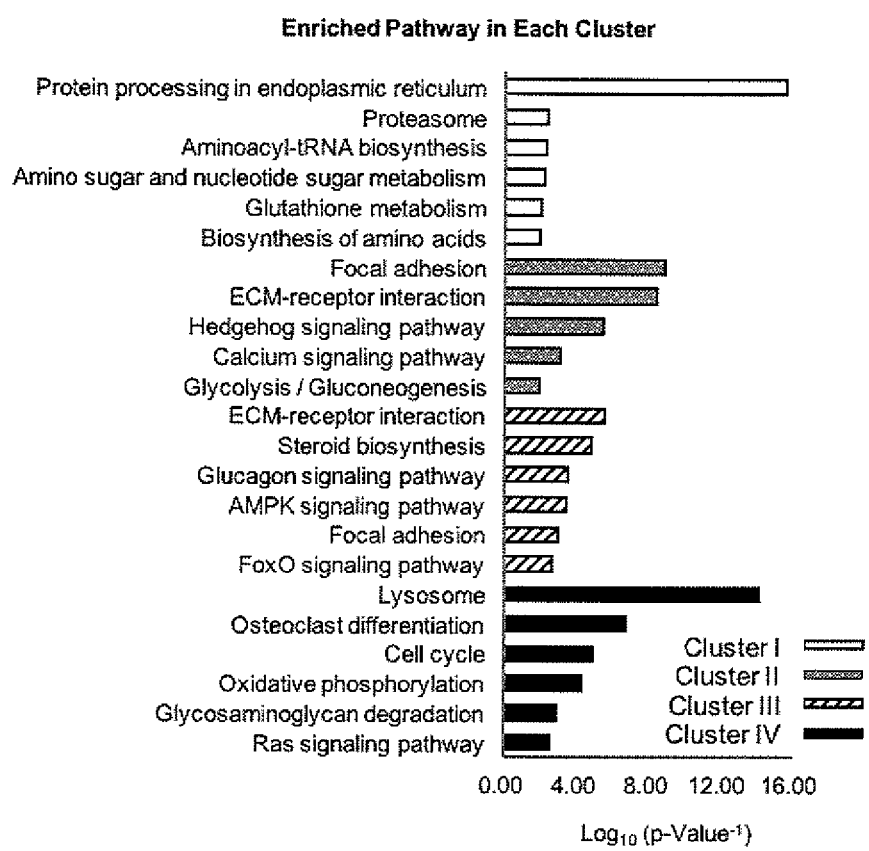

The mammalian growth plate comprises four major sub-populations of chondrocytes organized into zones: resting, proliferating (PZ), prehypertrophic (PHZ) and hypertrophic (HZ). These chondrocytes have distinct morphologies and gene expression profiles governed by a precisely tuned gene regulatory network (48). To investigate the effect of the UPR on transcription, chondrocytes in the proximal tibia growth plates of postnatal day 10 (p10) from wild-type and MCDS 13del mice were fractionated into sub-populations representing proliferating, prehypertrophic and hypertrophic chondrocytes (HC) (FIG. 2B). The wild-type HZ was fractionated into upper and lower zones (UHZ and LHZ) to capture early and late phases of hypertrophy. The 13del HZ was fractionated into three zones: upper, corresponding to early phase of UPR activation, middle (MHZ), where HC adaptation would be initiated, and lower, where HC should be fully adapted.

k-means clustering was used to categorize the gene expression patterns across different zones in wild-type and 13del growth plates into four clusters. Genes (453) in Cluster I increased expression from PHZ to lower HZ specifically in 13del HC (FIG. 2C). Ontological analyses show these differentially expressed genes are mainly involved in protein processing in the ER and the UPR (FIGS. 2D and 2E). Genes in Clusters II (659) and III (314) showed highest expression in wild-type PZ and PHZ followed by progressive down regulation from PHZ to lower HZ, but were upregulated in 13del lower HZ, reflecting UPR induced changes (FIG. 2C). These genes included Sox9, Ppr and Ihh, consistent with the previous report of re-expression of pre-hypertrophic markers (10). Cluster IV genes (680) showed increasing expression from PHZ to lower HZ in wild-type and can be defined as "HC characteristic" genes. Consistent with a change in the HC differentiation state in 13del, these genes were down-regulated in 13del lower HZ. The concomitant down-regulation of Cluster I stress response genes in 13del lower HZ is consistent with alleviation of the stress in the reprogrammed cells and an adapted state.

PERK Signaling is the Major Contributor to Chondrocyte Adaptation to ER Stress

The UPR employs three arms of sensors in the ER to mediate cell adaptation and survival under ER stress: PERK, IRE1α, and ATF6 family (49-51). Upon ER stress, ATF6 family factors move from the ER to the Golgi, are processed by S1 and S2 proteases, and translocate to the nucleus to activate ER quality control genes such as Hspa5 (encodes BiP) and Xbp1 (X-box binding protein 1). IRE1α has kinase and endoribonuclease (RNase) activities. It catalyses the splicing of Xbp1 mRNA, generating the UPR transcription factor XBP1$^s$ that upregulates genes encoding chaperones and proteins involved in ER-associated protein degradation (ERAD).

PERK phosphorylates serine 51 in eIF2α, promoting the formation of a p-eIF2α and eIF2B complex, consequently inhibiting the guanine nucleotide exchange activity of eIF2B (52). Inactivation of the eIF2 complex leads to shut down of protein synthesis except for certain proteins, including ATF4, CHOP and other factors with both pro-survival and pro-death functions (47). eIF2α phosphorylation is transient and is reversed by GADD34, the regulatory subunit of eIF2α phosphatase, acting in a negative feedback loop, allowing protein synthesis to restart. When the stress is intense or prolonged, cells fail to adapt and apoptotic cell death is triggered. This PERK-p-eIF2α/ATF4/CHOP modulation of mRNA translation is a central part of the more general ISR (18).

Figure 2F:
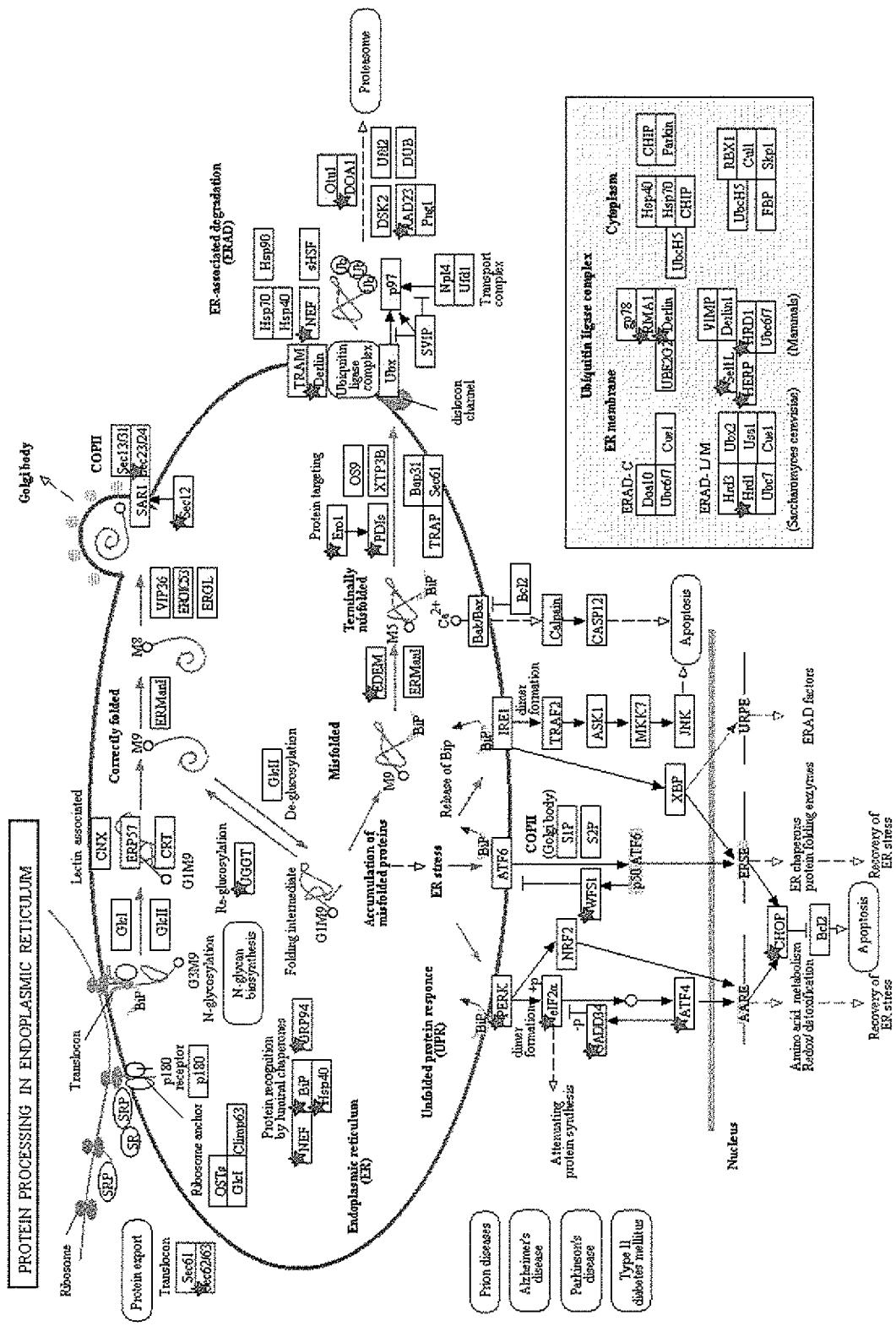
Figure 2G:
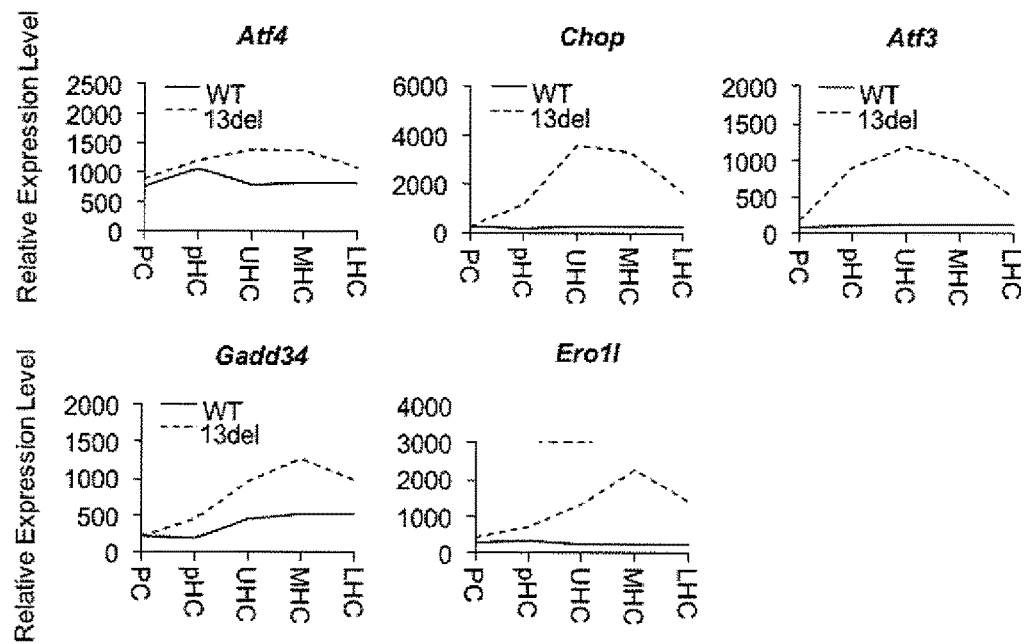
Figure 2H:
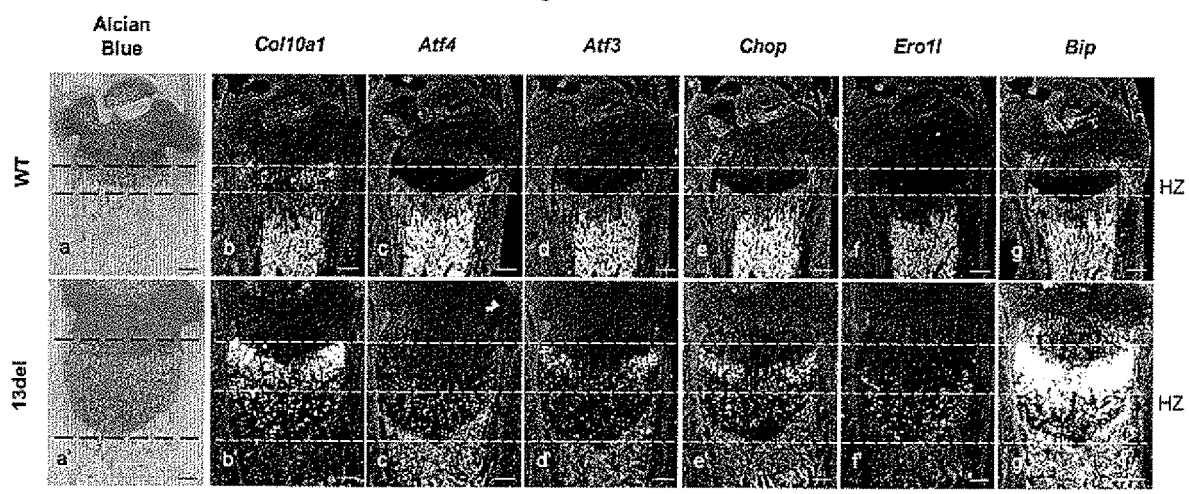
Figure 2L:
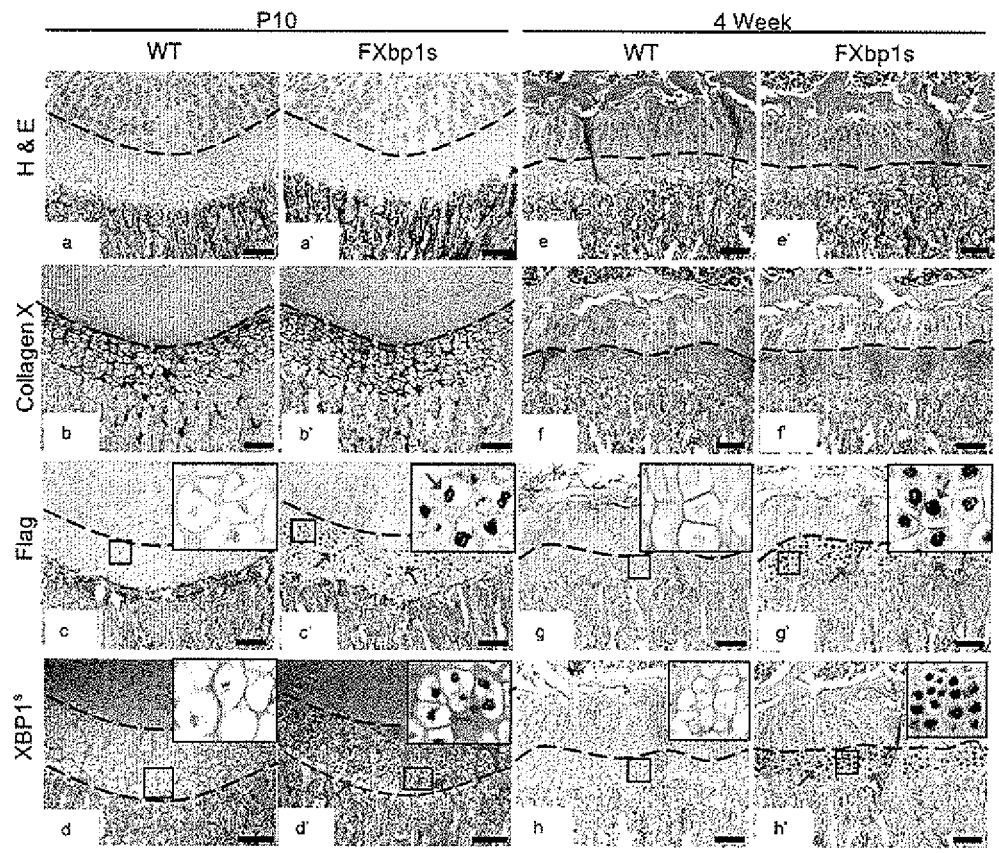
Figure 2M:
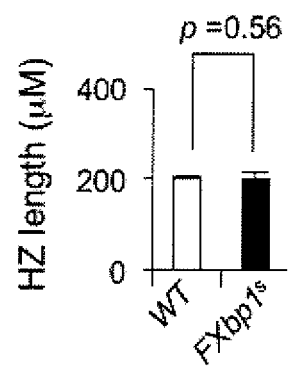

Contributions of PERK, IRE1 and ATF6 to the HC response to ER stress were investigated. By ontology and pathway analysis of Cluster I, enrichment of genes in the PERK pathway and IRE1-XBP1$^s$ regulated ERAD was found, but not for ATF6 signaling (FIG. 2F). Activation of PERK signaling in 13del HC was demonstrated by up-regulation of its key components (Atf4, Atf3, Chop, Ero11 and Gadd34) (FIG. 2O) which was validated by in situ hybridization and immunostaining (FIGS. 2H and 2I). Using Motif enrichment analysis, it was found that the binding motifs of CHOP and ATF4 were highly enriched in Cluster I, but not those for XBP1 or ATF6 (FIG. 2J). By interrogating ATF4 and CHOP ChIP-seq data (45), significant over-representations of ATF4 (odds ratio-2.87, p<0.0001) and CHOP (odds ratio=4.33, p<0.0001) binding peaks associated with the genes from Cluster I were observed but not for the other clusters. Cluster I genes are therefore those most likely to be directly regulated by PERK-associated transcription factors.

Together, these data suggest a prominent contribution of the PERK signaling pathway. To test this notion, Xbp1$^s$ was ectopically expressed in HC in transgenic mice (FIG. 2K). Over-expression of XBP1$^s$ specifically in HC did not affect the growth plate (FIGS. 2L and 2M), which is consistent with another MCDS mouse model study that found inactivation of Xbp1 in chondrocytes did not alter the severity of dwarfism (53).

ATF4 Expression in Hypertrophic Chondrocytes Reprograms Differentiation

Apart from its role in the UPR, ATF4 also regulates chondrocyte differentiation through activating Ihh (54). ATF4 is normally expressed in fetal growth plate chondrocytes, but not in HC by p10 (FIG. 3A). Therefore, the chondrocyte differentiation defects in the MCDS model might be directly caused by activation of ATF4 and/or its target Chop.

Figure 3B:
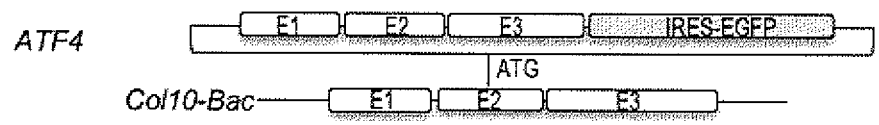
FIG. 3B refers to scheme of Atf4 expression vector. Atf4 cDNA is inserted after the ATG codon in exon 2 of the Col10a1-Bac together with an IRES-EGFP cassette.
Figure 3C:
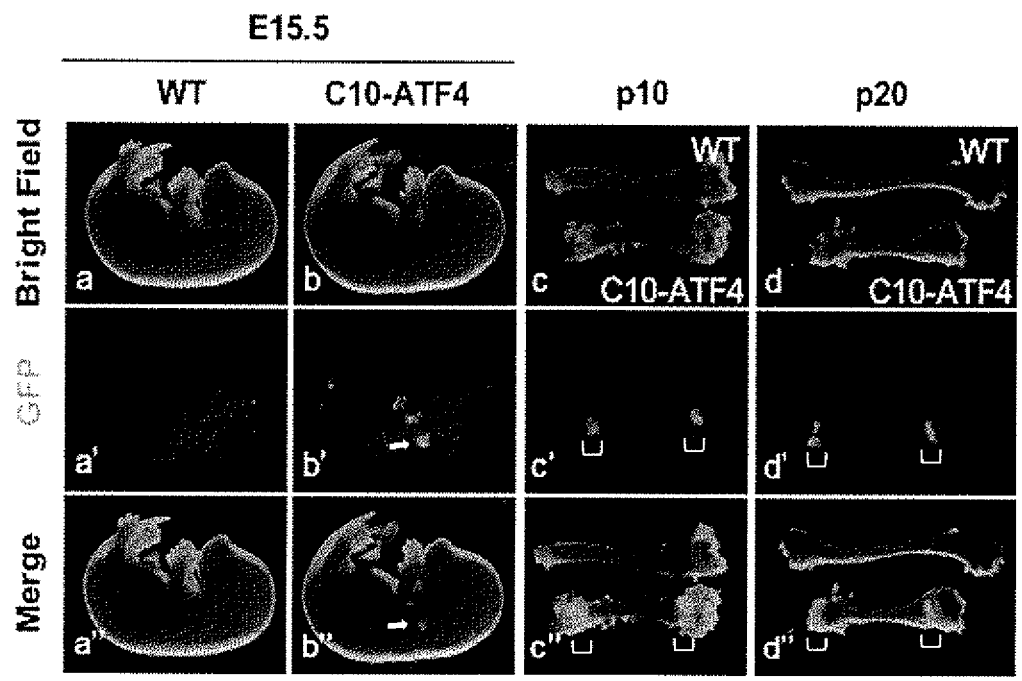
In FIGS. 3C and 3D, expression specificity of C10-ATF4 transgene was determined by EGFP visualization in developing growth plates (FIG. 3C), and validated by expression profiling of Egfp (a, c, e and g) and Atf4 (b, d, f and h) in C10-ATF4 growth plates at different stages (FIG. 3D).
Figure 3D:
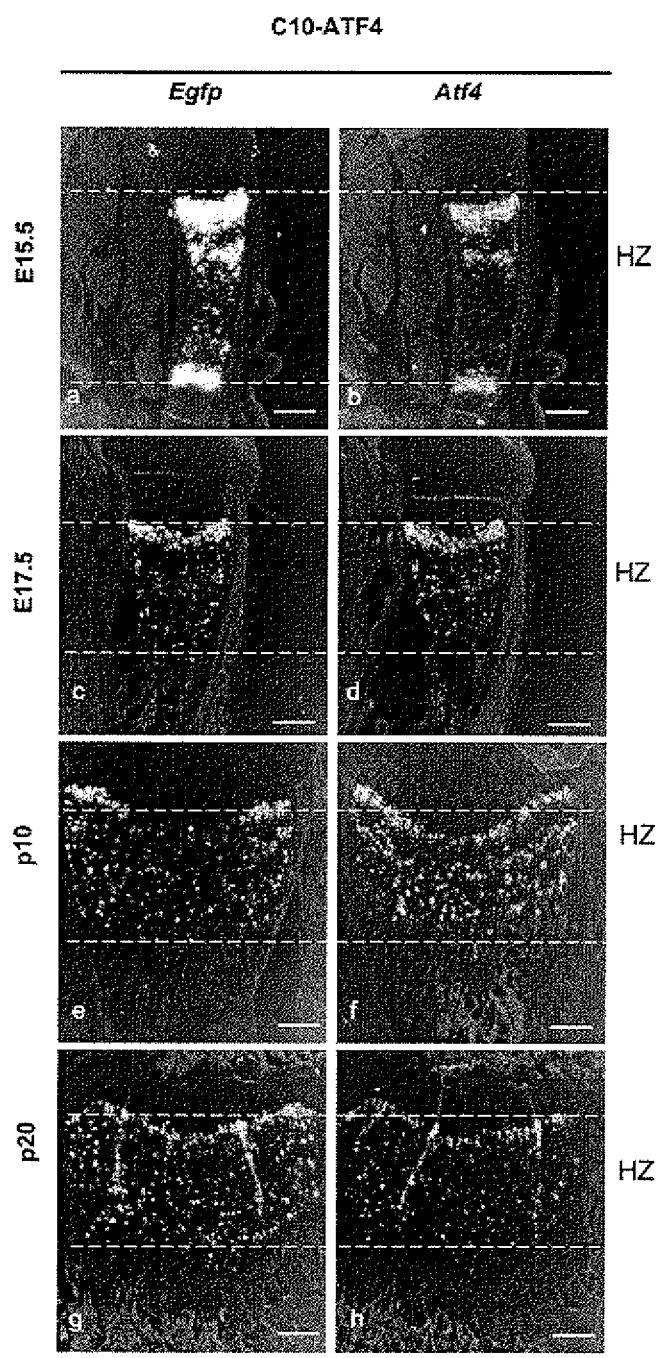
Figure 3E:
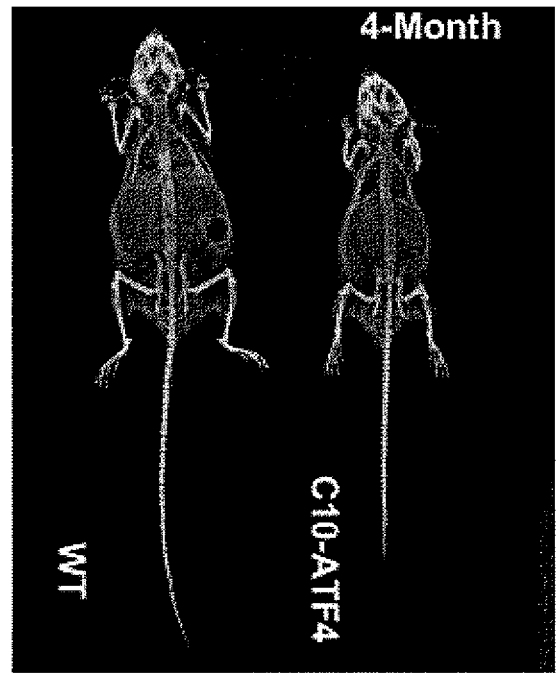
FIG. 3E show the radiographic analysis which revealed the dwarfism and skeletal abnormality of C10-ATF4 mice at 4-month-old.
Figure 3F:
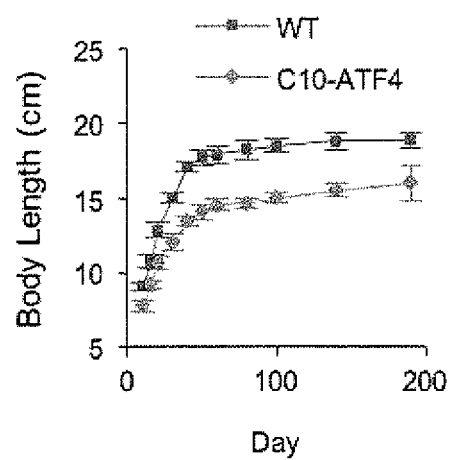
FIG. 3F illustrates that body lengths of the WT and C10-ATF4 littermates were monitored from birth to 6-month stage, and a consistent reduction of body length in C10-ATF4 mice was observed.
Figure 3G:
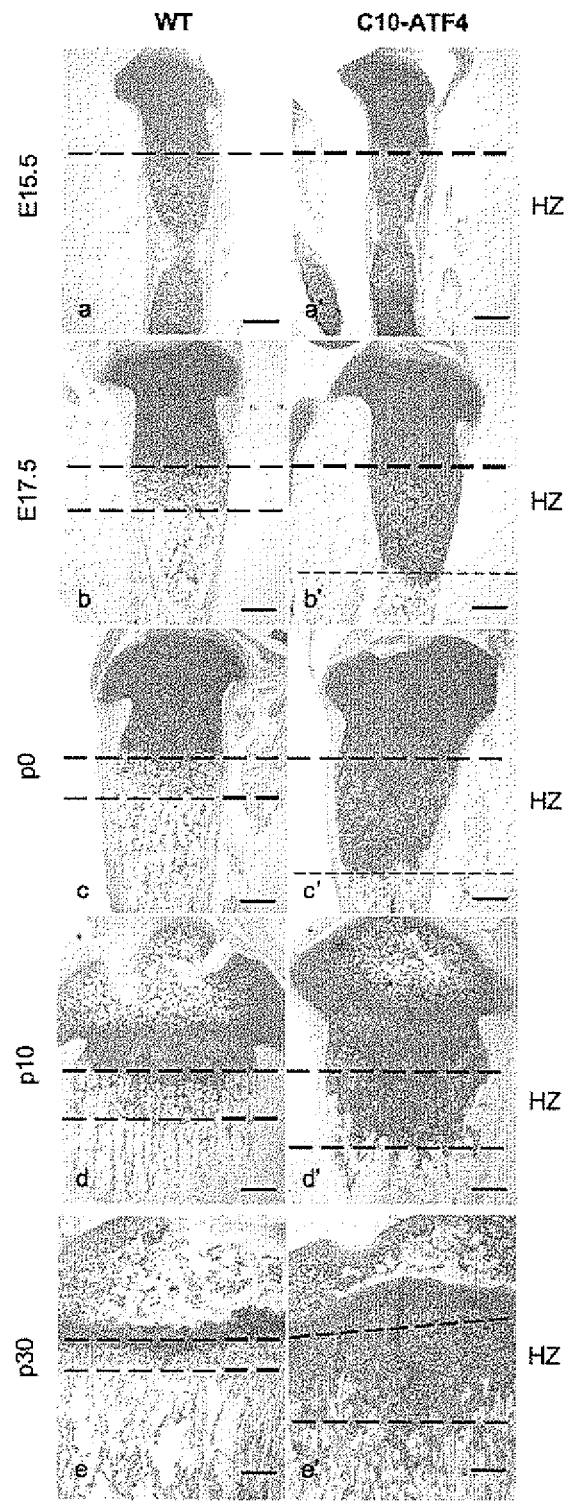
In FIG. 3G, abnormal proximal tibial growth plates with expanded HZ, delimited by dotted lines, were observed in C10-ATF4 mice.
Figure 3H:
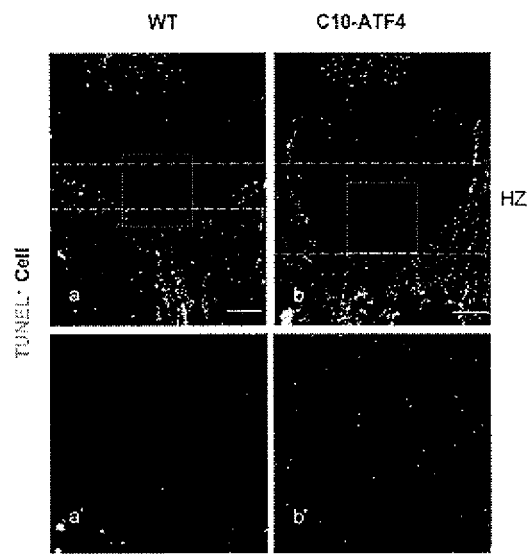
FIGS. 3H-3I show ectopic expression of ATF4 in HCs leads to dwarfism and HZ abnormality.
Figure 3I:
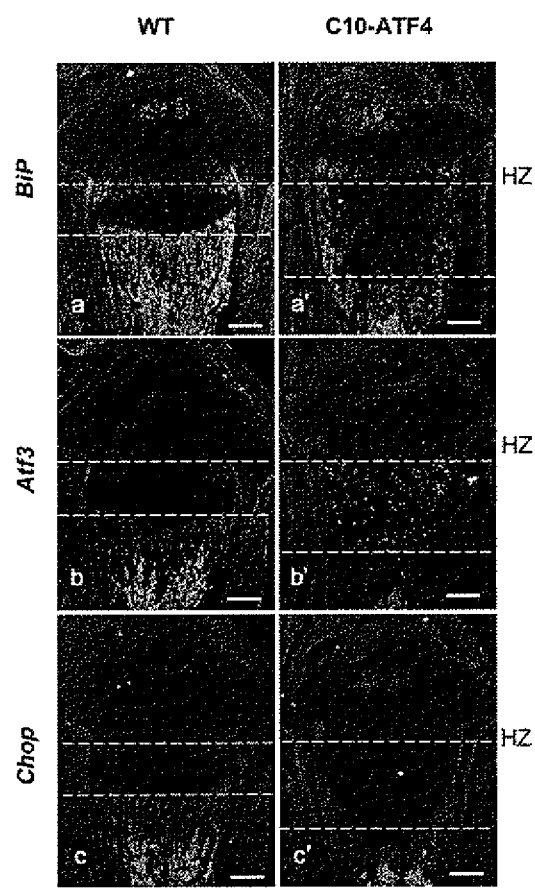

To dissect apart the contribution of ATF4 to aberrant HC differentiation in the absence of ER stress, a transgenic mouse model carrying a Col10-Bac-ATF4-IRES-EGFP transgene was generated (hereafter referred to as C10-ATF4) (FIG. 3B), in which ATF4 expression was driven by the highly HC-specific promoter of Col10a1(55, 56). The present invention confirmed HC-specific expression of the C10-ATF4 transgene in the developing growth plates from fetal (E15.5) to adult (P20) stages (FIGS. 3C and 3D). Similar to 13del mice, adult C10-ATF4 transgenic mice were dwarfs, being approximately 20% shorter than wild-type littermates (FIGS. 3E and 3F). Histological analyses revealed a greater than three-fold expansion of the HZ in C10-ATF4 mice (FIG. 3G). Although forced expression of ATF4 in fibroblasts was reported to decrease survival (45), cell viability was not affected in C10-ATF4 mice (FIG. 3H). Importantly, overexpression of ATF4 in HC in the absence of ER stress, did not induce transcription of the UPR-associated genes Bip and Chop (FIG. 3I), although Atf3 was slightly upregulated (45). Therefore, activation of ATF4 alone, in the absence of the ER stress response, is sufficient to alter HC differentiation, disturb endochondral ossification and cause skeletal abnormalities similar to those observed in 13del mice.

ATF4 Reprograms Chondrocyte Hypertrophy by Directly Activating Sox9

In C10-ATF4 HC, constitutive ATF4 activation down-regulated expression of Col10a1, and led to expression of prehypertrophic chondrocyte marker genes Sox9, Col2a, Ppr and Ihh in the lower portion of the HZ (FIG. 4A). The sequential differentiation process in growth plate chondrocytes is tightly regulated by multiple chondrocyte-specific transcription factors that control expression of cell type-specific genes and secreted growth factors (48, 55, 57-61). The present invention searched published ER stress-associated ATF4 ChIP-Seq data (45) for binding peaks in key chondrogenic transcription factor genes, including members of SOX, RUNX, MEF2, GLI and FOXA families, and found ATF4 binding peaks in regulatory regions of Sox9, Sox5, Sox6, Runx2, Gli2 and Gli3. Amongst these, only the Sox genes were up-regulated in 13del middle and lower region HC (FIG. 4B), suggesting that the Sox family could be the regulatory targets of ATF4.

Figure 4C:
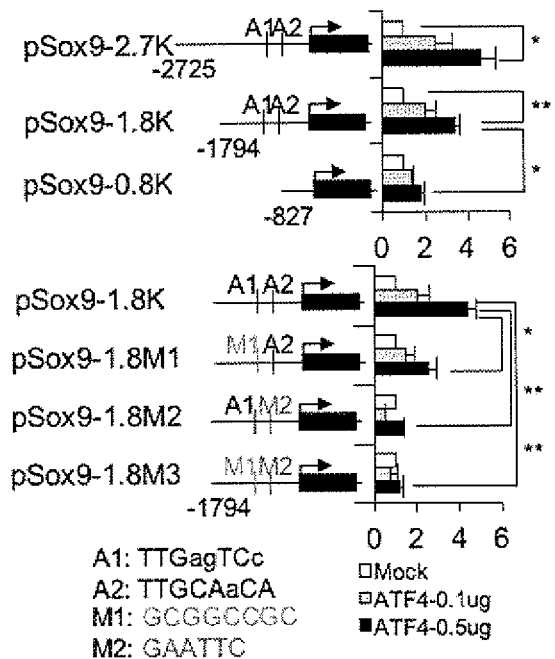
Figure 4D:
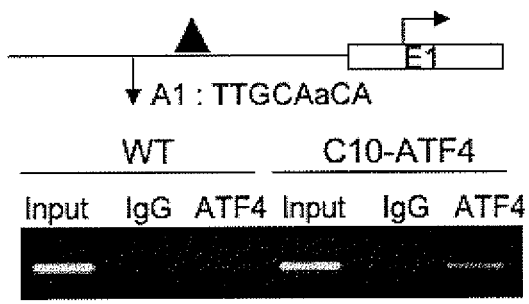

SOX9 is highly expressed in immature chondrocytes, transactivates critical cartilaginous matrix genes and regulates chondrocyte proliferation, differentiation and hypertrophy (55, 60-63). It is required for the expression of SOX5 and SOX6, which cooperate with SOX9 to transactivate Col2a1 (61). Two putative C/EBP-ATF4 motifs, named A1 and A2, were identified in the Sox9 promoter region covering the ATF4 binding peak. By transfection assays in ATDC5 chondrocytic cells, it was found that ATF4 could transactivate luciferase reporters controlled by motif-containing Sox9 promoter (FIG. 4C). Mutation of A1 and A2 respectively reduced or abolished ATF4 activation of the Sox9 reporters (FIG. 4C). Anti-ATF4 ChIP-PCR assays, using nuclear extracts from E15.5 wild-type and C10-ATF4 limbs, demonstrated that ATF4 binds directly to the putative motifs region on the Sox9 promoter in vivo (FIG. 4D).

Figure 4E:
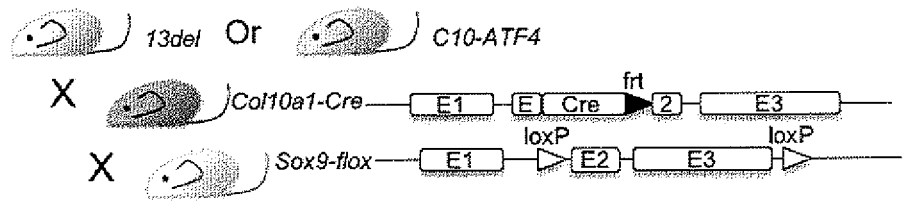
Figure 4F:
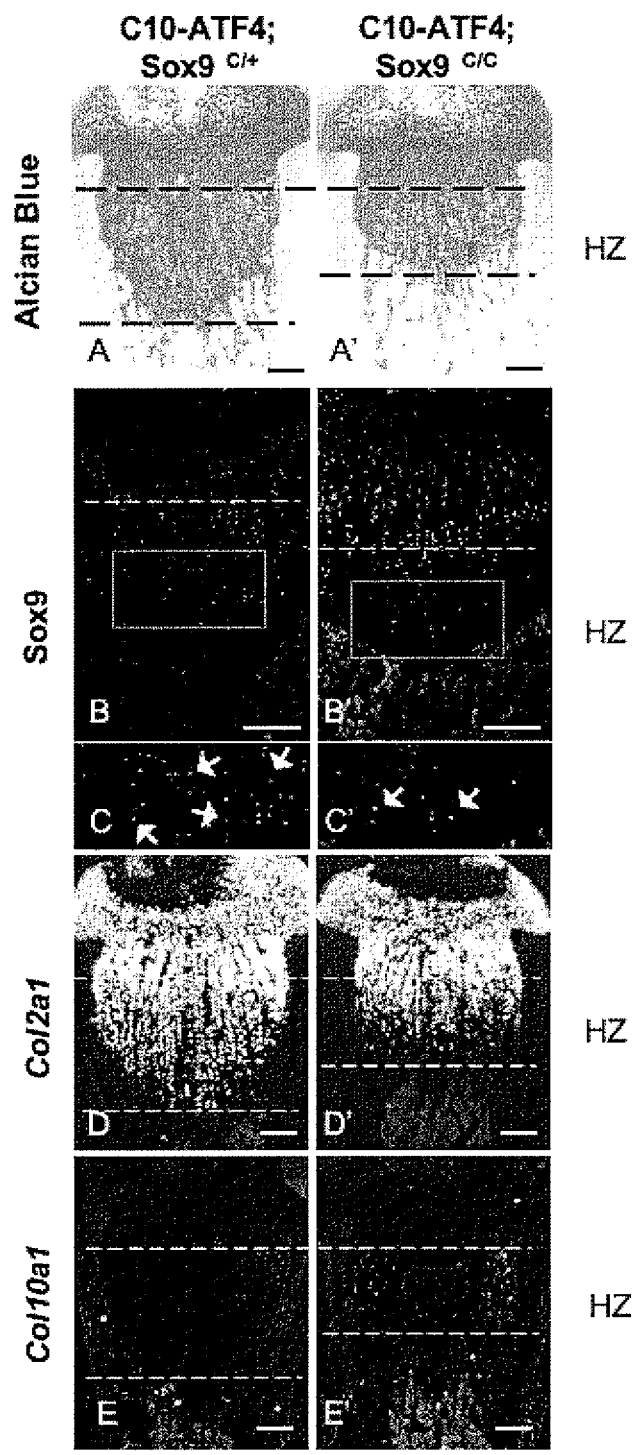
Figure 4G:
Figure 4H:
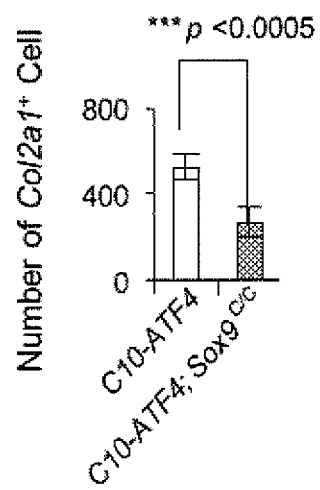
Figure 4I:
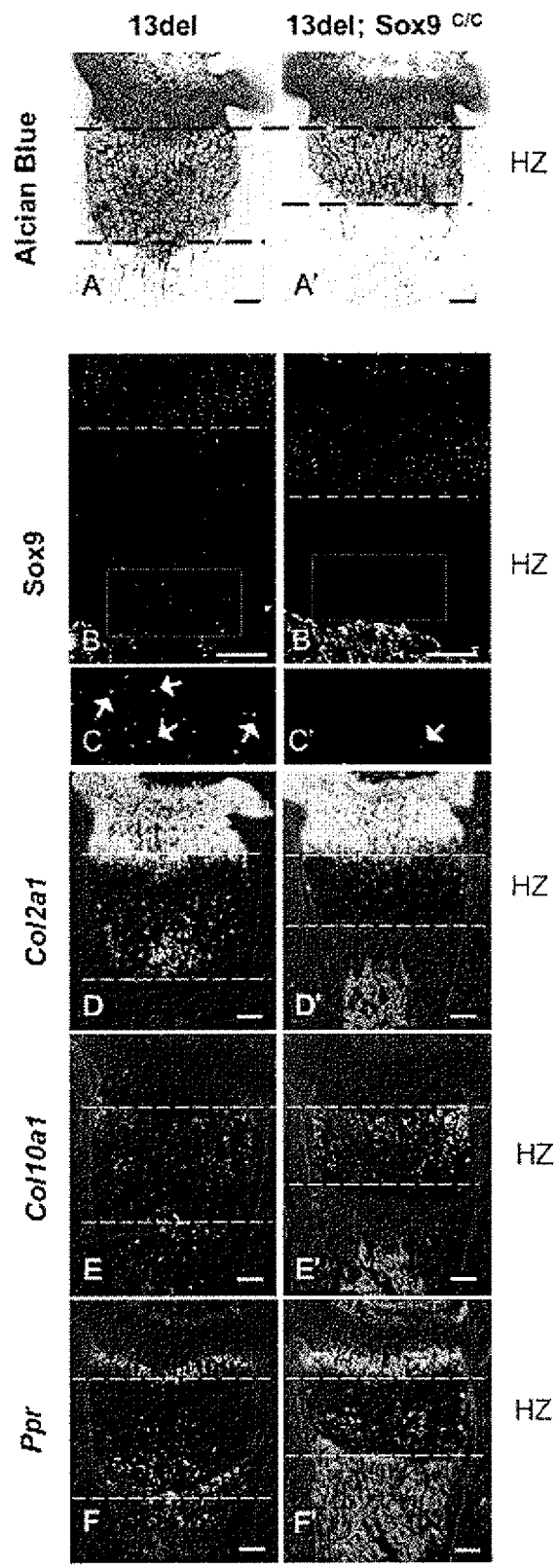
Figure 4J:
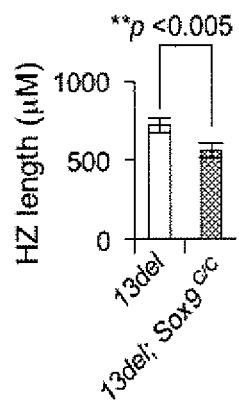
Figure 4K:
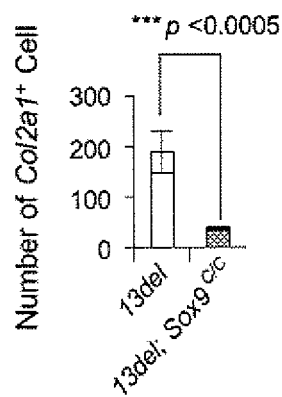
Figure 4L:
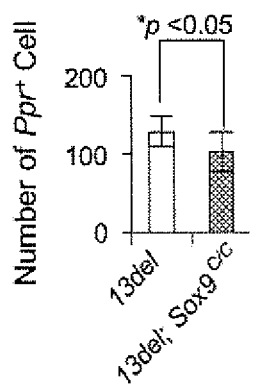
Figure 4M:
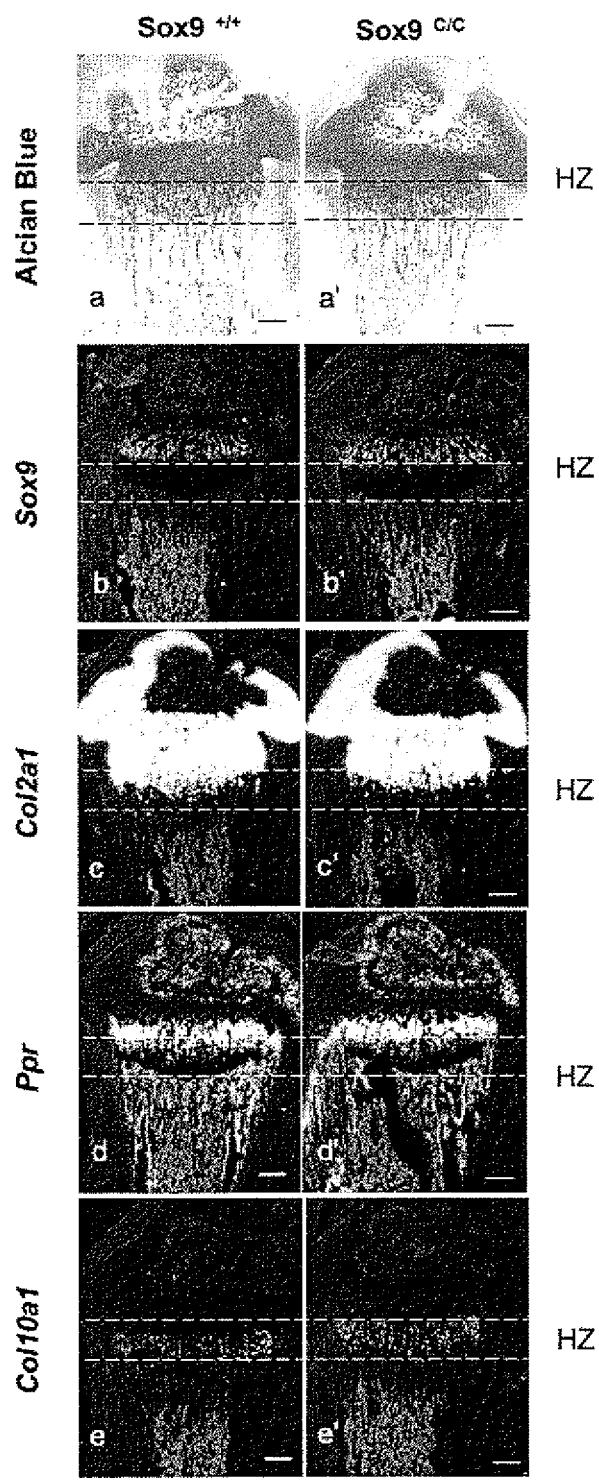

The contribution of ATF4 activation of Sox9 in reverting HC differentiation by conditionally inactivating Sox9 in C10-ATF4 HC was then assessed using HC-specific Col10a1-Cre (56) (FIG. 4E). In the absence of Sox9, the expansion of HZ in C10-ATF4 mice was markedly reduced and there were fewer cells expressing Col2a1 in the HZ (FIG. 4F-4G). Moreover, conditional inactivation of Sox9 in 13del mice reduced expression of Col2a1 and Ppr in HC and the HZ expansion was greatly reduced (FIG. 4I-4L). Deletion of Sox9 in wild-type HC did not affect chondrocyte hypertrophy (FIG. 4M). Collectively, these data suggest PERK-induced overexpression of ATF4 reverts differentiation in 13del HC by direct activation of Sox9 in HC, thereby perturbing chondrocyte hypertrophy.

CHOP Plays an Adaptive and Pro-Survival Role in 13Del HC

How do the ER-stressed HC survive? CHOP is another prominent transcription factor activated in the PERK, downstream of p-eIF2α, that regulates protein synthesis via the GADD34 negative feedback loop, which restores protein synthesis and induces oxidative stress via Ero11 (45, 64).

Although CHOP is widely considered as a proapoptotic factor (45), it has context- and cell-type specific roles as an adaptive and pro-survival factor in several diseases (65-68). Therefore, the contribution of CHOP in the adaptation of 13del HC was assessed.

Figure 5A:
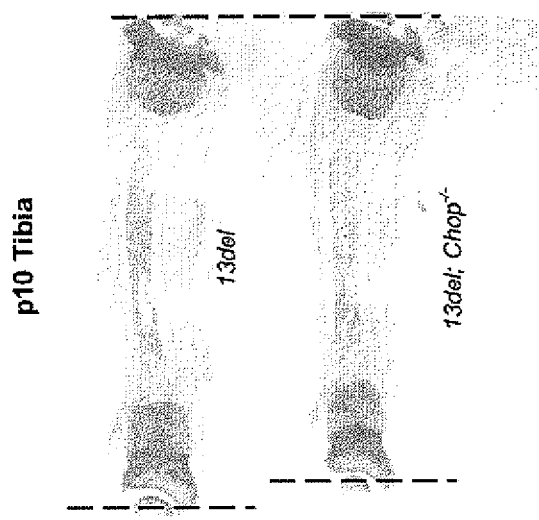
FIGS. 5A-5H show the study design.
Figure 5B:
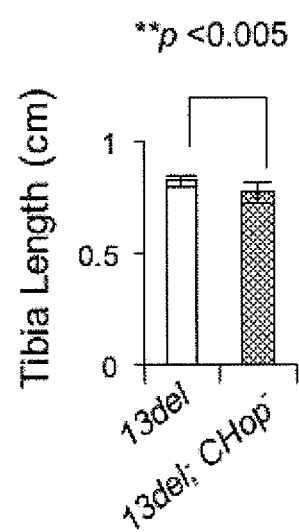
Figure 5C:
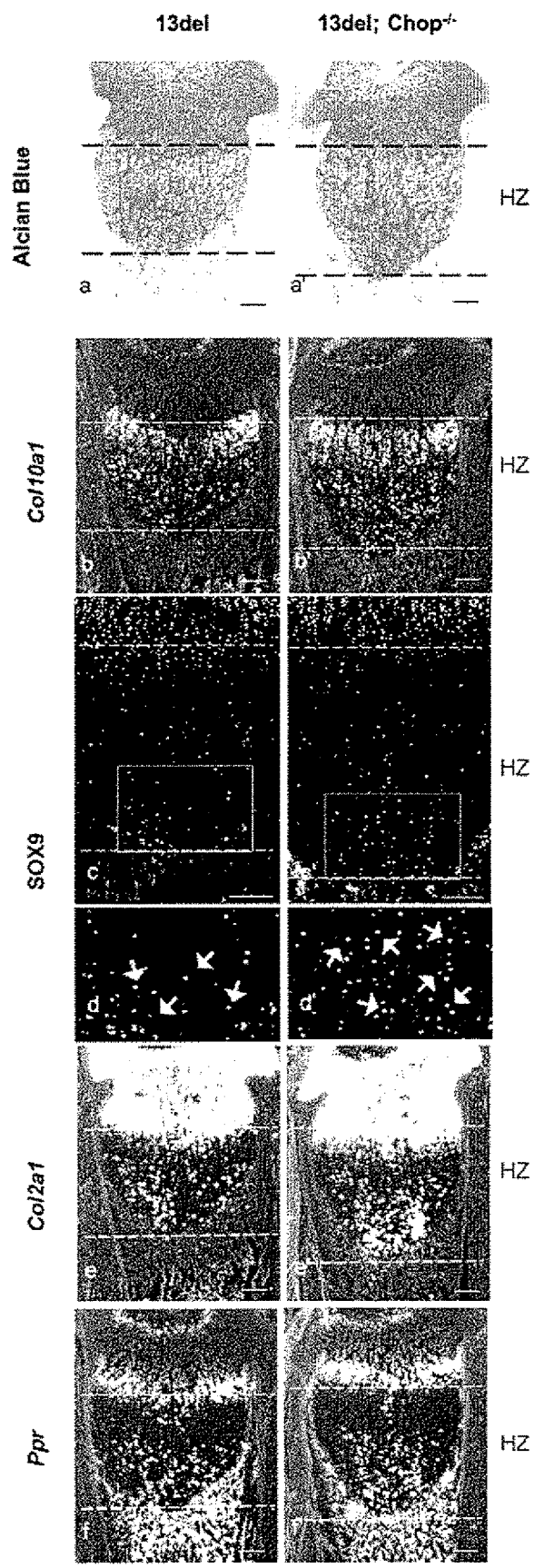
Figure 5D:
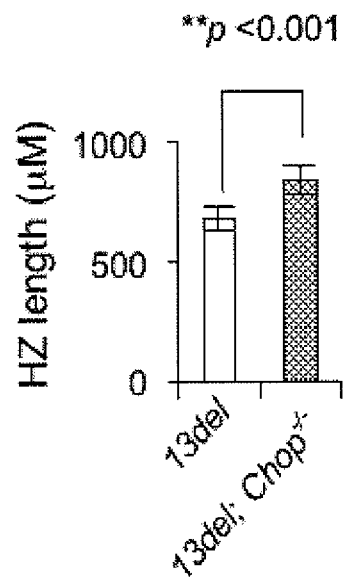
Figure 5E:
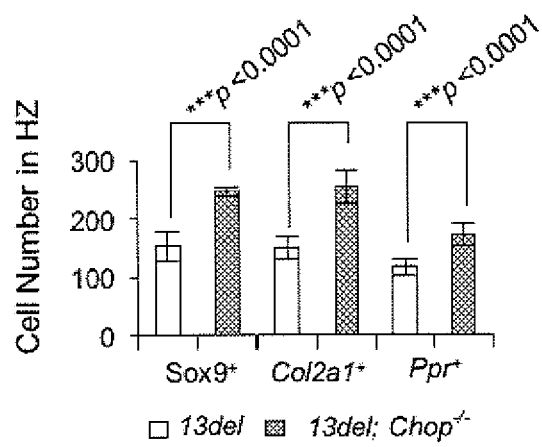
Figure 5F:
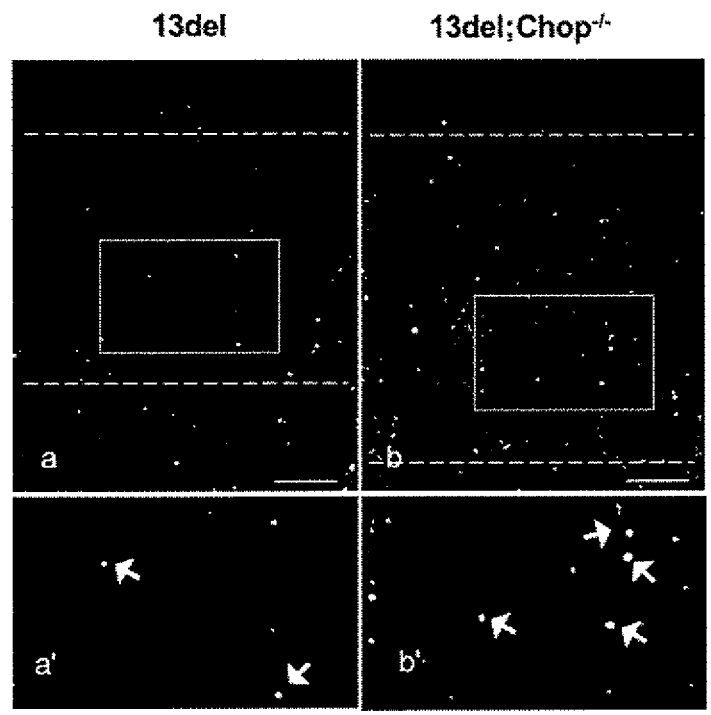
Figure 5G:
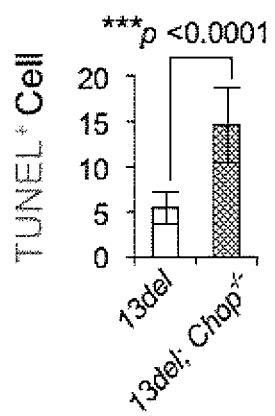

It is found that ablating Chop in 13del mice exacerbated the skeletal defects and growth plate phenotype. The 13del; Chop$^{-/-}$ mice displayed further tibial shortening (FIG. 5A an 5B) with greater (~20%) HZ expansion (FIGS. 5C and 5D), and increased number of chondrocytes expressing immature chondrogenic markers SOX9, Col2a1 and Ppr in the HZ (FIGS. 5C and 5E). Strikingly, in contrast to 13del, there was increased apoptosis in 13del;Chop$^{-/-}$ HC, consistent with a pro-survival role for CHOP (FIGS. 5F and 5G).

Figure 5H:
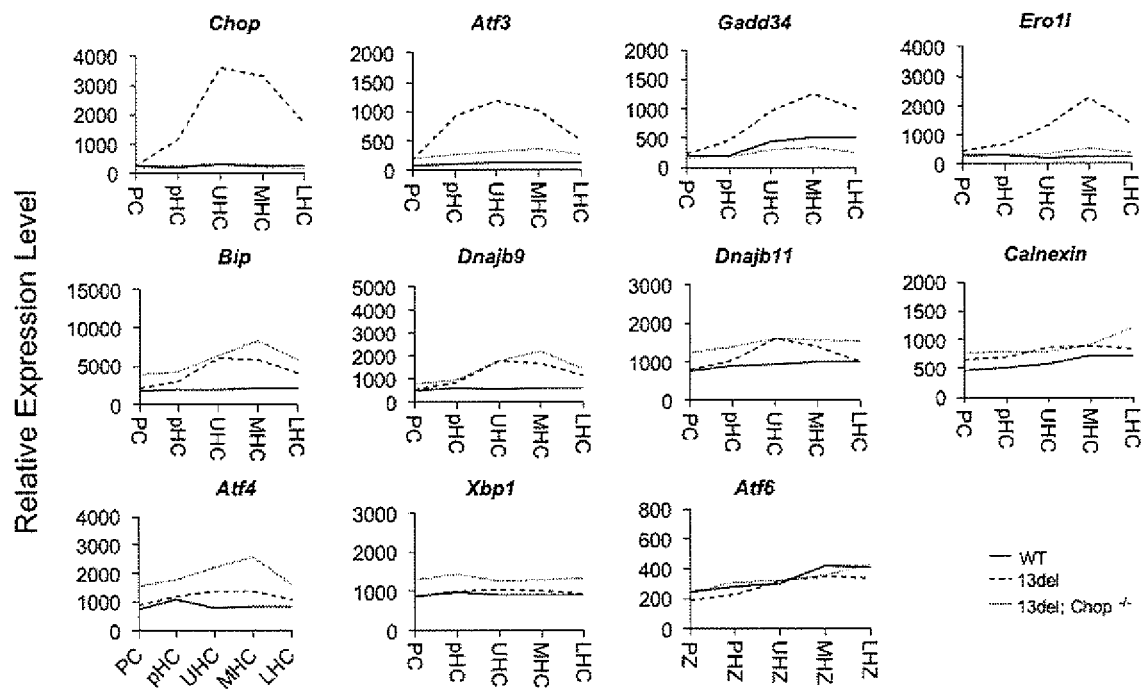

These results are in contrast to the pro-apoptotic role reported for CHOP in a mouse model of Pseudoachondroplasia caused by expression of misfolded cartilage oligomeric matrix protein in proliferating and hypertrophic chondrocytes, where deleting CHOP reduced apoptosis but exacerbated growth plate chondrocyte disorganization (69, 70). These differences may be due to variation in the responses of proliferating versus hypertrophic chondrocytes and/or the acuteness and duration of the ER stress. The present transcriptome analyses of fractionated 13del; Chop$^{-/-}$ growth plates revealed up-regulation of molecular chaperones (Bip, Dnajb9, Dnajb11 and Calnexin) and ER stress sensors Xbp1 and Atf4 in the middle and lower HZ (FIG. 5H). By contrast, the PERK signaling pathway was enfeebled, reflected by marked (>3.5 fold) down-regulation of CHOP targets Atf3, Gadd34 and Ero1l. In the absence of CHOP, recovery of translation mediated by GADD34 would be impaired and sustained shutdown of translation would favour apoptosis. Therefore, CHOP mediates 13del HC survival and it was important to identify pro-survival/anti-apoptotic factor(s) downstream of CHOP and ATF4.

Figure 6A:
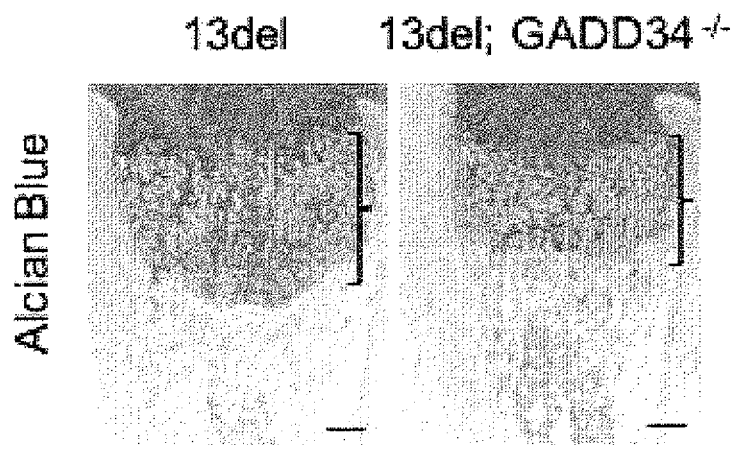
FIGS. 6A-6F show GADD34 inactivation exacerbated the dwarfism while reduced the HZ abnormality in 13del mice.
Figure 6B:
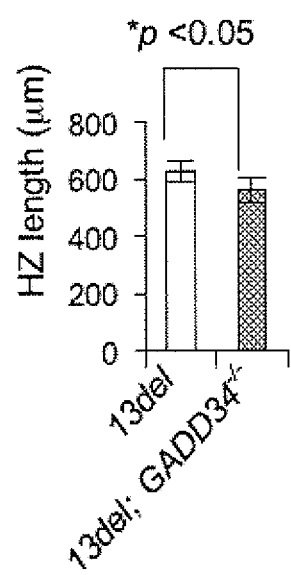
Figure 6C:
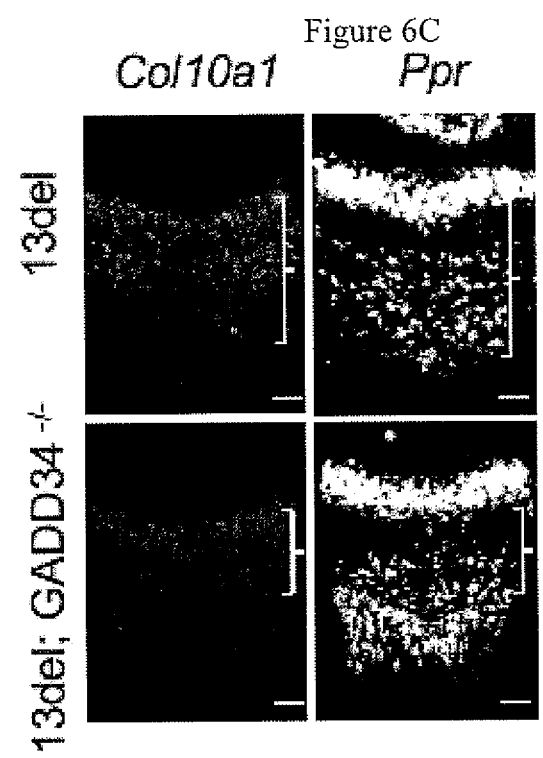
Figure 6D:
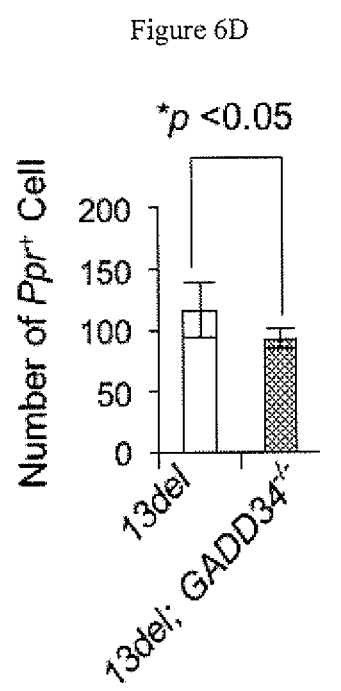
Figure 6E:
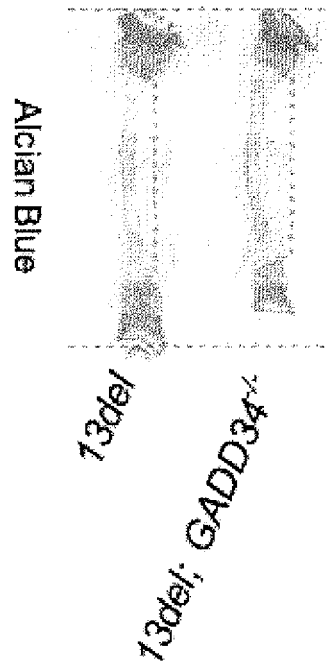
Figure 6F:
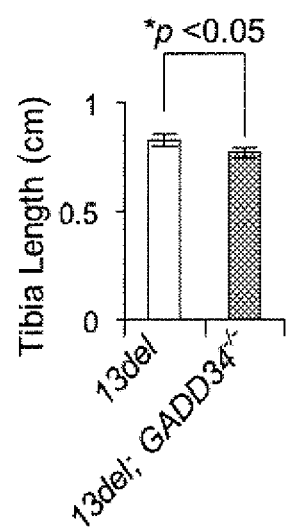

On the other hand, ablation of GADD34, the modulator of translation recovery and downstream target of CHOP, from 13del HCs lead to a HZ reduction on day 10 (89% of 13del, n=5) (FIGS. 6A and 6B), accompanied by fewer Ppr+ cells in the mid- and lower portions of the HZ (FIGS. 6C and 6D). This finding supports the notion that UPR is interrelated to the MCDS phenotype and attenuation of ER stress via preventing translation recovery is potential to ameliorate the growth plate phenotype. Because GADD34 is important for the reinitiation of protein synthesis which in the context of 13del means that the 13del mRNA would be translated and mutant protein would be re-expressed triggering another round of ER stress, inactivating or reducing the activity of GADD34 should prevent another round of insult. However, although the differentiation changes were reduced, the tibia length in 13del;GADD34$^{-/-}$ mice was further shortened (88% of 13del, n=5) (FIGS. 6E and 6F). One possible reason is GADD34 deficient cells may retain eIF2α-directed phosphatase activity, via the activation of a redundancy factor CReP, the constitutive repressor of eIF2α phosphorylation (71).

ATF4 and CHOP Mediate Chondrocyte Survival by Activating Fgf21

Figure 7A:
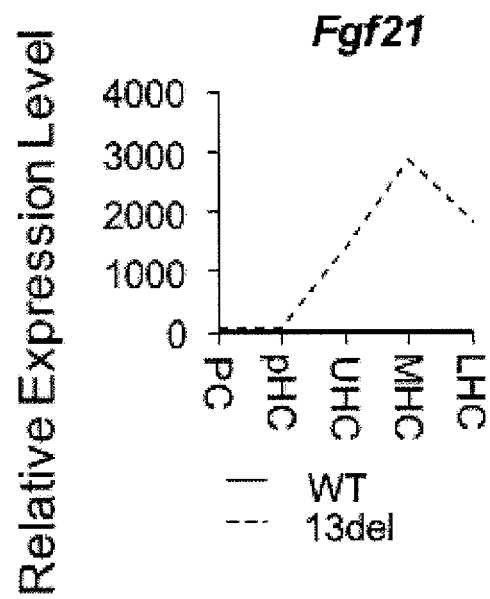
FIGS. 7A-7O show FGF21, regulated by ATF4 and CHOP, protects the HCs from ER stress.
Figure 7B:
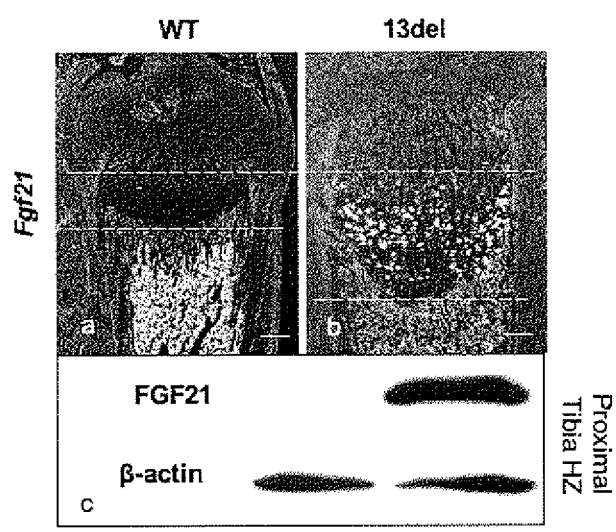
FIG. 7B illustrate a significant up-regulation of FGF21 in 13del HCs at p10 stage, validated by in situ hybridization (a, b) and western blot.

CHOP acts not only downstream of ATF4, but also as its interacting partner in modulating ER stress targets (45). To elucidate the pro-survival role of the PERK signaling pathway in 13del HC, target genes of CHOP and ATF4 in Cluster I were searched. Fgf21, a reported target of ATF4 (72), was found to be the most up-regulated gene in 13del HC (FIG. 7A), which was confirmed by in situ hybridization and immunoblotting (FIG. 7B). Fgf21 was similarly reported to be activated in ER-stressed chondrocytes (73).

Figure 7C:
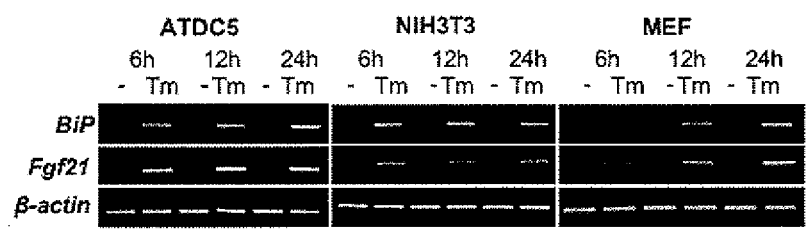
In FIGS. 7C and 7D, Fgf21 is significantly activated in response to Tunicamycin (Tm) in ATDC5, NIH3T3 and MEF cells, at indicated time points. The activation of Bip indicates ER stress is triggered.
Figure 7D:
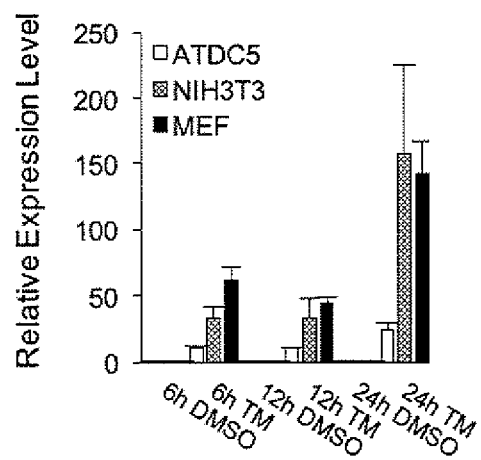

FGF21 is a hormone with roles in glucose and lipid metabolism (74) and plays an survival role in the response to diverse stressful conditions, such as amino acid deprivation, mitochondrial stress and ER stress associated with diseases such as diabetes, cardiovascular disease (75-77). Fgf21 expression was found to be greatly increased (>100 fold) in response to treatment with the ER stress inducer tunicamycin in fibroblasts (NIH3T3 and MEF cells) and ATDC5 cells (FIGS. 7C and 7D).

Figure 7E:
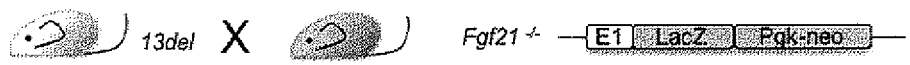
FIG. 7E is a schematic diagram of generation of 13del; Fgf21$^{-/-}$ mice.
Figure 7F:
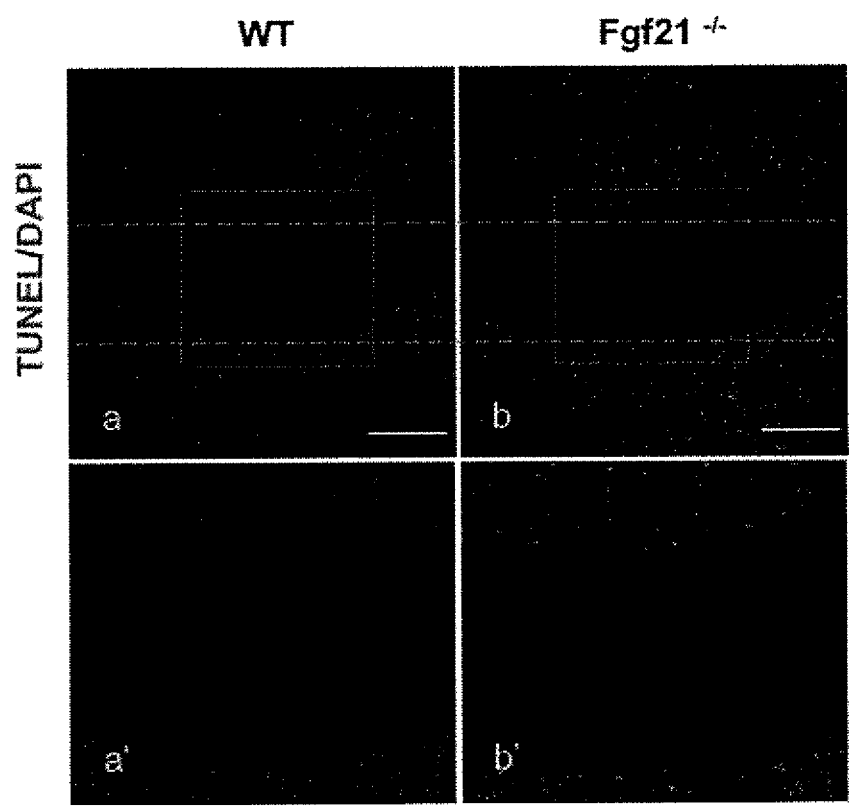
FIG. 7F shows the ablation of Fgf21 from WT HCs does not affect cell survival.
Figure 7G:
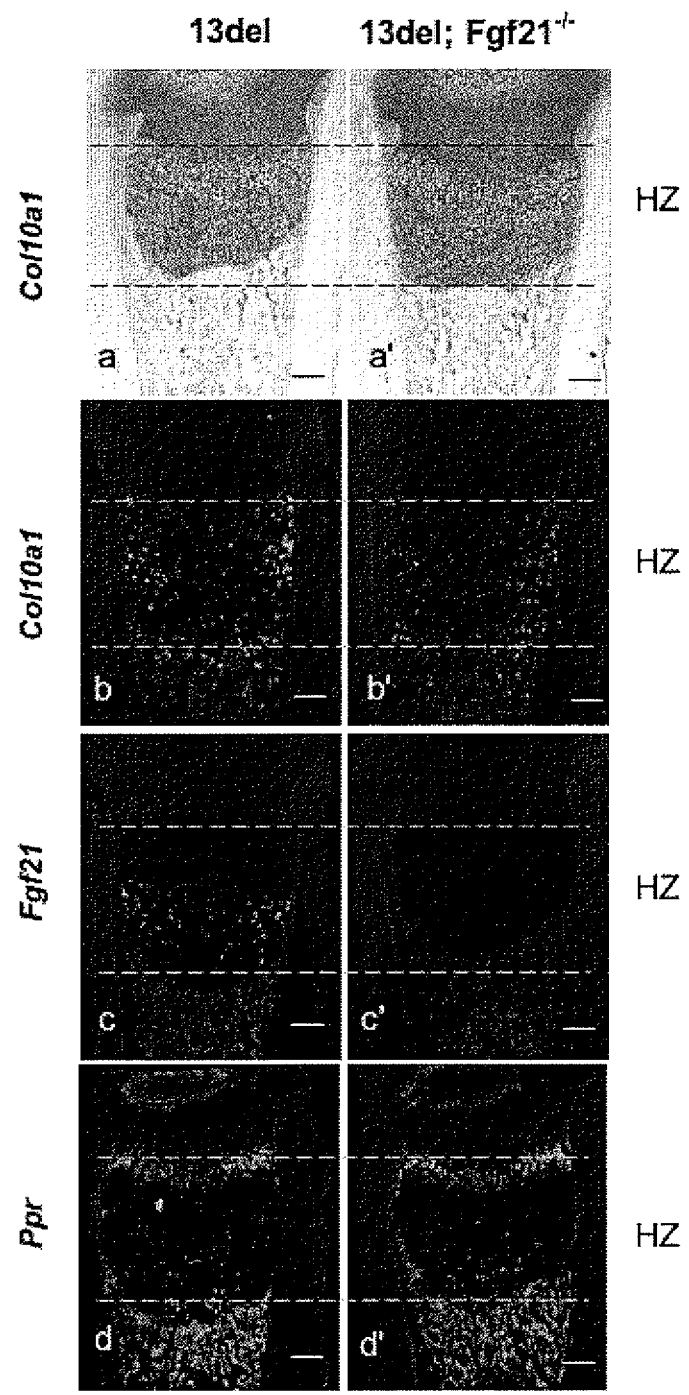
FIG. 7G shows that growth plate of 13del; Fgf21$^{-/-}$ mice exhibited comparable phenotype to 13del mice, as shown by histology (a, a'), expression analysis of Col10a1 (b, b'), Fgf21 (c, c') and Ppr (d, d').
Figure 7H:
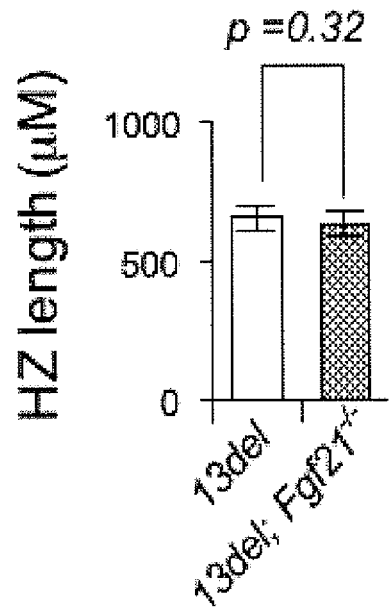
FIGS. 7H and 7I respectively show the measurement of HZ lengths and quantification of Ppr positive cells in 13del and 13del; Fgf21$^{-/-}$ mice.
Figure 7I:
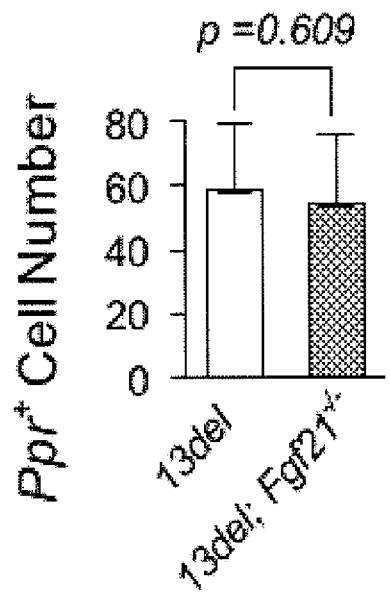
Figure 7J:
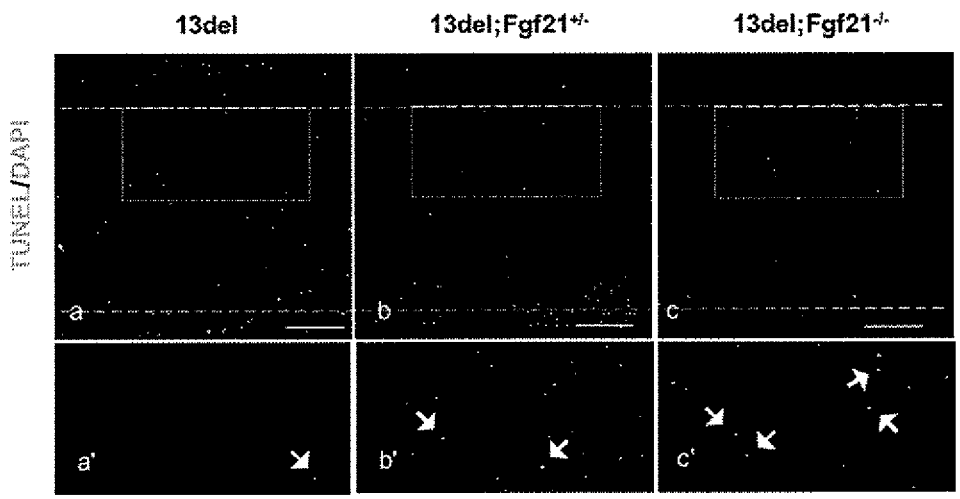
FIGS. 7J and 7K illustrate that FGF21 protects the 13del HCs from death in dosage-dependent manner.
Figure 7K:
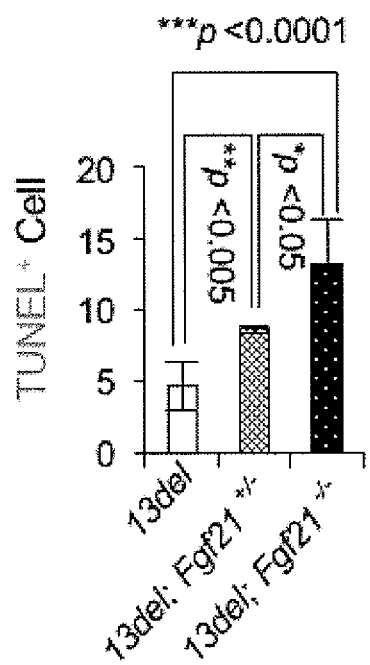

The present invention assessed whether FGF21 had a survival role in 13del HC by genetically ablating the gene (FIG. 7E). Fgf21 null mice have normal growth plates and HC viability (FIG. 7F). The hypertrophic zone expansion in 13del;Fgf21$^{-/-}$ mice was comparable to that of 13del mice, and the reverted differentiation process was not affected (FIG. 7G-7I). However, increased apoptosis was found in the HZ of Fgf21-deficient 13del mice. This protective effect of FGF21 against apoptosis is dose dependent (FIGS. 7J and 7K).

Figure 7L:
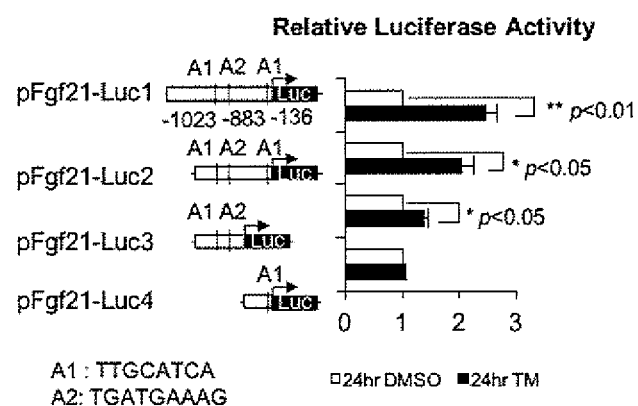
In FIG. 7L, two putative ATF4 binding sites (A1 and A2) were predicted in the Fgf21 promoter region. Luciferase activities of Fgf21 wild type, deletion or mutated ATF4 binding sites promoter reporter in response to Tunicamycin or DMSO treatment FIG. 7M indicates that ectopic expression of Atf4 (a, a') is insufficient for Fgf21 (b, b') induction in HCs.
Figure 7L:
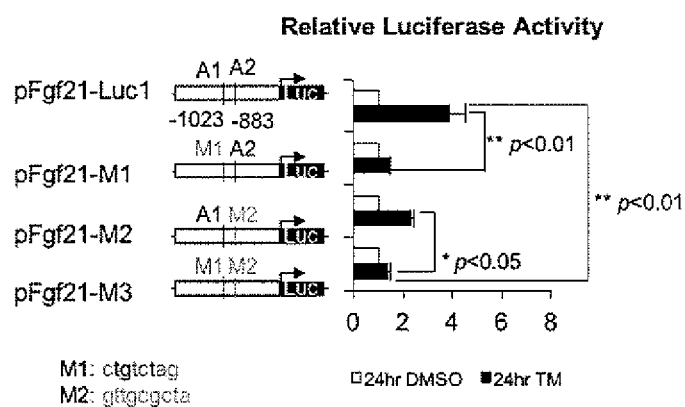
Figure 7M:
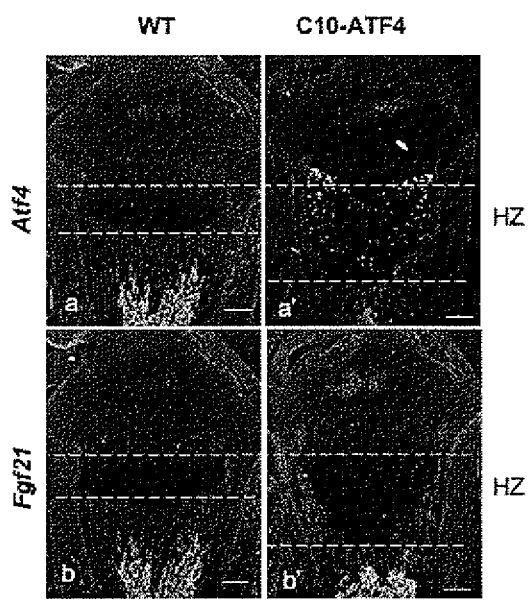
In FIG. 7N, results of ChIP-PCR showed the binding of ATF4 and CHOP to the ATF4 binding-peak-containing region on the Fgf21 promoter under ER stress in NIH3T3 cells.
Figure 7N:
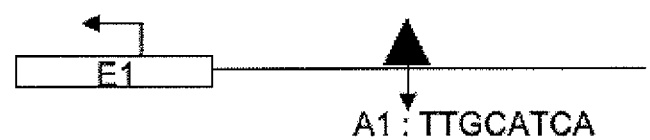
Figure 7N:
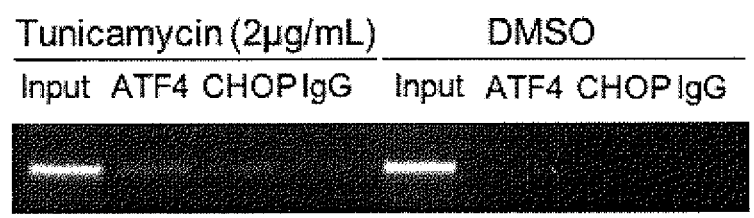
Figure 7O:
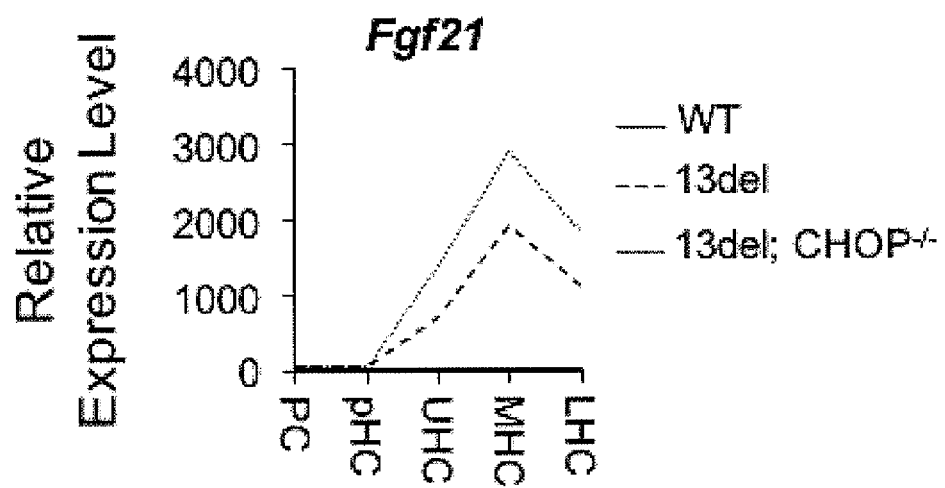

The present invention next tested the functional relevance of a reported C/EBP-ATF4 binding motif in the Fgf21 promoter (78) that coincided with an ATF4 peak. By transactivation assays (FIG. 7L), it was found that deleting (pFgf21-Luc3 and pFgf21-Luc4) or mutating (pFgf21-M1 and pFgf21-M3) the ATF4 binding motif abolished the transactivation ability of ATF4. However, Fgf21 was not induced in C10-ATF4 mice (FIG. 7M), suggesting ATF4 is necessary but not sufficient for Fgf21 induction. The need for another factor is supported by ChIP assays where we found both ATF4 and CHOP bind to the ATF4 motif-containing peak region in the cells under ER stress (FIG. 7N), even though no CHOP binding peak was detected in the Fgf21 promoter. Expression of Fgf21 was down-regulated by approximately 40% in 13del;Chop$^{-/-}$ HC despite the upregulation of Atf4 (FIG. 7O), consistent with a requirement for ATF4-CHOP cooperation to induce Fgf21 under ER stress. Thus, the present results show that ATF4 and CHOP work together to induce directly Fgf21 expression in 13del HC for their survival.

ISRIB Inhibition of the PERK Signaling can Ameliorate 13Del Skeletal Deformities In the UPR, PERK phosphorylation of serine 51 in eIF2α is the critical upstream controlling point that triggers the p-eIF2α/ATF4/CHOP signaling pathway (18). The present data show that genetically ablating the key transcription factors in the PERK signaling as a strategy for rescuing the aberrant chondrocyte differentiation is imperfect, because of effects on cell survival. In addition, addressing the effects of transcription factor over-expression and cell-type specificity is required because ATF4 is essential for normal development. Therefore, it is necessary to identify a suitable entry point in the pathway which can be manipulated for protection or rescue from the effects of ER stress, without interfering with normal developmental function.

As summarized in Table 2, small molecules targeting PERK signaling pathway have been reported in neurodegenerative disorders and cancer therapy (14). Recently, a small molecule, Integrated Stress Response InhiBitor (IS-RIB) has been reported to render cells insensitive to eIF2α phosphorylation by targeting the interaction between eIF2 and eIF2B, and its activity is independent of eIF2α phosphorylation (79, 80). ISRIB shows acceptable pharmacokinetic properties and no overall toxicity in mice, and has been reported to show significant neurotrophic effects in mice (79, 81).

TABLE 2

Pharmaceutically Targeting PERK Signaling Pathway in Disease

| Molecules | Target (Effects) | Disease | Phase |
|---|---|---|---|
| Salubrinal | Enhancing eIF2α phosphorylation and downstream ATF4 signaling. | Amyotrophic Lateral Sclerosis<br>Parkinson's Disease | Preclinical<br><br>Preclinical |
| ISRIB | Inhibiting eIF2α mediated translation control and ATF4 induction | Learning ability and Memory | Preclinical |
| GSK2656157 | Inhibition of PERK and eIF2α phosphorylation, ATF4 translation and CHOP mRNA expression | Multiple myeloma, pancreatic cancer | Preclinical |
| Bortezomib (PS341) | Activation of PERK, ATF4 or CHOP activity | Various cancers | FDA approved for multiple myeloma |

Figure 8A:
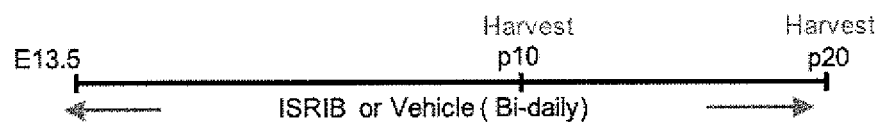
FIGS. 8A-8Q show that small molecule ISRIB, by preventing ATF4 induction under ER stress, ameliorates 13del skeletal deformities.
Figure 8B:
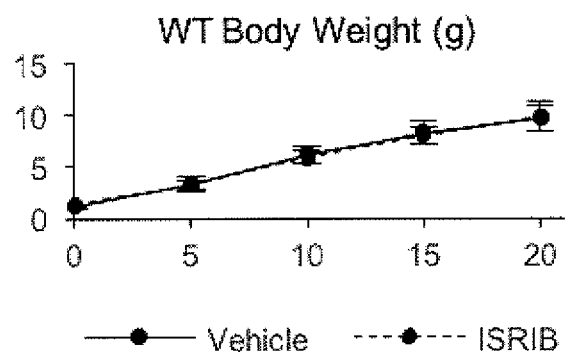
FIGS. 8B and 8C indicated that treatment of ISRIB does not affect the body weight gain or body length growth in wild type mice.
Figure 8C:
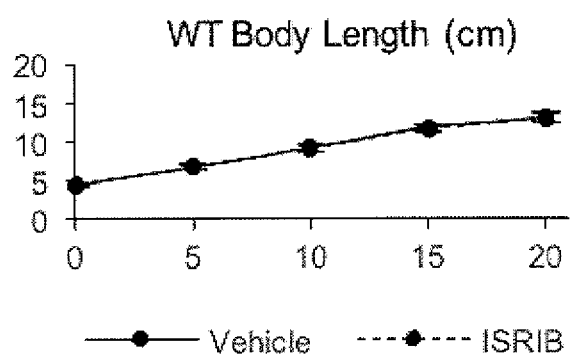
Figure 8D:
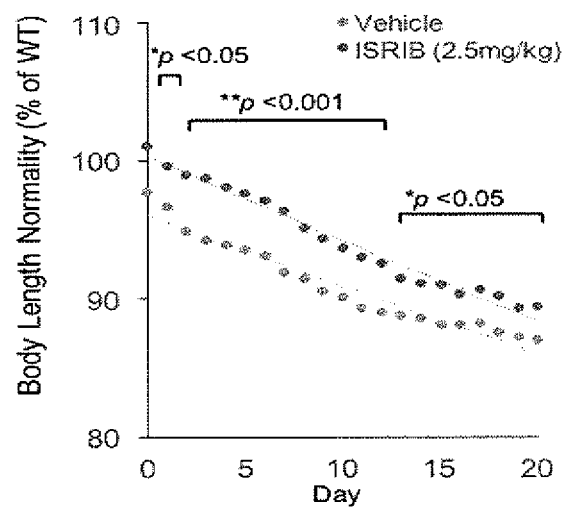
In FIG. 8D, body lengths of the vehicle-treated (n=20) and ISRIB-treated (n=16) 13del were monitored from birth to p20 stage, and a significantly consistent improvement of body length in ISRIB-treated 13del mice was observed.
Figure 8E:
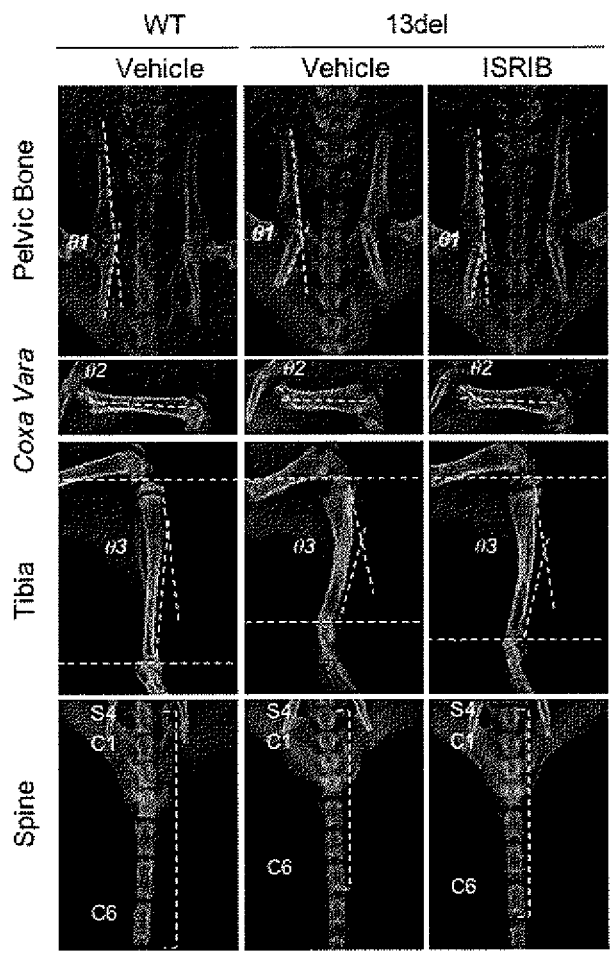
Figure 8H:
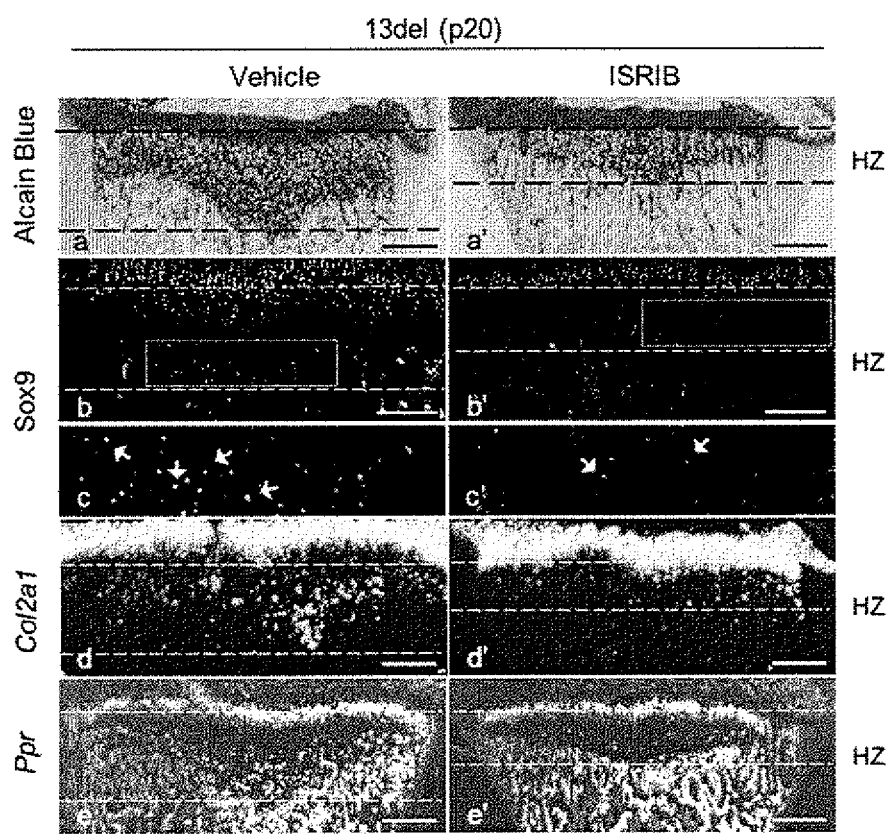
Figure 8I:
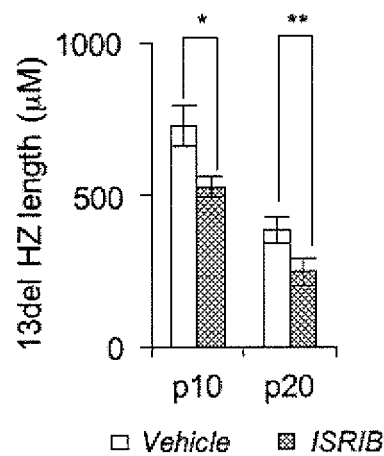
FIGS. 8I and 8J respectively show the HZ length measurement and SOX9$^+$, Col2a1$^+$ and Ppr$^+$ cells quantification of tested animals at indicated time points.
Figure 8J:
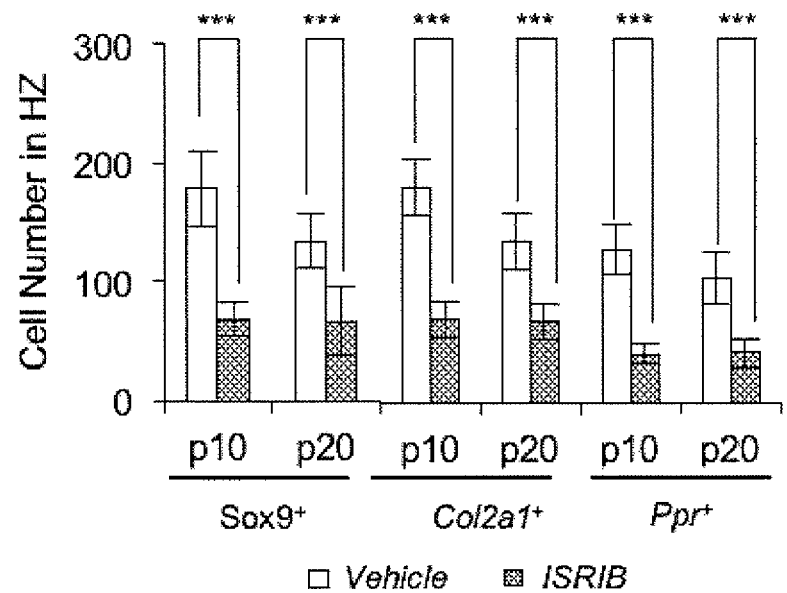

The potential of ISRIB to modify the chondrodysplasia phenotype was tested by treating 13del and wild-type littermates with ISRIB or vehicle twice daily by intraperitoneal injection from E13.5 (onset of expression of 13del transgene) to postnatal day 20 (p20) (FIG. 8A). In wild-type mice, ISRIB had no adverse effects on weight gain or body growth (FIGS. 8B and 8C). However, ISRIB markedly reduced the dwarfism of 13del mice from new born to juvenile stages (FIG. 8D). Radiographic analyses revealed treatment with ISRIB ameliorated the skeletal deformities at p20 (FIGS. 8E and F), including the length of tibia/femur and spine; tibia bowing (genu varum: the angle between proximal head and distal head of tibia); pelvic bone orientation (the angle between ilium and pubis), and coxa vara (narrowed angle between the proximal head and the shaft of the femur) (FIG. 8E).

Figure 8K:
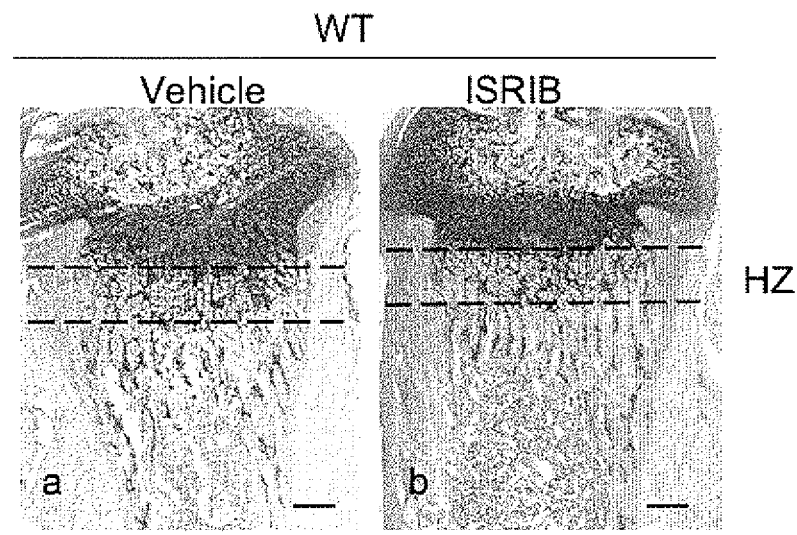
FIG. 8K suggests that histology of p10 growth plates were comparable between ISRIB- and vehicle-treated WT mice.
Figure 8L:
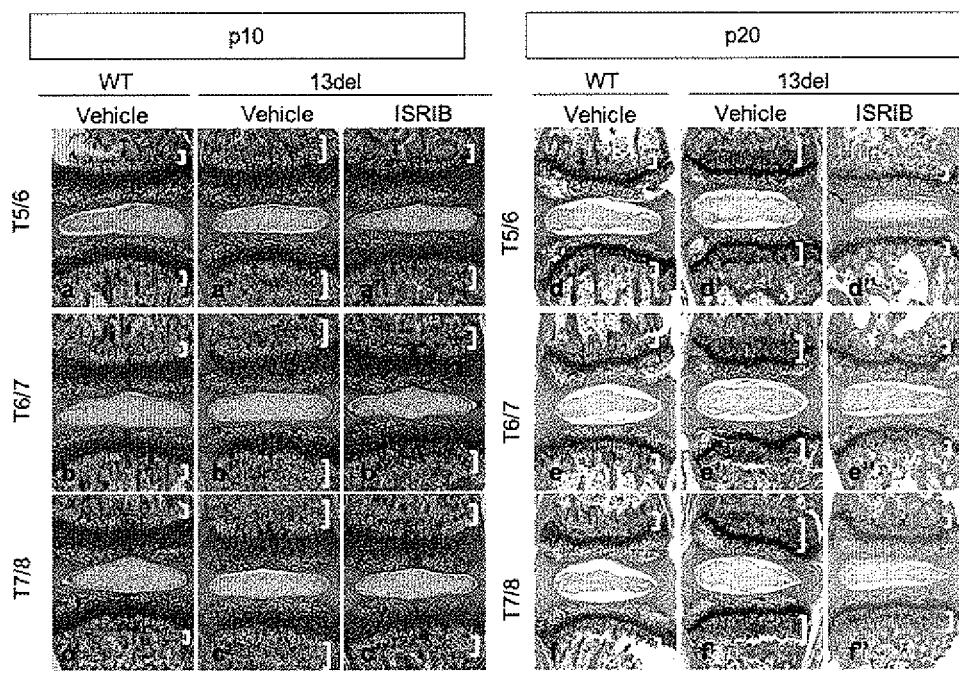
FIGS. 8L and 8M show the rescue of the HZ expansion in caudal intervertebral disc (IVD) by the treatment ISRIB in 13del mice at p10 and p20 stage.
Figure 8M:
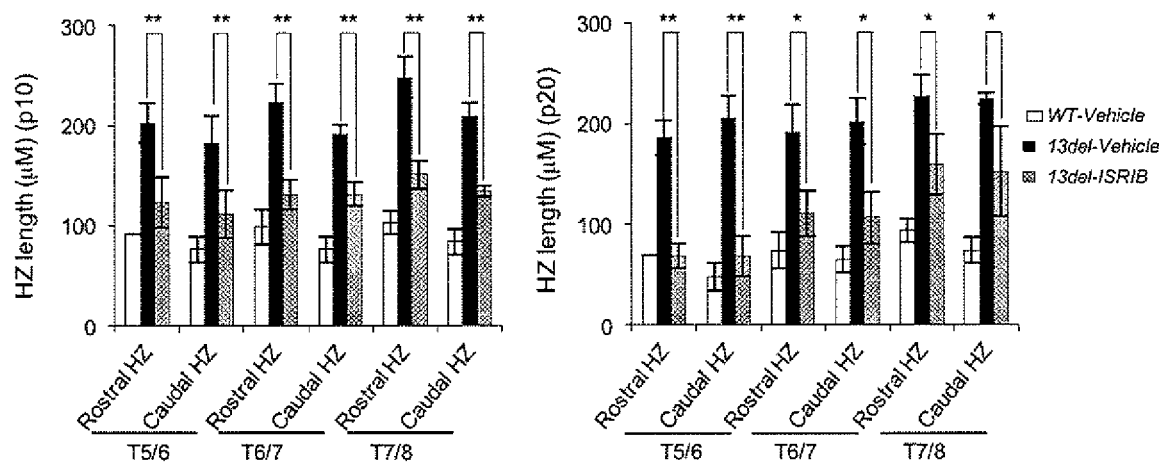
Figure 8N:
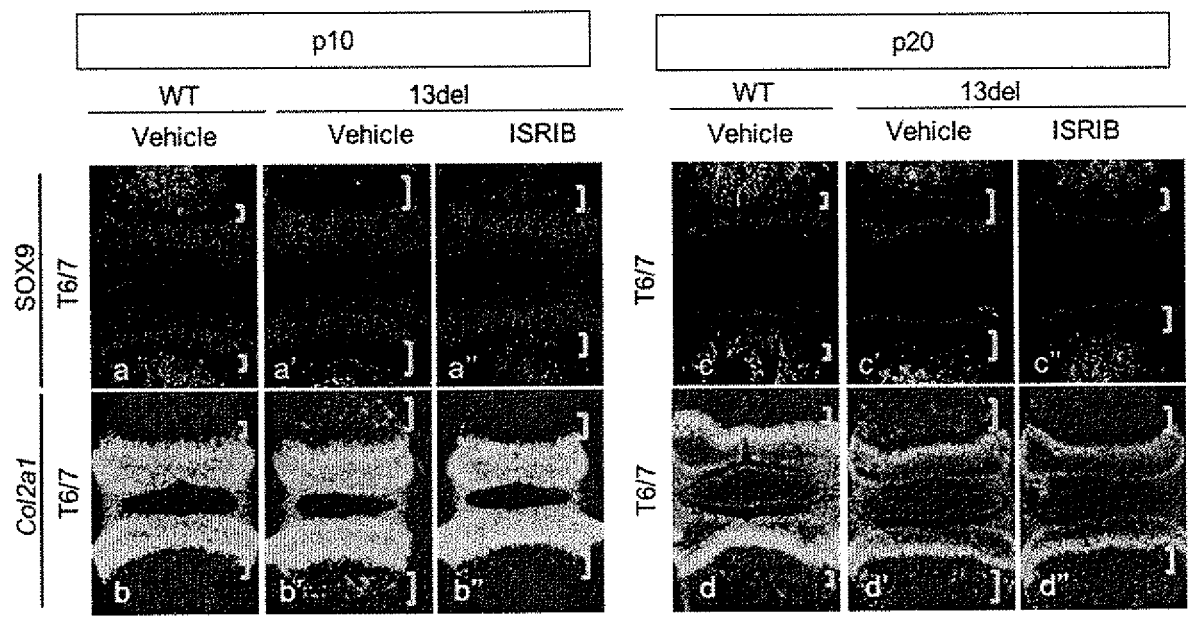
FIG. 8N shows the rescue of the growth plate deformities in caudal IVD by the treatment of ISRIB in 13del mice, indicated by reduced number of SOX9 (a-a", c-c") and Col2a1 (b-b", d-d") at p10 and p20 stages.
Figure 8P:
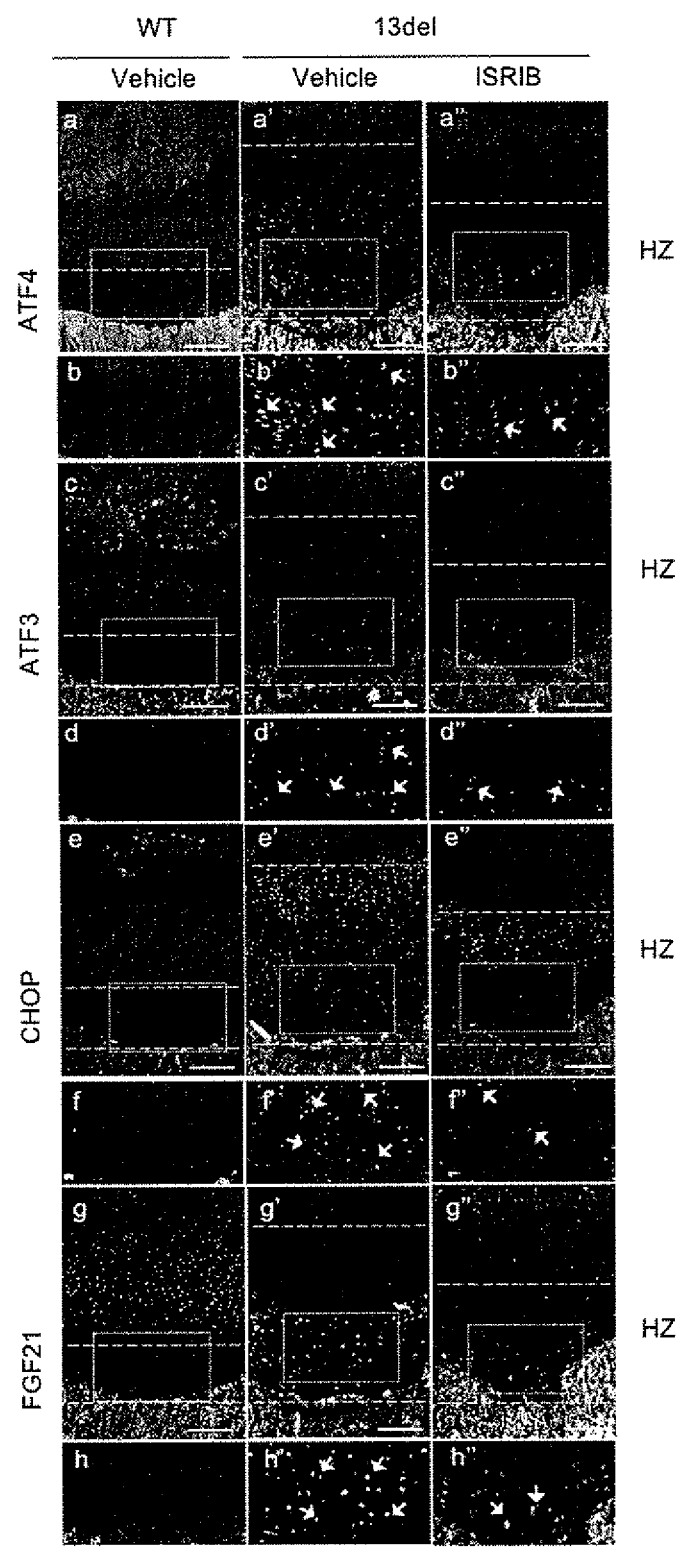
FIG. 8P indicates that at p10, the protein level of ATF4 (a-b"), ATF3 (c-d"), CHOP (e-f") and FGF21 (g-h") were down-regulated in HZ from ISRIB-treated 13del mice.
Figure 8Q:
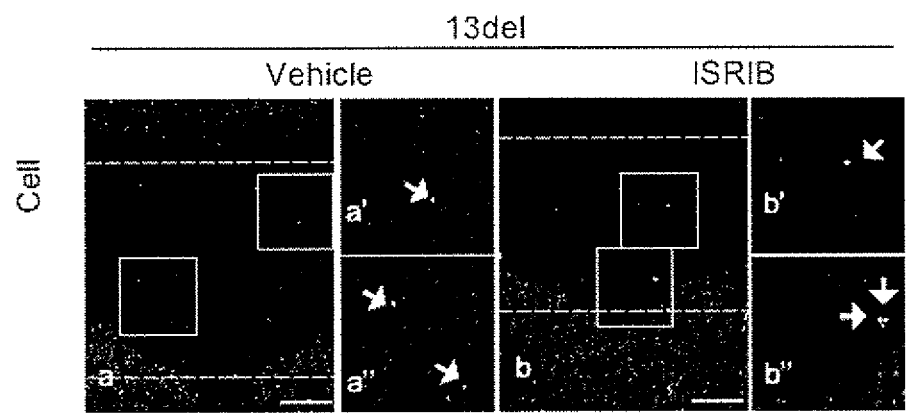

Moreover, it was found that the HZ expansion in the limb growth plates of ISRIB-treated 13del mice was greatly reduced and the number of SOX9$^+$, Col2a1$^+$ and Ppr$^+$ cells in the HZ at p10 and p20 was diminished (FIG. 8G-8J). ISRIB had no observable effect on the limb growth plates in wild-type mice (FIG. 8K). ISRIB treatment in 13del mice also reduced the deformities in other growth plates such as the axial skeleton, with reduced HZ expansion and decreased number of Sox9$^+$ and Col2a1$^+$ premature cells in tail intervertebral disc growth plates (FIG. 8L-8N). As expected, ISRIB specifically reduced the amount of ATF4 and CHOP protein, and inhibited p-eIF2c/ATF4/CHOP signaling transduction, marked by the down-regulation of the transcripts as well as the protein level of their downstream targets (ATF3, ERO11 and FGF21) (FIGS. 8O and 8P). Importantly, inhibition of p-eIF2α/ATF4/CHOP by ISRIB did not induce apoptosis (FIG. 8Q) in 13del HC. Thus, without any obvious adverse effect, ISRIB corrected the molecular, histological, and skeletal defects in 13del mice.

The 13 Del-Knockin MCDS Mice

Figure 9A:
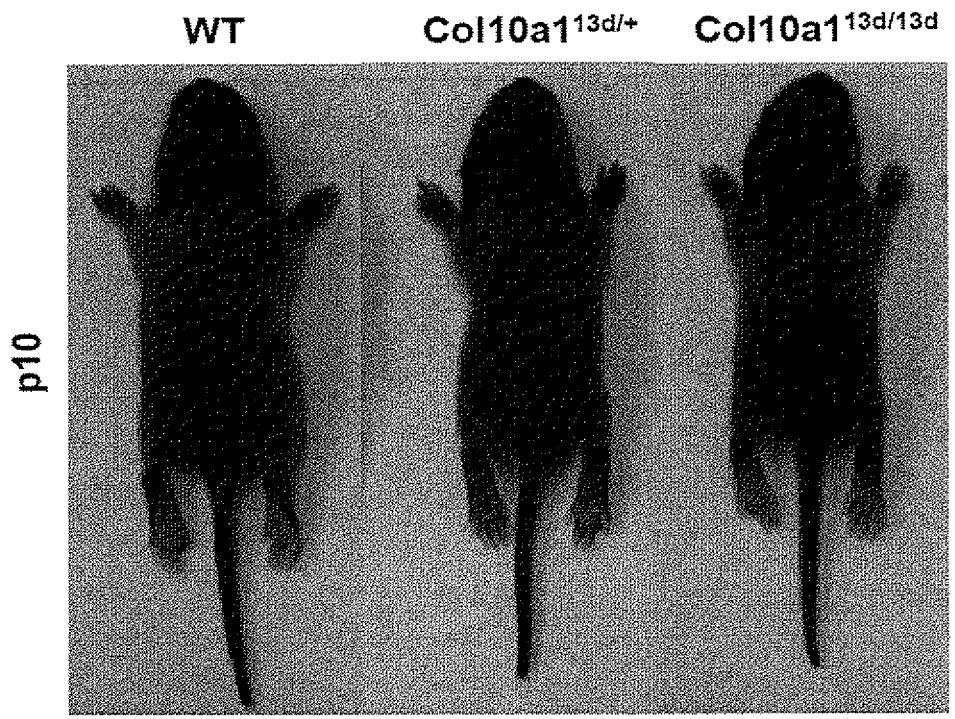
FIGS. 9A-9B show dwarfism and growth plate deformities in 13del-KI MCDS mice.

These mice are similar to the transgenic 13del mice in terms of the Col10a1 13del mutation except that in these mice the 13del deletion was introduced into the endogenous Col10a1 allele by homologous recombination in mouse embryonic stem (ES) cells. This mouse, referred to here as 13del-KI, therefore represents a direct equivalent model of the human 13del MCDS mutation and is another mouse model for the UPR triggered by expression of 13del-collagen X (FIG. 9A).

Comparison Between 13Del and 13Del-MCDS Mice

Figure 9B:
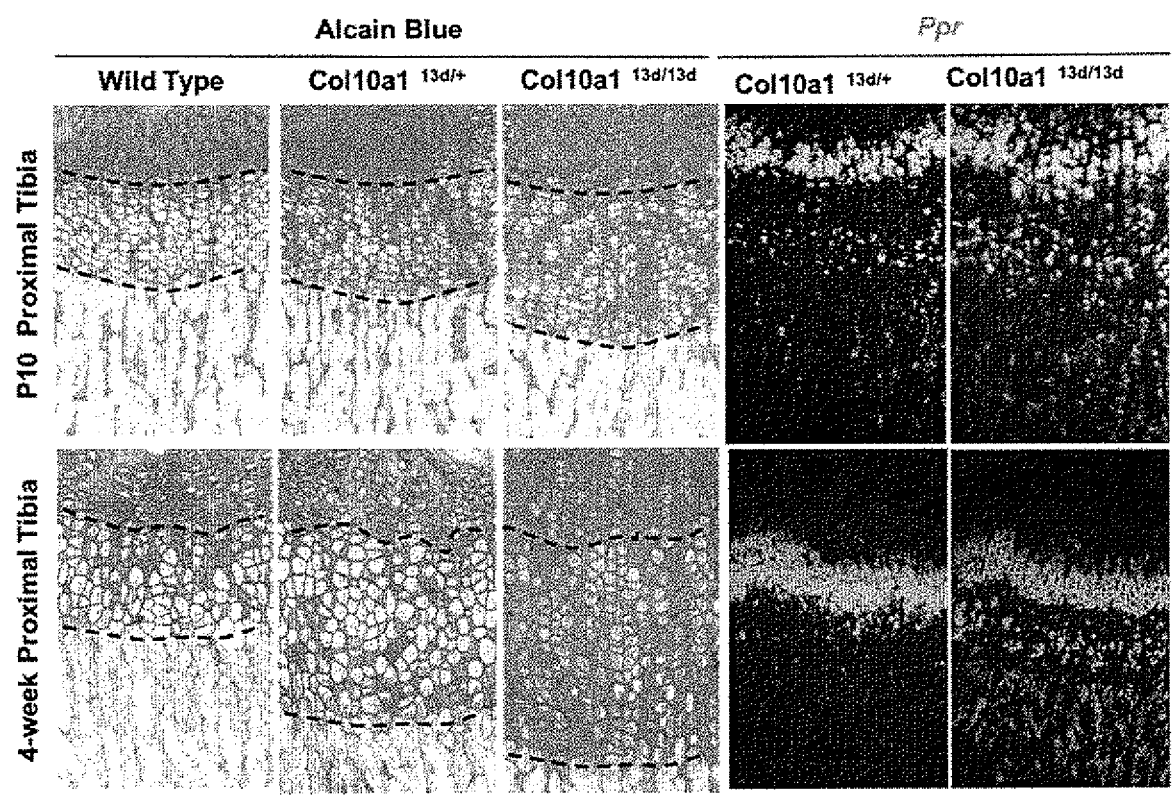

The 13del and 13del-KI mice express the same collagen X mutation. The gross phenotype of dwarfism of the 13del-MCDS was similar to that of 13del except for the absence of hyperostosis and the degree of expansion of the 13del-KI HZ was not as severe as for 13del. The 13del-KI mice recapitulated all the skeletal phenotypes of MCDS, including disproportionate dwarfism, and skeletal abnormalities including flaring of the metaphysis, coxa vara, deformities in the pelvic bones, in heterozygotes and homozygotes with the latter being more affected. Both mouse models display expanded HZ and accumulation of premature HCs (FIG. 9B). The bone (generalized hyperostosis) phenotype in 13del is caused by activation of ER stress in osteocytes due to ectopic expression of the transgene (106). The differences in severity in the degrees of expansion of the HZ, being more severe in the 13del than in 13del-KI mice, could be due to differences in the relative level of expression of wild-type and 13del collagen X protein in the two mutants. In addition, the duration of expression of 13del is shorter, being reduced by the 4 weeks while it is still expressed in the 13del-KI at that stage. The difference in duration can be attributed to the difference in regulatory region driving the mutant in the transgenic 13del compared to the 13del KI which is controlled by the full complement of Col10a1 regulatory elements. Additional differences are in the profile of differentiation defects in the HCs. In 13del mice HCs re-enter the cell-cycle but they remain in GI-S phase and do not undergo apoptosis but in the 13del-KI two rounds of hypertrophy occur with an intervening cell cycle re-entry and exit.

Intervertebral Disc Degeneration (IDD) in MCDS Mice

Figure 10A:
FIGS. 10A-10F show 13del and 13del-KI MCDS mice display degenerative intervertebral disc (IVD) features.

It is noted that some cases of MCDS display spinal abnormalities including in vertebral bodies and end plate irregularities (82). S. Ikegawa at Center for Integrative Medical Sciences, RIKEN, Tokyo, has examined the MRI of the spine of a 20-year-old male MCDS patient and found evidence for signal intensity loss ("dark disc") and irregularities in the end plate (FIG. 10A), consistent with the notion that endplate irregularities are associated with IDD (83).

Figure 10B:
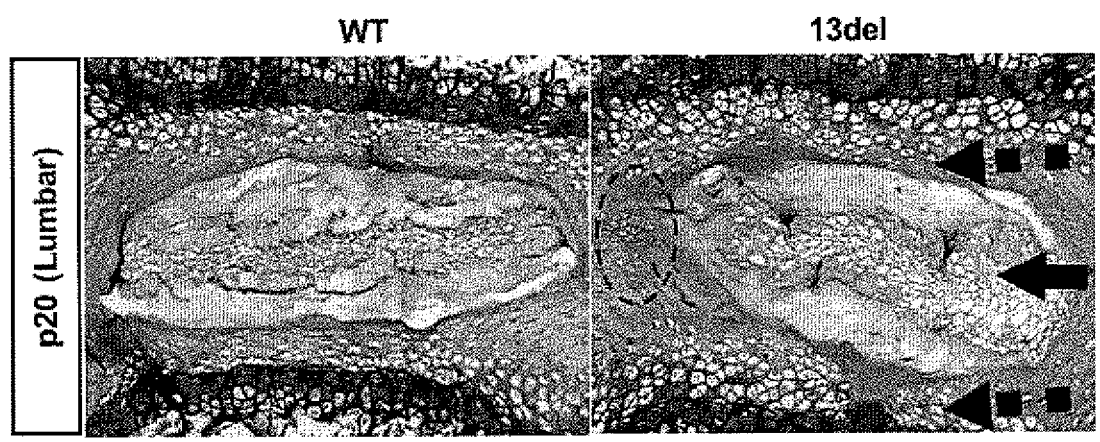
Figure 10C:
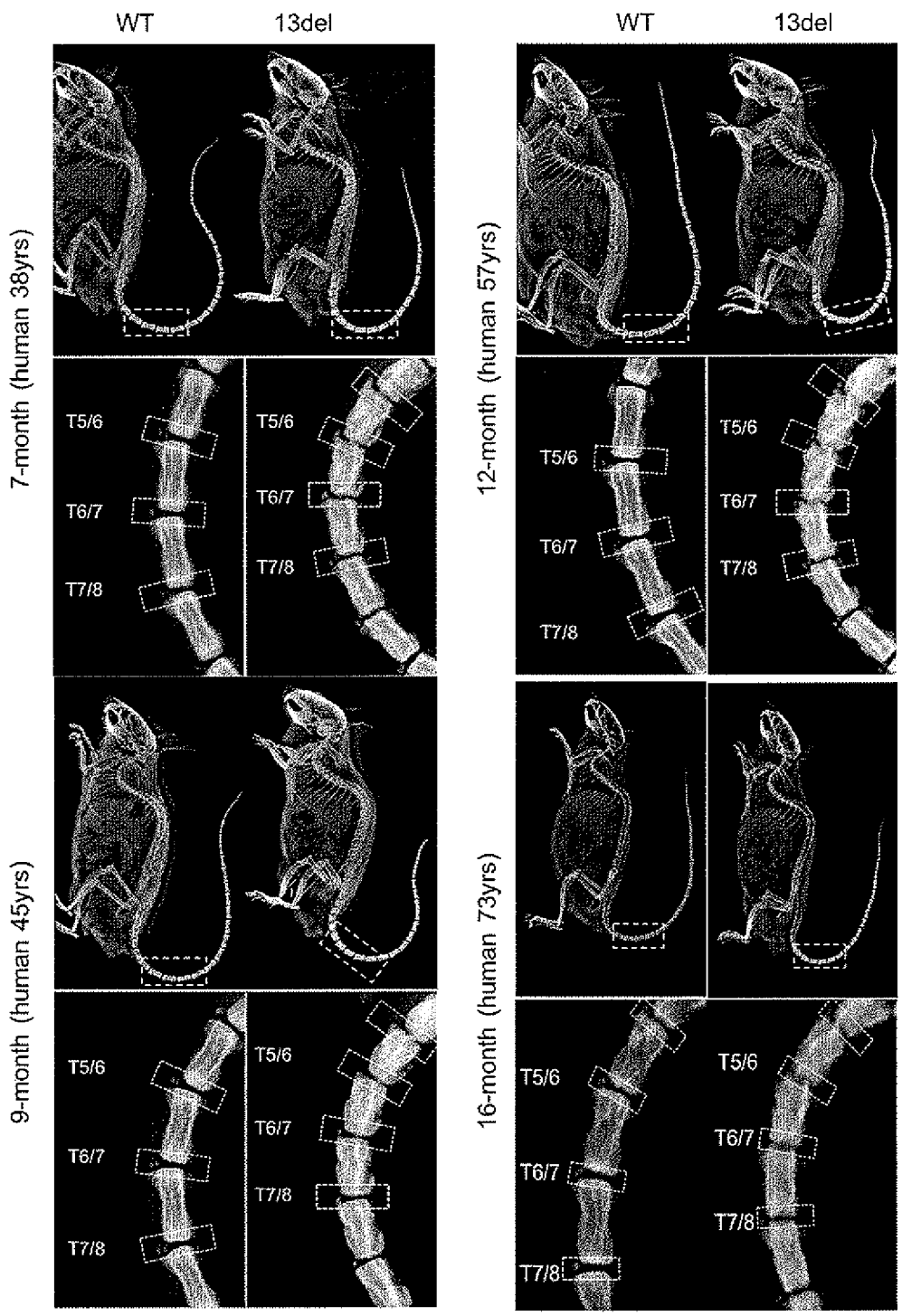
Figure 10D:
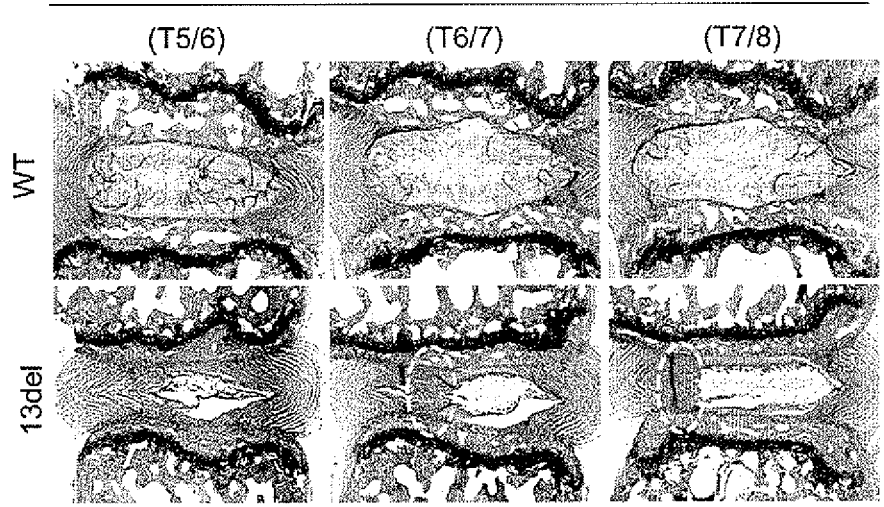
Figure 10D:
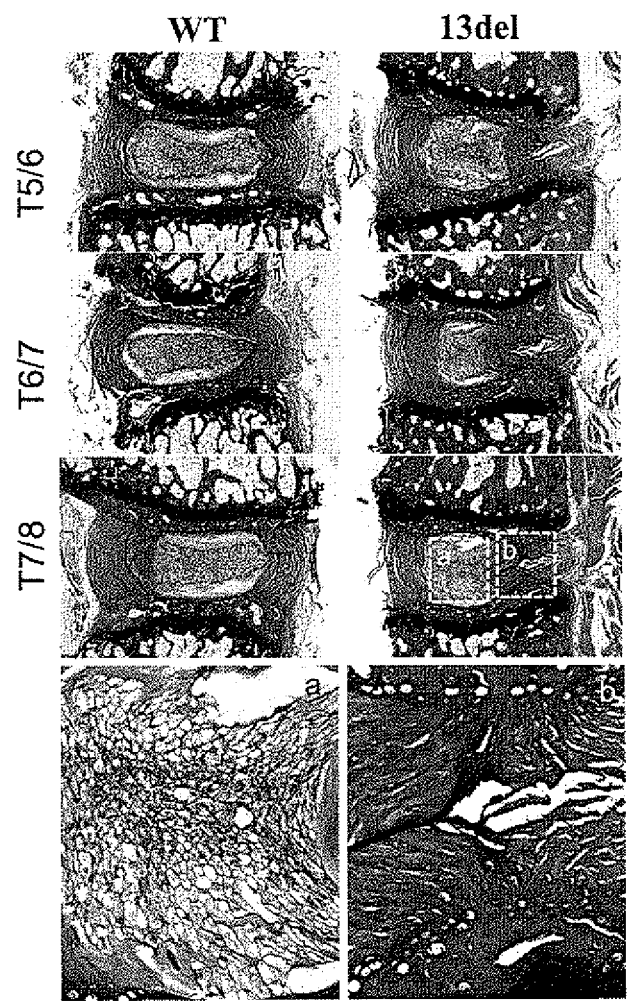
Figure 10E:
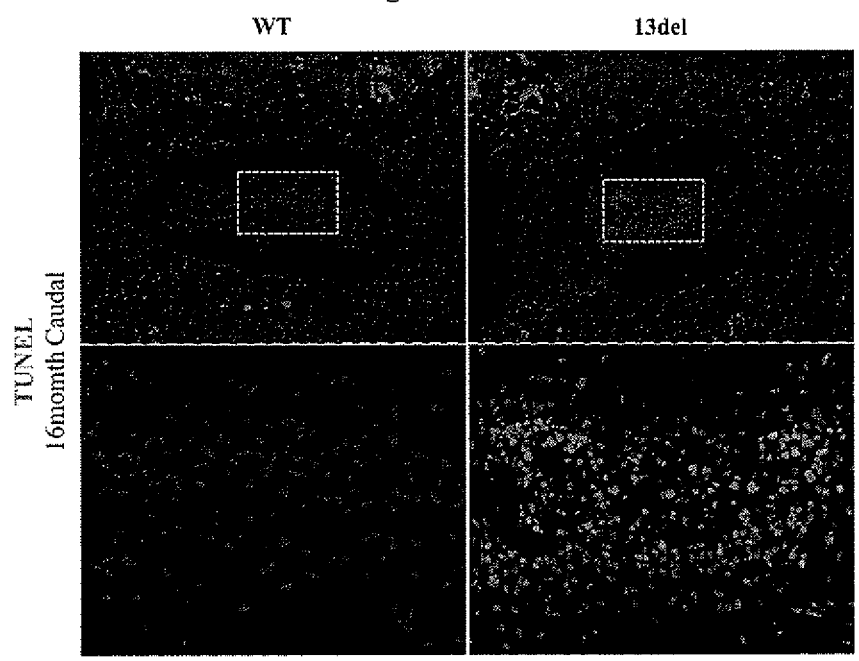
Figure 10F:
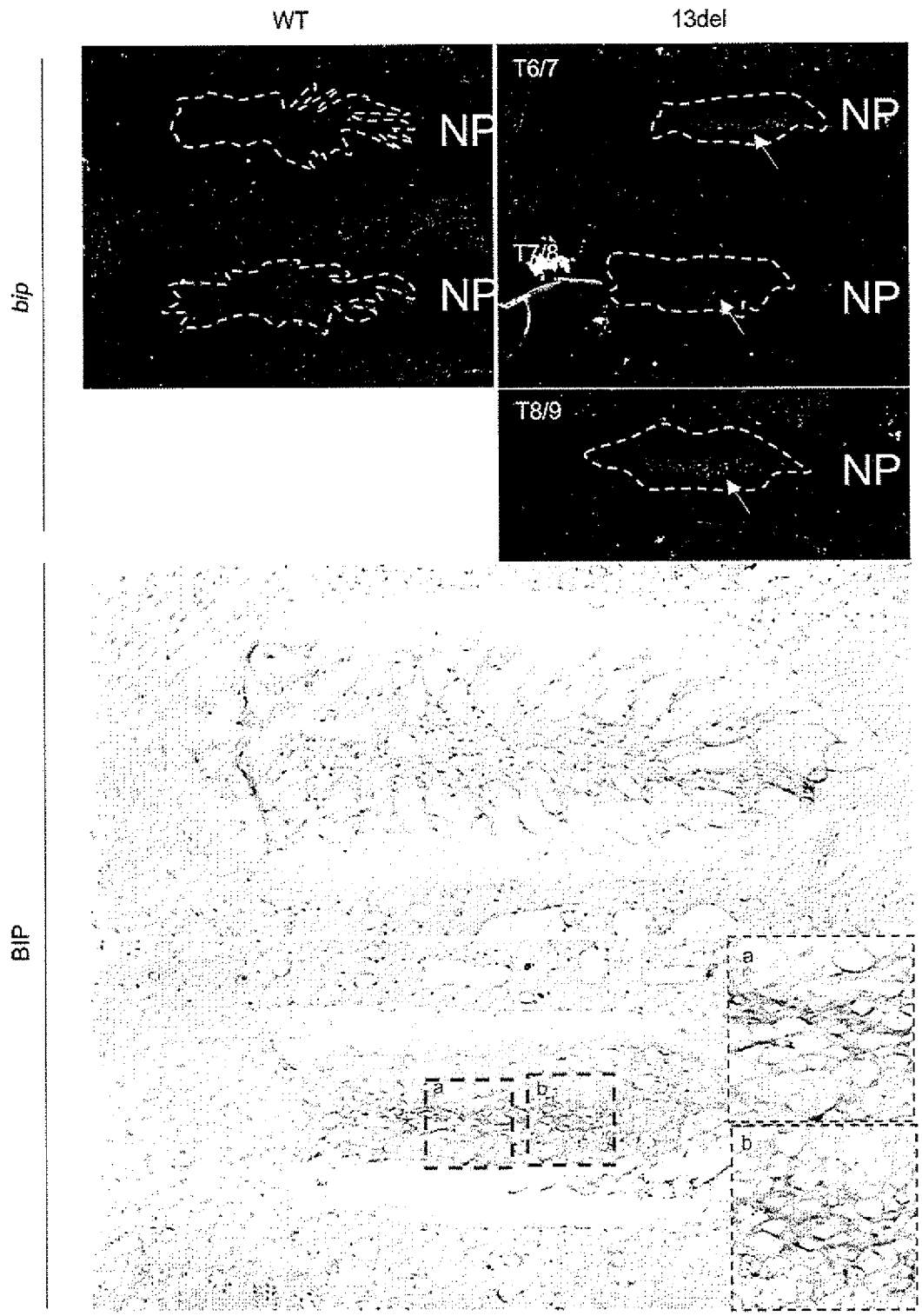
Figure 10G:
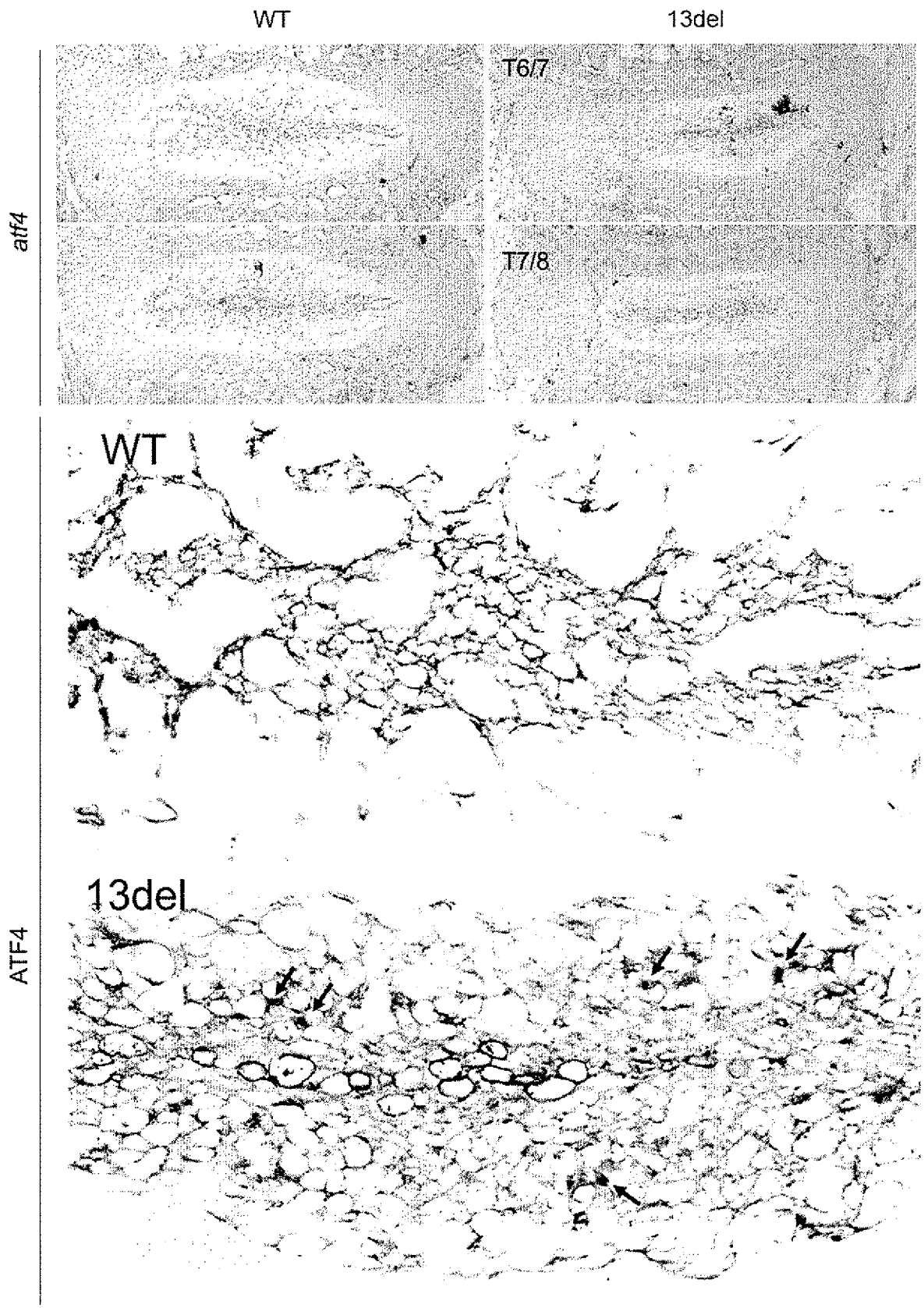
In FIG. 10G, although the transcriptional expression level of Atf4 is not changed, the protein level of ATF4 is significantly upregulated in 6-month 13del NP, indicating the contributory regulation of ISR.
Figure 10H:
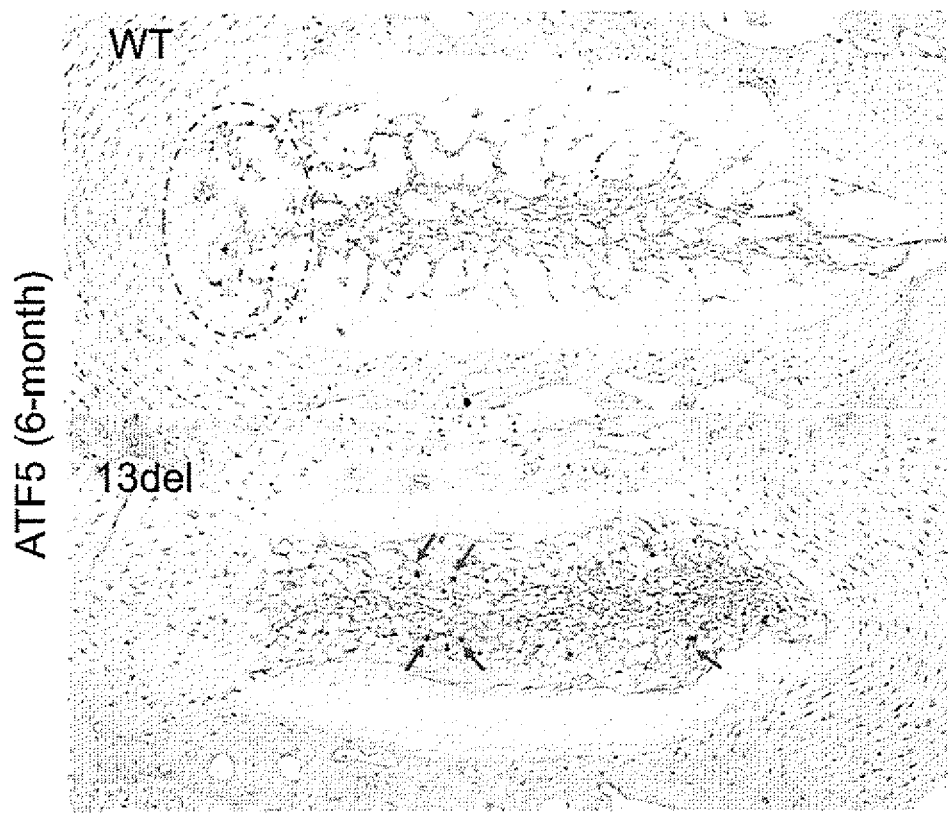
In FIG. 10H, the activation of ATF5, the vital transcription factor of mitochondria-dependent oxidative stress response, can be observed in 6-month 13del NP, indicating the induction of oxidative stress.

The expanded and irregular endplates can be observed in 13del mice at early p10 and p20 stage (FIG. 8L-8N). Concomitantly, the nucleus pulposus (NP) were swollen in appearance and there were irregularities in the inner AF (iAF) and endplate boundaries, with chondrocyte-like cells present at NP-AF and endplate boundaries (FIG. 10B). As a consequence, the tail intervertebral disc (IVD) of 13del mice exhibited significant characteristics of disc degeneration at adult stages (FIG. 10C), including altered NP structure and matrix, loss of NP/AF boundary, disc bulging, widening of the AF interlamellar space and the inward bulging of AF lamellae and consequently fissure (FIG. 10D). Interestingly, excessive cell death can be observed in 13del degenerated disc at 16-month stage, consistent with human IDD studies (84) (FIG. 10E). It is notable that volume of vascular canals in subchondral region between spinal growth plate and endplate significantly decreased in 13del disc (FIG. 10D), indicating the importation of oxygen and/or nutrition from endplate to NP and exportation of metabolites from NP to endplate might be lowered, consequently inducing integrated stress response. Consistently, the transcriptional and translational upregulation of BIP, the essential ER stress sensor, can be observed in core region of 13del degenerated NP (FIG. 10F). Concomitantly, the protein level of ATF4 is upregulated, while the transcriptional expression level of ATF4 is not changed (FIG. 10G). Strikingly, ATF5, the key sensor and signal transducer of mitochondria-related oxidative stress is also significantly upregulated in 13del degenerated NP. Taken together, these data strongly suggest the induction of multiple stresses in 13del NP (FIG. 10H).

Figure 10I:
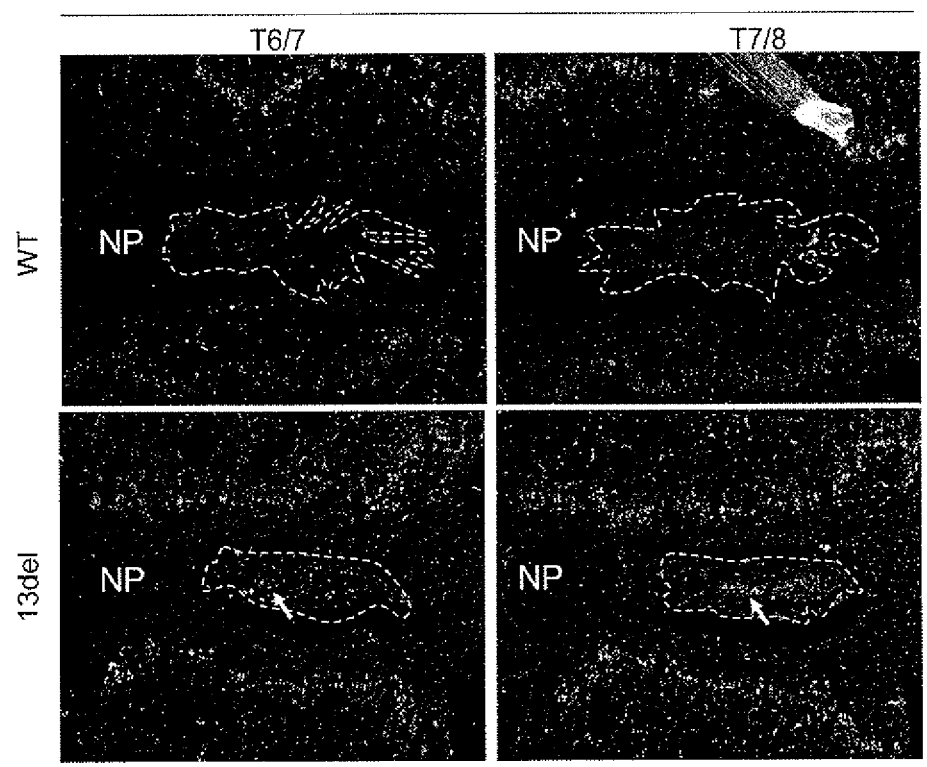
In FIG. 10I, in WT control, the peripheral NPC highly expressed Sox9 and the level became much lower in cells within core region. However, as the consequence of induction of stress in 6-month 13del NP, the cell fate of NP cell was affected, indicating by the ectopic expression of Sox9 in cells within the NP core region.
Figure 10J:
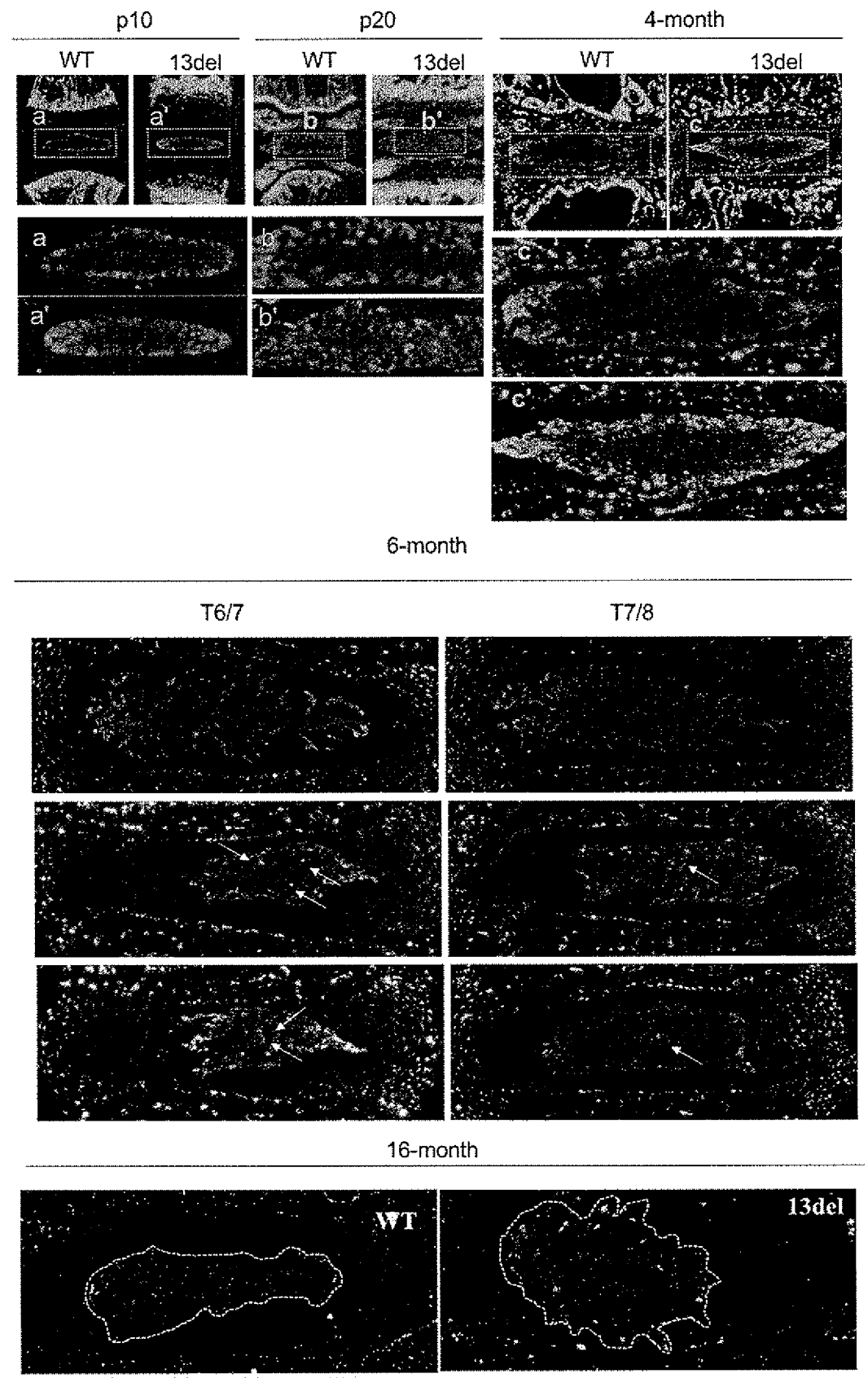
In FIG. 10J, OPN, as a major component of NP extracellular matrix, highly expressed in peripheral NPCs at young stage (p10, p20 and 4-month stages), diminished the expression level as maturation (6-month stage) and became absent at elderly stage (16-month stage). However, in 13del NP, not only the persistently upregulation in peripheral NPCs but also the ectopic expression of Opn in NPCs within the NP core region can be observed. Moreover, at elderly 16-month stage, the Opn$^+$ cells still can be detected.
Figure 10K:
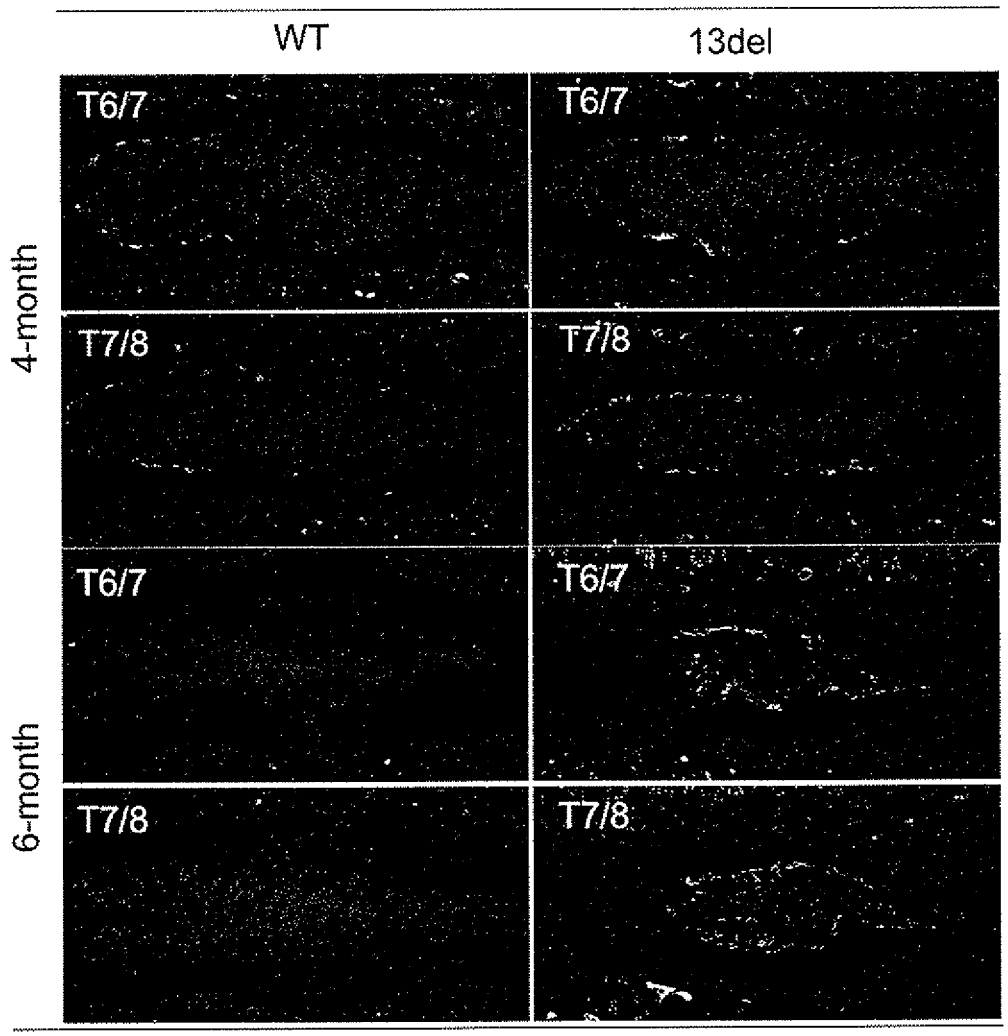
In FIG. 10K, similar to Opn, α-SMA marked the peripheral NPC in WT at young stage (4-month stage) but became absent at 6-month stage, while this marker persistently expressed in 13del peripheral NPCs and ectopic expressed in core NPCs.

Interestingly, the elevated stress response in 13del NP is accompanied by significant cell fate change, implied by the ectopic expression of Sox9 (FIG. 10I). On the other hand, disrupted matrix deposition in NP could be an important characteristic of degenerative changes. In 13del lumbar NP, the ectopic upregulation of Opn was observed at from p10 to 16-month stages (FIG. 10J). Moreover, the WT peripheral NP cells were found to be α-SMA$^+$ at young stage (4-month), but became absent of it at 6-month stage. However, in 13del degenerated NP, the peripheral NP cells persistently expressed α-SMA at 6-month stage and ectopic expression of this factor in core region of NP can also be observed (FIG. 10K).

Figure 10L:
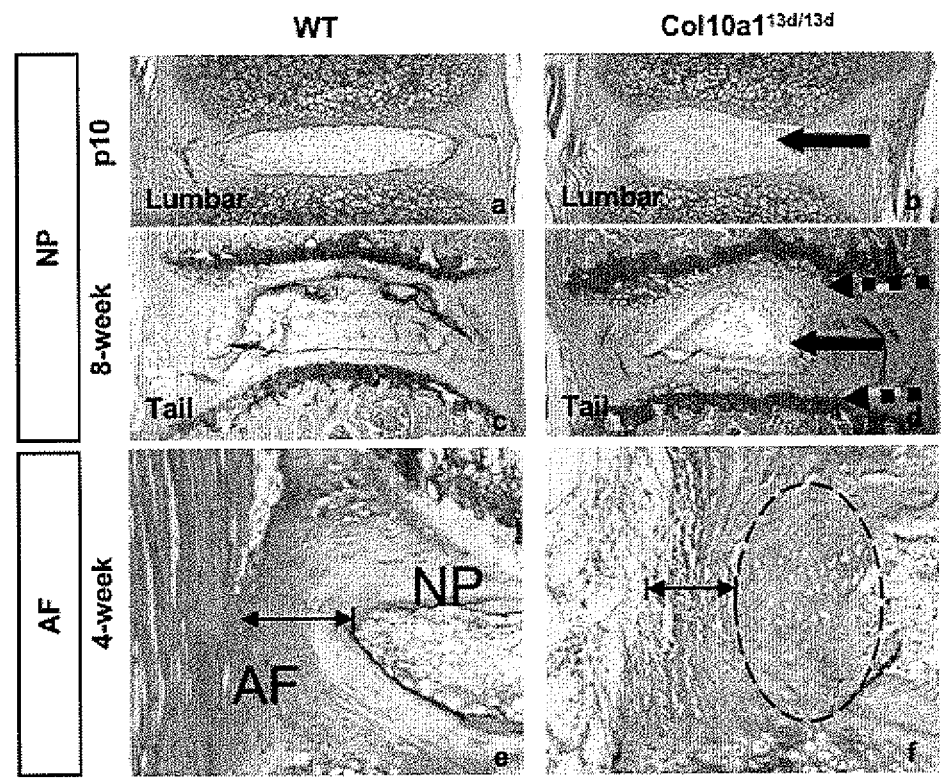
In FIG. 10L, the 13del-KI mice exhibit similar irregularities in IVD at p10 and 4-week stages, including accumulation of chondrocyte-like cells in the inner annulus fibrosus (iAF) (dashed circle in panel f), NP swelling (arrows in the middle of panels a and d) and irregular endplates (upper and lower dashed arrows in panel d).

Spinal changes were also observed in 13del-KI mice, including shortened vertebral bodies throughout the spine, disc space narrowing and similar irregularities of iAF (4-weeks-old mice) (FIG. 10L).

These findings suggest 13del and 13del-MCDS mice could be used to model changes in the IVD from activation of ER stress in hypertrophic chondrocytes of the cartilage endplate.

ISRIB Prevents the Molecular Changes in the 13Del IVD

Figure 11A:
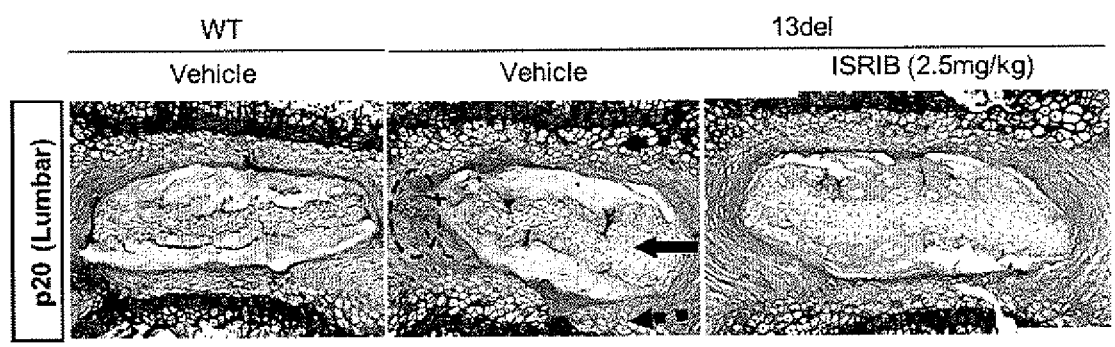

As abovementioned, ISRIB treatment in 13del mice reduced the deformities in growth plates of axial skeleton, with reduced HZ expansion and decreased number of Sox9$^+$ and Col2a1$^+$ premature cells in tail intervertebral disc growth plates (FIG. 8L-8N). In addition, after 20-days ISRIB treatment, the iAF was more regular in ISRIB-treated 13del mice, with fewer chondrocyte-like cells present (FIG. 11A).

Figure 11B:
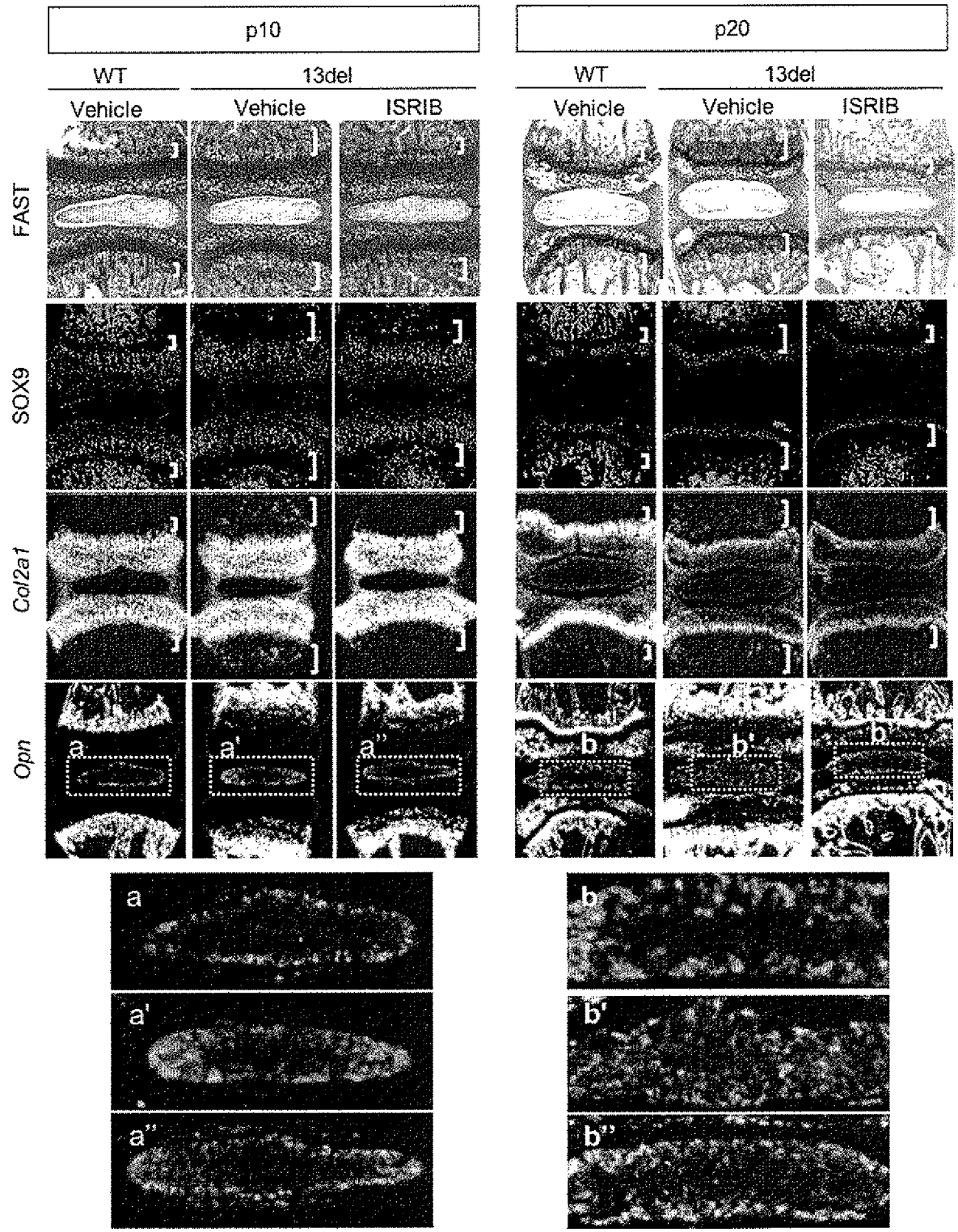
Figure 11C:
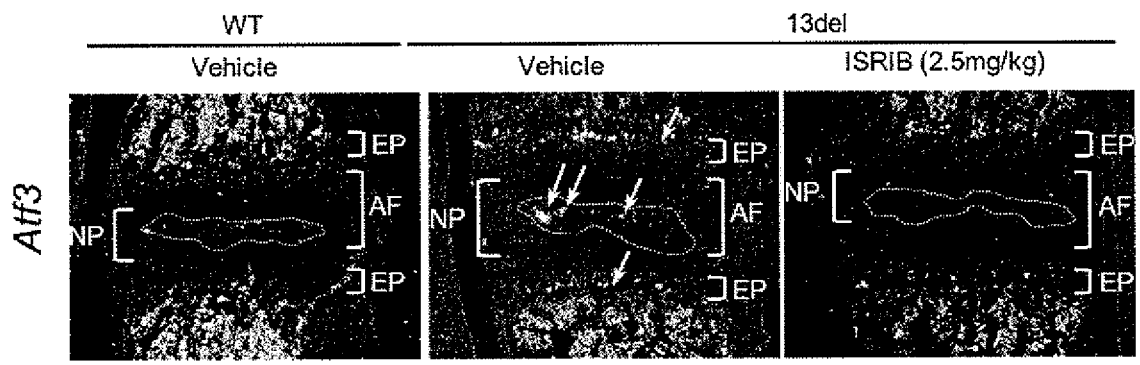

Disrupted matrix deposition in NP could be an important characteristic of degenerative changes. In 13del lumbar NP, the ectopic upregulation of Opn was observed at p10, p20 and 16-month stages (FIGS. 11B and 11C). Strikingly, 20-days treatment of ISRIB greatly reduced the ectopic NP expression of Opn (FIG. 11C), which may prevent the consequent NP degeneration in later stage.

Multiple stresses can activate the integrated stress response, in which ATF4 directly transactivates another important transcription factor ATF3. In 13del lumbar IVD, ATF3 is significantly activated not only in HCs in the growth plate and endplate, but also in the NP. Notably, the activation of ATF3 can only be observed in L3-L6, the region mostly affected by spine bending caused by lumbar lordosis. This finding strongly suggests the correlation between spine alignment and the onset of IDD. After the ISRIB treatment, no Atf3+ cell can be detected in L3-L6 NP, nor growth plates or endplates (FIG. 11D).

Hypoxia Stress in 13Del MCDS Mice

The ISR is activated by many cellular stresses including oxidative, nutritional and hypoxic. HIF pathway activation can be a consequence of UPR, and PERK pathway is also at the heart of hypoxia stress signaling pathway (18). In 13del HCs, HIF1α and its associated or downstream factors were upregulated (Table 3).

TABLE 3

Hypoxia stress is triggered in 13del HCs.

| | | | | | | |
|---|---|---|---|---|---|---|
| Aars | Bcat1 | Cth | Gdf15 | Mafk | Plaur | Serpine1 |
| Adm | Bnip3 | Dsp | Gja1 | Malat1 | Ppp1r13l | Slc2a1 |
| Ak3l1 | Cdk2ap2 | Egln1 | Gpt2 | Mgea5 | Psph | Slc7a5 |
| Aldoc | Cebpb | Eif4a1 | Grpel1 | Mthfd11 | Riok3 | Stc2 |
| Asns | Cebpd | Fn1 | Herpud1 | Ndrg1 | Rlf | Tmem158 |
| Atf3 | Cited2 | Gadd45a | Ier3 | Nfil3 | Sars | Tmepai |
| Atf5 | Creb3l2 | Gadd45b | Junb | Pfkp | Sdc4 | Trib3 |

Figure 12A:
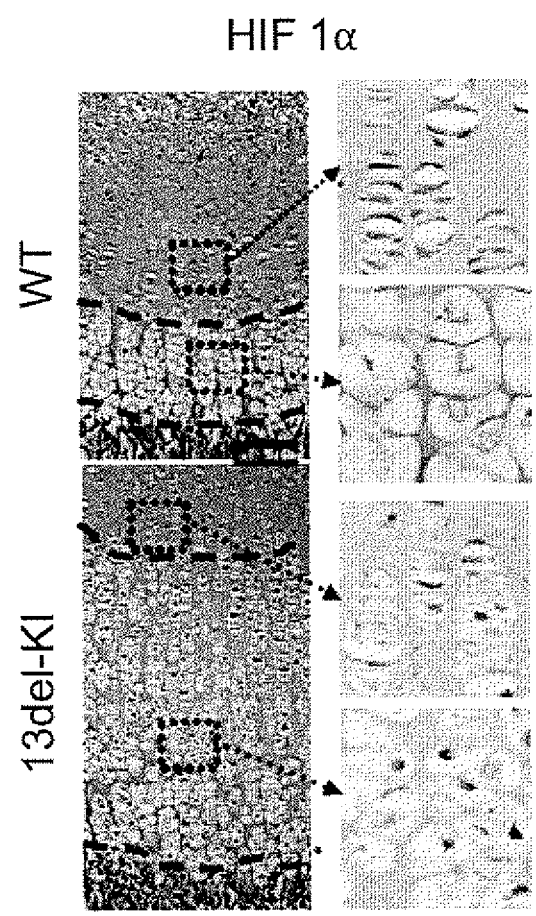
FIGS. 12A-12G show that hypoxia stress is triggered in 13del MCDS mice.
Figure 12B:
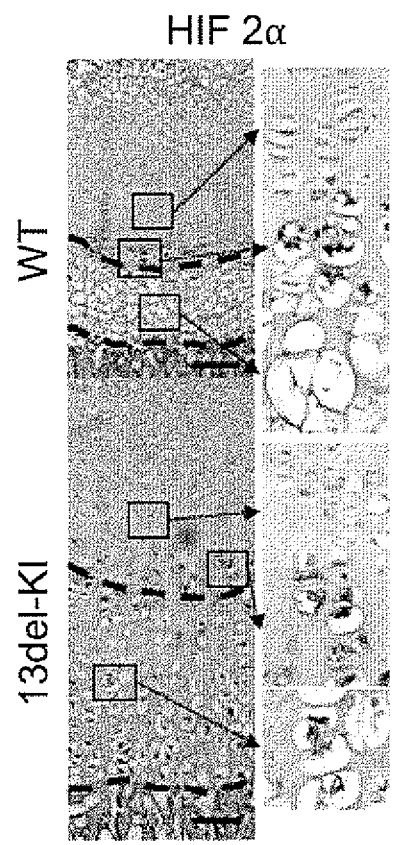

In 13del-KI mice, HIF1α and HIF2α immunohistochemistry staining showed a strong accumulation of HIFs proteins in hypertrophic chondrocytes when compared with wild-type. In postnatal 10-day-old growth plate, HIF1α is detected in proliferating chondrocytes and resting chondrocytes, but not in hypertrophic chondrocytes. In the 13del-KI littermates, HIF1α is not only accumulated in proliferating chondrocytes, but also in the hypertrophic chondrocytes from the upper to lower hypertrophic zones (FIG. 12A). HIF2α is predominantly found in pre-hypertrophic chondrocytes in wild-type 10-day-old mice but not much in hypertrophic chondrocytes. However, it can be clearly detected in both pre-hypertrophic chondrocytes and hypertrophic chondrocytes in 13del-KI littermates (FIG. 12B).

Figure 12C:
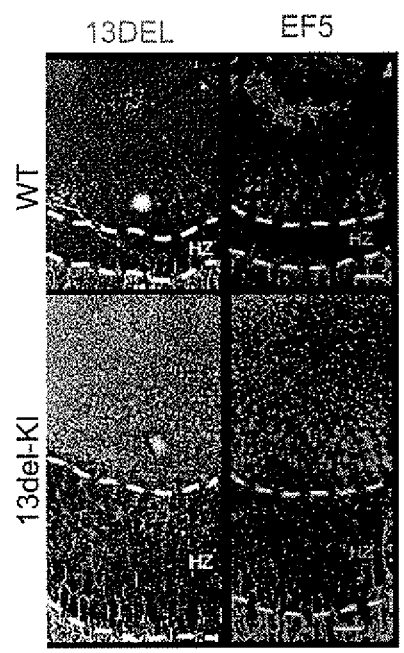
Figure 12D:
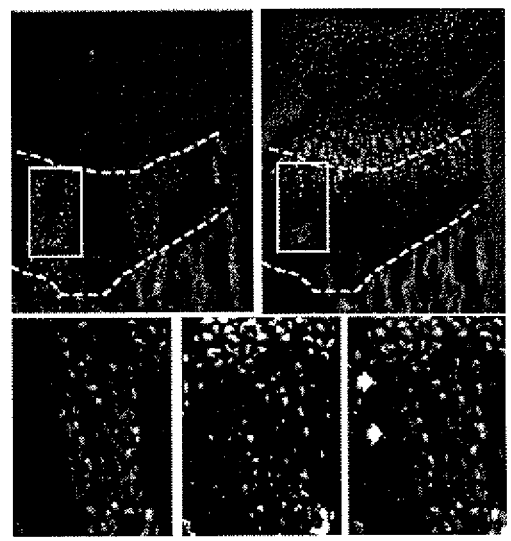
Figure 12E:
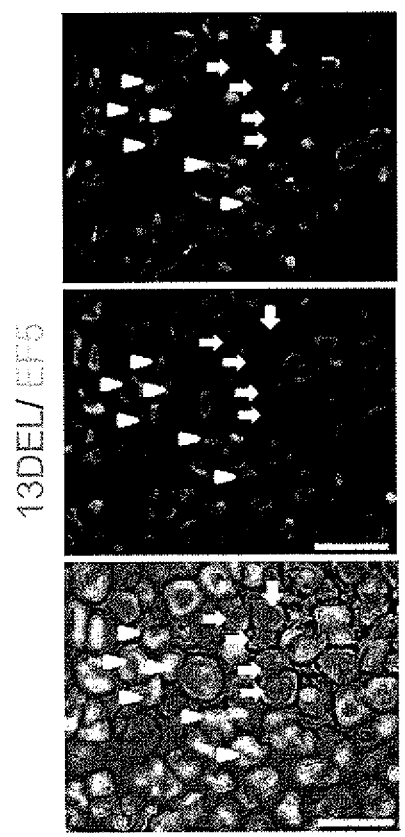

EF5 assay, which detects hypoxic cells in vivo system, was then performed in P10 littermates of WT and 13del-KI mice. The 13del immunofluorescence staining shows that almost all the hypertrophic chondrocytes are expressing mutant collagen type X in 13del-KI growth plate (FIG. 12C). Few EF5 bindings were detected in the lower hypertrophic zone in 13del-MCDS tibia proximal growth plate, nor in the whole hypertrophic zone in wild-type. However, the upper and middle hypertrophic zones of the growth plate in 13del-KI mice bound EF5 significantly more than the hypertrophic zone in wild-type (FIG. 12D). These data indicate that chondrocytes on the upper and middle hypertrophic zones of 13del-KI are under lower oxygen tension compared to wild-type.

To assess the relative contribution of intrinsic and extrinsic response in the activation of the hypoxia response, EF5 was administrated by intraperitoneal injection into a P9 GFP/13del-KI chimera mice and sacrificed 4 h later. In the distal tibia growth plate, columns of 13del positive hypertrophic chondrocytes can be detected with the 13del antibody indicating these are derived from clonal expansion of MCDS proliferating chondrocytes that are differentiated to hypertrophic chondrocytes. EF5 positive cells are highly correlated with the cells expressing 13del protein (FIG. 12D). This strong correlation of 13del expressing cells and EF5 staining positive cells are also observed in the hypertrophic chondrocytes of the talus cartilage (FIG. 12 E). ER stress is highly correlated with EF5 staining, suggesting the "hypoxic" signal is an intrinsic effect of 13del-KI cells.

Figure 12F:
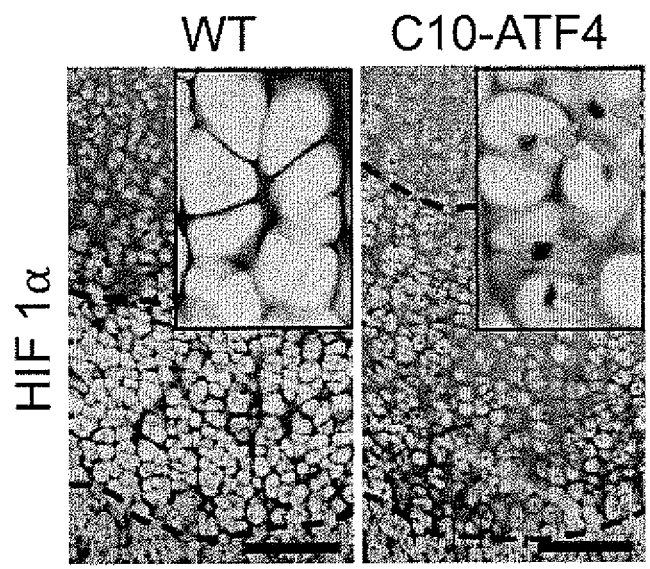
Figure 12G:
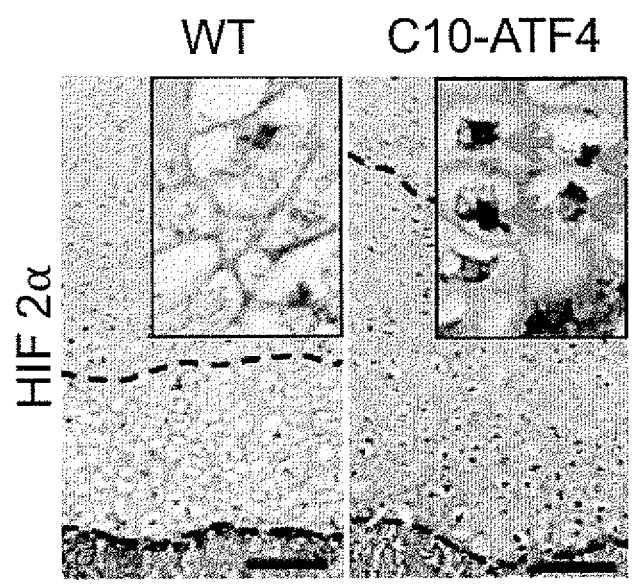

As abovementioned, ATF4 is regulated at the translational level in ISR under anoxic and hypoxic conditions, mediates in part by the unfolded protein response and is an important regulator of cell fate. Therefore, ATF4 could be the essential link between ER stress and hypoxic stress. In C10-ATF4 mice, HIF1α can be detected in proliferating chondrocytes as well as the hypertrophic chondrocytes in the expanded hypertrophic zone in C10-ATF4 transgenic mice, while HIF1α can be only detected in proliferating chondrocytes but not in hypertrophic chondrocytes in wild-type mice as previously shown (FIG. 12F). Furthermore, HIF2α was also detected in the same region of the expanded hypertrophic chondrocytes in C10-ATF4 transgenic mice (FIG. 12G), suggesting both HIF proteins are responding similarly to the ectopic expression of ATF4. These findings suggest that up-regulation of ATF4 as part of the UPR could be involved in the regulation of HIF proteins in hypertrophic chondrocytes under ER stress.

Identified Putative ATF4 Binding Region on Sox9 Topologically Associated Domains (TAD)

Chromosome conformation capture methods (capture Hi-C and 4C-seq methods) have been used to identify SOX9 subchromosomal structures of higher-order chromatin interactions called topologically associated domains (TADs) (85), which are separated by boundary regions that have comparatively high levels of transcriptional repressor CCCTC-binding factor (CTCF) (86). The TADs subdivide the SOX9 genome into discrete regulatory units, to which the majority of observed interactions between promoters and enhancers are restricted (87, 88).

Figure 13D:
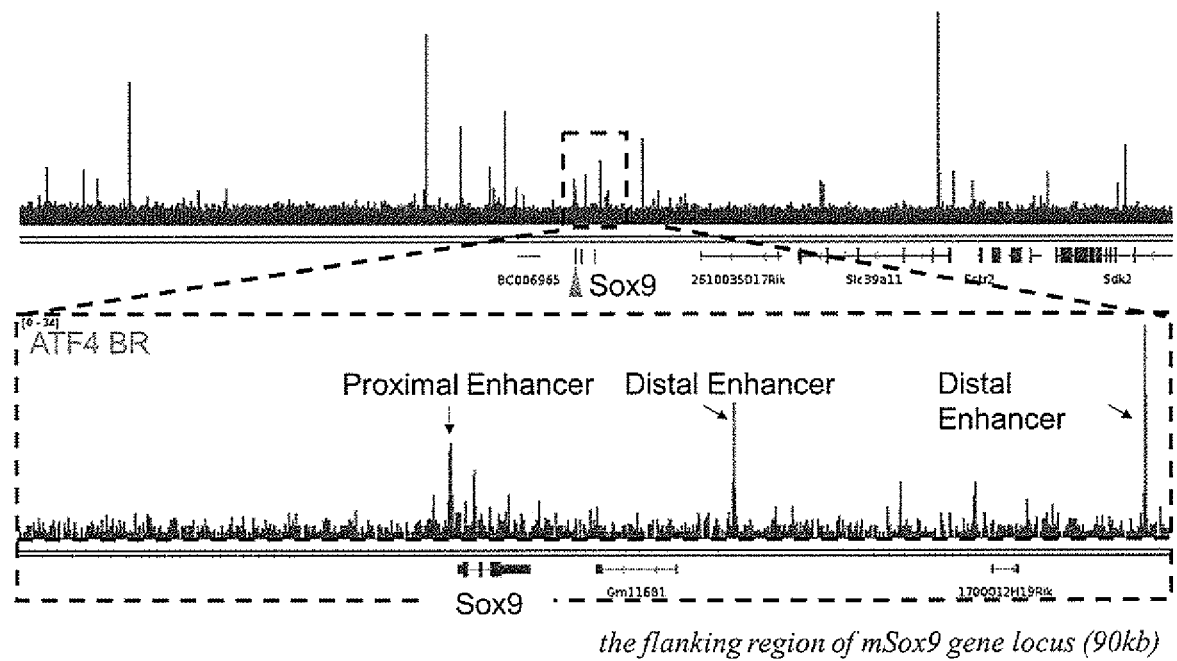

Both human SOX9 (hSOX9) and mouse Sox9 (mSox9) are located within the boundary region between 2 sub-TAD domains in human and mouse genome respectively, and share a highly conserved TAD pattern (FIG. 13A) in embryonic stem cells. Consistent to that, the CTCF insulator binding regions were found in both human SOX9 and mouse Sox9 gene locus (FIGS. 13B and C). On the other hand, a total of 25 putative ATF4 binding enhancer regions were identified in the mouse Sox9-TAD domain (Table 1) by published ATF4 ChIP-seq (45), and FIG. 13D demonstrates an example of putative ATF4 binding enhancer region of mSox9. Taken together, these findings strongly suggest that ISR-induced ATF4 may regulate the Sox9 expression by enhancers.

Methods

Mice Breeding

The 13del transgenic mice were maintained in F1 (C57BL/6×CBA) background. The 13del-KI mice were maintained in C57BL/6 background. The Chop-null mice and Fgf21-null mice were reported previously (13, 89). The Sox9-flox mice was a gift from Prof. Andreas Schedl' lab (Institute of Biology Valrose, France) (60). The C10-ATF4 transgenic mice were generated by injecting a BAC vector (Col10a1-ATF4-IRES-EGFP) into the F1 zygotes and maintained in F1. Mice were genotyped by PCR using primers (5'-CAGATCAGTGATGGGCTATG-3' (SEQ ID NO: 30) and 5'-GAACCACCTGAGAAGGCAGATT-3' (SEQ ID NO: 31). Animal care and experiments performed were in accordance with the protocols approved by the Committee on the Use of Live Animals in Teaching and Research of the University of Hong Kong.

Generation of wtGFP/13Del-KI Chimeric Mice

GFP (homozygous) and 13del-KI homozygous (M/M) morula-stage embryos (2.5 dpc) were collected, zona pellucida was then removed by acid tyrode and the embryos were washed and aggregated in 1:1 ratio at 37° C. overnight in an aggregation plate. Successful aggregated embryos were transferred to a pseudopregnant ICR foster mother.

EF5 Distribution Analysis

To study EF-5 distribution, P10 mice were injected with 10 mM EF5 at 1% of body weight and staining was performed as described previously (90, 91).

RNA Preparation and Microarray Analysis

The proximal part of tibia was embedded in O.C.T. compound (ebsciences, USA) for cryosection. Transverse sections (5 μm thick) were cut and pooled into fractions consisting of 10 sections per fraction to ensure separation of each cell type in the growth plates before lysed in Trizol® reagent (Invitrogen). Total RNA were extracted and hybridized to Mouse Genome 430 2.0 Gene Chip (Affymetrix). Gene expression data for each sample in triplicate were normalized using Robust Multi-chip Average (RMA) algorithm in R Bioconductor package. The k-Means Clustering algorithm (92, 93) was used to identify the distinct expression patterns of genes in WT and 13del growth plates. The Gene Ontology analysis was performed for each cluster of genes by using the Gene Ontology database (94) and the David Web Tools (95).

HOMER Motif Discovery

The DNA binding motif enrichment analysis was performed by using HOMER software package (96). The DNA sequences flanking the genes' transcription start sites 2 kb up- and downstream were extracted from the mouse reference genome assembly (mm9). The HOMER, the TRANSFAC (97) and the ISMARA (98) transcription factor databases were integrated to create the TF binding motif library for screening. The DNA sequences of the interrogated gene sets were compared with those extracted from the remainder gene sets to identify the differentially enriched DNA binding motifs and the TFs.

ChIP-Sequencing Data Analysis

The ATF4 and CHOP ChIP-sequencing datasets (45) were downloaded from the GEO database (GSE35681). The DNA sequences were aligned to the mm9 mouse reference genome assembly with Bowtie program (99). The analysis of coverage signal intensity and peak detection were performed by using Picard toolkit of Broad Institute (MIT) (https://tldrlegal.com/license/mit-license). The binding peaks located within 10 kb up or downstream of the TSS in each target gene were identified for statistical analysis in each cluster.

Histological and Immunofluorescence Analyses

Limbs were fixed in 4% PFA, followed by demineralization in 0.5M EDTA (pH 8.0) prior to embedding in paraffin. Slides were stained with Alcian Blue for cartilage matrix and Fast Red for nuclei. Immunofluorescence was performed using antibodies against ATF4 (sc-200, Santa Cruz), ATF3 (HPA001562, Sigma), CHOP (sc-575, Santa Cruz), GADD34 (sc-825, Santa Cruz), FGF21 (42189, AIS) and Sox9 (AB5535, Millipore).

FAST Staining

FAST staining refers to a multidye staining procedure using fast green, Alcian blue, Safranin-O, and tartrazine and was performed as described previously (100).

In-Situ Hybridization

In-situ hybridization was performed as previously described (101), using [$^{35}$S]UTP-labeled ribopobes for Col10a1, Col2a1, Bip, 13del(10), Ihh (from A. McMahon), Sox9 (102) and the PTHrP receptor (Ppr) (from H. Kronenberg). The probes for Atf4, Atf3, Chop, Ero1l and Fgf21 were mouse cDNA fragments, generated by RT-PCR from growth plate total RNA. The primers used are as follows: Atf4, 5'-GAGGTGGCCAAGCACTTGAAA (SEQ ID NO: 32) and 5'-GAACCACCTGGAGAAGGCAGATT (SEQ ID NO: 33); Atf3, 5'-GCTTCCCCAGTGGAGCCAAT (SEQ ID NO: 34) and 5'-CCACCTCTGCTTAGCTCTGCAAT (SEQ ID NO: 35); Chop, 5'-ATGAGGATCTGCAG-GAGGTCCTGTC (SEQ ID NO: 36) and 5'-GATGCC-CACTGTTCATGCTTGT (SEQ ID NO: 37); Ero1l, 5'-AAGACTACAAAAGCTTCTTG (SEQ ID NO: 38) and 5'-AAGAATTCTCATCGAAGTGCAA (SEQ ID NO: 39); and Fgf21, 5'-CAGGGTCATTCAAATCCTG (SEQ ID NO: 40) and 5'-AGGAATCCTGCTTGGTCTTG (SEQ ID NO: 41).

TUNEL Assay

Apoptotic cells in the growth plate of examined animals were detected by in situ terminal deoxynucleotidyltransferase deoxyuridine triphosphate nick end labeling (TUNEL) assay using the In Situ Cell Death Detection Kit (Roche) following the manufacturer's instructions.

Chromatin Immunoprecipitation (ChIP) Assay

The protocol used for ChIP was adapted from the instructions of ChIP Assay Kit (Millipore). Culture cells or limbs dissected from E15.5 WT and C10-ATF4 embryos were homogenized and crosslinked. DNA was sonicated and immunoprecipitated with rabbit anti-ATF4 (sc-200, Santa Cruz Biotechnology) or rabbit anti-CHOP (s-575, Santa Cruz Biotechnology) antibody. The pull-down DNA was purified and analyzed by PCR.

Protein Extraction and Immunoblot Analysis

Cartilages isolated from the mice were pulverized in liquid nitrogen and then lysed with RIPA buffer. The lysate was subjected to SDS-PAGE under reducing conditions and probed with FGF21 and beta-actin antibody.

Dual Luciferase Reporter Assay

Luciferase assays were conducted using a dual luciferase reporter assay kit (Promega), according to the manufacturer's protocol. Different promoter fragments of Sox9 or Fgf21 were cloned into pGL3-basic vector (Promega) to drive the expression of firefly luciferase. ATDC5 or NIH3T3 cells were plated at $2 \times 10^4$ cells/well in 24-well plates. After 18-hours incubation, the cells were transfected with tested constructs with Renilla luciferase vector, which served as an internal control. Data presented are ratios of Luc/Renilla activity from at least three different experiments and each experiment was performed in triplicate for each DNA sample.

Quantitative PCR

Quantitative PCR was performed using SYBR-Green master mixture according to the manufacturer's instruction (Takara). Appropriate amounts of cDNA (or DNA) and primers were mixed with distilled water up to 10 μl and combined with equal amount of SYBR-Green master mixture. The reaction was run on the StepOne Real Time PCR system (Applied Biosystems, A&B). The Ct (cycle threshold) is defined as the cycle number required for the fluorescent signal to cross the threshold. The relative expression levels of target genes are calculated by normalizing to the expression level of GAPDH using delta-delta-Ct (Relative expression level=$2^{\wedge}-(Ct_{target}-Ct_{Gapdh})$). Melting curve was also measured to detect the specificity of the primers.

ISRIB Treatments

ISRIB (SML0843, Sigma) was dissolved in DMSO to make a 5 mg/ml stock and stored at 4-degree. Animals were intraperitoneally injected with ISRIB ((103, 104) (2.5 mg/kg, diluted in 0.9% saline) or vehicle (5% DMSO in saline) from E13.5 till p20 stage. The animals were collected at p10 and p20 stages for further analysis.

Radiography of Mouse Skeleton

Mice were anesthetized before radiography using digital Faxitron system (UltraFocus) at 20 kVA for 5 second exposure.

Statistical Analyses

No statistical methods were used to predetermine sample size. Statistical analyses used are detailed in the figure legends. Unpaired two tailed Student's t-test was used to establish statistical significance. For growth analysis, two tailed Mann-Whitney U-test was used. P<0.05 was considered statistically significant.

Data Availability

All primary microarray data are deposited into Gene Expression Omnibus (GEO) website (Accession Number GSE99306).

REFERENCES

1. P. T. Siegel, R. Clopper, B. Stabler, Psychological impact of significantly short stature. *Acta paediatrica Scandinavica. Supplement* 377, 14-18; discussion 19 (1991).
2. S. Thompson, T. Shakespeare, M. J. Wright, Medical and social aspects of the life course for adults with a skeletal dysplasia: a review of current knowledge. *Disability and rehabilitation* 30, 1-12 (2008).
3. C. W. Lie, W. Chow, Limb lengthening in short-stature patients using monolateral and circular external fixators. *Hong Kong medical journal=Xianggang yi xue za zhi/Hong Kong Academy of Medicine* 15, 280-284 (2009).
4. T. S. Lisse et al., ER stress-mediated apoptosis in a new mouse model of osteogenesis imperfecta. *PLoS genetics* 4, e7 (2008).
5. B. R. Olsen, Mutations in collagen genes resulting in metaphyseal and epiphyseal dysplasias. *Bone* 17, S45-S49 (1995).
6. F. Suleman et al., A novel form of chondrocyte stress is triggered by a COMP mutation causing pseudoachondroplasia. *Hum Mutat* 33, 218-231 (2012).
7. K. A. Pirog, Y. Katakura, A. Mironov, M. D. Briggs, Mild myopathy is associated with COMP but not MATN3 mutations in mouse models of genetic skeletal diseases. *PloS one* 8, e82412 (2013).
8. M. D. Briggs, K. L. Chapman, Pseudoachondroplasia and multiple epiphyseal dysplasia: Mutation review, molecular interactions, and genotype to phenotype correlations. *Human Mutation* 19, 465-478 (2002).
9. K. Y. Tsang, D. Chan, J. F. Bateman, K. S. Cheah, In vivo cellular adaptation to ER stress: survival strategies with double-edged consequences. *Journal of cell science* 123, 2145-2154 (2010).
10. K. Y. Tsang et al., Surviving endoplasmic reticulum stress is coupled to altered chondrocyte differentiation and function. *PLoS Biol* 5, e44 (2007).
11. O. Makitie et al., Schmid type of metaphyseal chondrodysplasia and COL10A1 mutations-findings in 10 patients. *Am J Med Genet A* 137A, 241-248 (2005).
12. M. Ridanpää et al., Genetic changes in the RNA components of RNase MRP and RNase P in Schmid metaphyseal chondrodysplasia. *Journal of Medical Genetics* 40, 741-746 (2003).
13. H. Zinszner et al., CHOP is implicated in programmed cell death in response to impaired function of the endoplasmic reticulum. *Genes & development* 12, 982-995 (1998).
14. C. Hetz, E. Chevet, H. P. Harding, Targeting the unfolded protein response in disease. *Nat Rev Drug Discov* 12, 703-719 (2013).
15. S. Nundlall et al., An unfolded protein response is the initial cellular response to the expression of mutant matrilin-3 in a mouse model of multiple epiphyseal dysplasia. *Cell Stress & Chaperones* 15, 835-849 (2010).
16. K. L. Posey et al., Chondrocyte-specific pathology during skeletal growth and therapeutics in a murine model of pseudoachondroplasia. (2014).
17. D. T. Rutkowski, R. S. Hegde, Regulation of basal cellular physiology by the homeostatic unfolded protein response. (2010).
18. K. Pakos-Zebrucka et al., The integrated stress response. *EMBO reports* 17, 1374-1395 (2016).
19. C.-Q. Zhao, Y.-H. Zhang, S.-D. Jiang, L.-S. Jiang, L.-Y. Dai, Both endoplasmic reticulum and mitochondria are involved in disc cell apoptosis and intervertebral disc degeneration in rats. *Age* 32, 161-177 (2010).
20. D. Xu et al., Hydrogen sulfide protects against endoplasmic reticulum stress and mitochondrial injury in nucleus pulposus cells and ameliorates intervertebral disc degeneration. *Pharmacological Research* 117, 357-369 (2017).
21. T. Oosterhuis et al., Early rehabilitation after lumbar disc surgery is not effective or cost-effective compared to no referral: a randomised trial and economic evaluation. *Journal of Physiotherapy* 63, 144-153.
22. H. Kanazawa et al., Efficacy of growth hormone therapy for patients with skeletal dysplasia. *Journal of Bone and Mineral Metabolism* 21, 307-310 (2003).
23. S. Suzuki et al., Excessive reactive oxygen species are therapeutic targets for intervertebral disc degeneration. *Arthritis Research & Therapy* 17, 316 (2015).
24. A. Hiyama et al., Hypoxia Activates the Notch Signaling Pathway in Cells of the Intervertebral Disc: Implications in Degenerative Disc Disease. *Arthritis and rheumatism* 63, 1355-1364 (2011).
25. L. J. Smith, N. L. Nerurkar, K.-S. Choi, B. D. Harfe, D. M. Elliott, Degeneration and regeneration of the intervertebral disc: lessons from development. *Disease Models & Mechanisms* 4, 31-41 (2011).
26. A. G. Hadjipavlou, M. N. Tzermiadianos, N. Bogduk, M. R. Zindrick, The pathophysiology of disc degeneration. *Journal of Bone &amp; Joint Surgery*, British Volume 90-B, 1261 (2008).
27. H. S. An, K. Masuda, N. Inoue, Intervertebral disc degeneration: biological and biomechanical factors. *Journal of Orthopaedic Science* 11, 541-552 (2006).
28. I. C. Salaroglio et al., PERK induces resistance to cell death elicited by endoplasmic reticulum stress and chemotherapy. *Molecular Cancer* 16, 91 (2017).
29. L. R. Palam, J. Gore, K. E. Craven, J. L. Wilson, M. Korc, Integrated stress response is critical for gemcitabine resistance in pancreatic ductal adenocarcinoma. *Cell Death & Disease* 6, e1913 (2015).
30. P. Podszywalow-Bartnicka et al., Increased phosphorylation of eIF2α in chronic myeloid leukemia cells stimulates secretion of matrix modifying enzymes. *Oncotarget* 7, 79706-79721 (2016).
31. Y. Y. Ho, D. Lagares, A. M. Tager, M. Kapoor, Fibrosis [mdash]a lethal component of systemic sclerosis. *Nat Rev Rheumatol* 10, 390-402 (2014).
32. P. Cheresh, S.-J. Kim, S. Tulasiram, D. W. Kamp, Oxidative Stress and Pulmonary Fibrosis. *Biochimica et biophysica acta* 1832, 1028-1040 (2013).
33. R. M. Liu, K. A. Gaston Pravia, Oxidative stress and glutathione in TGF-β-mediated fibrogenesis. *Free Radical Biology and Medicine* 48, 1-15 (2010).
34. I. Cucoranu et al., NAD(P)H Oxidase 4 Mediates Transforming Growth Factor-β1-Induced Differentiation of Cardiac Fibroblasts Into Myofibroblasts. *Circulation Research* 97, 900 (2005).

35. G. H. Kim, J. E. Kim, S. J. Rhie, S. Yoon, The Role of Oxidative Stress in Neurodegenerative Diseases. *Experimental Neurobiology* 24, 325-340 (2015).
36. D. Lindholm, H. Wootz, L. Korhonen, ER stress and neurodegenerative diseases. *Cell Death Differ* 13, 385-392 (2006).
37. S. E. Patterson, C. N. Dealy, Mechanisms and models of endoplasmic reticulum stress in chondrodysplasia. *Developmental Dynamics* 243, 875-893 (2014).
38. Stela S. Palii, Michelle M. Thiaville, Y.-X. Pan, C. Zhong, Michael S. Kilberg, Characterization of the amino acid response element within the human sodium-coupled neutral amino acid transporter 2 (SNAT2) System A transporter gene. *Biochemical Journal* 395, 517-527 (2006).
39. J. Buenrostro, B. Wu, H. Chang, W. Greenleaf, ATAC-seq: A Method for Assaying Chromatin Accessibility Genome-Wide. *Current protocols in molecular biology/ edited by Frederick M. Ausubel ... [et al.]* 109, 21.29.21-21.29.29 (2015).
40. L. Nel-Themaat et al., Morphometric analysis of testis cord formation in Sox9-EGFP mice. *Developmental Dynamics* 238, 1100-1110 (2009).
41. L. Madisen et al., Transgenic mice for intersectional targeting of neural sensors and effectors with high specificity and performance. *Neuron* 85, 942-958 (2015).
42. E. Provost, J. Rhee, S. D. Leach, Viral 2A peptides allow expression of multiple proteins from a single ORF in transgenic zebrafish embryos. *genesis* 45, 625-629 (2007).
43. N. A. Kearns et al., Functional annotation of native enhancers with a Cas9-histone demethylase fusion. *Nat Meth* 12, 401-403 (2015).
44. L. Cong et al., Multiplex Genome Engineering Using CRISPR/Cas Systems. *Science (New York, N. Y)* 339, 819-823 (2013).
45. J. Han et al., ER-stress-induced transcriptional regulation increases protein synthesis leading to cell death. *Nat Cell Biol* 15, 481-490 (2013).
46. C. M. Oslowski, F. Urano, Measuring ER stress and the unfolded protein response using mammalian tissue culture system. *Methods in enzymology* 490, 71-92 (2011).
47. H. P. Harding et al., Regulated translation initiation controls stress-induced gene expression in mammalian cells. *Molecular cell* 6, 1099-1108 (2000).
48. H. Hojo, A. P. McMahon, S. Ohba, An Emerging Regulatory Landscape for Skeletal Development. *Trends Genet* 32, 774-787 (2016).
49. G. S. Hotamisligil, R. J. Davis, Cell Signaling and Stress Responses. *Cold Spring Harb Perspect Biol* 8, (2016).
50. P. Walter, D. Ron, The Unfolded Protein Response: From Stress Pathway to Homeostatic Regulation. *Science* 334, 1081 (2011).
51. K. Horiuchi, T. Tohmonda, H. Morioka, The unfolded protein response in skeletal development and homeostasis. *Cell Mol Life Sci* 73, 2851-2869 (2016).
52. A. Sudhakar et al., Phosphorylation of Serine 51 in Initiation Factor 2α (eIF2α) Promotes Complex Formation between eIF2α(P) and eIF2B and Causes Inhibition in the Guanine Nucleotide Exchange Activity of eIF2B. *Biochemistry* 39, 12929-12938 (2000).
53. T. L. Cameron et al., XBP1-Independent UPR Pathways Suppress C/EBP-beta Mediated Chondrocyte Differentiation in ER-Stress Related Skeletal Disease. *PLoS genetics* 11, e1005505 (2015).
54. W. Wang et al., Atf4 regulates chondrocyte proliferation and differentiation during endochondral ossification by activating Ihh transcription. *Development (Cambridge, England)* 136, 4143-4153 (2009).
55. V. Y. L. Leung et al., SOX9 Governs Differentiation Stage-Specific Gene Expression in Growth Plate Chondrocytes via Direct Concomitant Transactivation and Repression. *PLoS genetics* 7, e1002356 (2011).
56. L. Yang, K. Y. Tsang, H. C. Tang, D. Chan, K. S. Cheah, Hypertrophic chondrocytes can become osteoblasts and osteocytes in endochondral bone formation. *Proc Natl Acad Sci USA* 111, 12097-12102 (2014).
57. S. Stricker, R. Fundele, A. Vortkamp, S. Mundlos, Role of Runx Genes in Chondrocyte Differentiation. *Developmental Biology* 245, 95-108 (2002).
58. L. Koziel, M. Wuelling, S. Schneider, A. Vortkamp, Gli3 acts as a repressor downstream of Ihh in regulating two distinct steps of chondrocyte differentiation. *Development (Cambridge, England)* 132, 5249 (2005).
59. A. Ionescu et al., FoxA family members are crucial regulators of the hypertrophic chondrocyte differentiation program. *Developmental Cell* 22, 927-939 (2012).
60. H. Akiyama, M.-C. Chaboissier, J. F. Martin, A. Schedl, B. de Crombrugghe, The transcription factor Sox9 has essential roles in successive steps of the chondrocyte differentiation pathway and is required for expression of Sox5 and Sox6. *Genes & development* 16, 2813-2828 (2002).
61. C. F. Liu, W. E. Samsa, G. Zhou, V. Lefebvre, Transcriptional control of chondrocyte specification and differentiation. *Semin Cell Dev Biol* 62, 34-49 (2017).
62. D. M. Bell et al., SOX9 directly regulates the type-II collagen gene. *Nat Genet* 16, 174-178 (1997).
63. P. Dy et al., Sox9 directs hypertrophic maturation and blocks osteoblast differentiation of growth plate chondrocytes. *Dev Cell* 22, 597-609 (2012).
64. S. J. Marciniak et al., CHOP induces death by promoting protein synthesis and oxidation in the stressed endoplasmic reticulum. *Genes & development* 18, 3066-3077 (2004).
65. M. Pennuto et al., ABLATION OF THE UPR-MEDIATOR CHOP RESTORES MOTOR FUNCTION AND REDUCES DEMYELINATION IN CHARCOT MARIE TOOTH 1B MICE. *Neuron* 57, 393-405 (2008).
66. C. M. Southwood, J. Garbern, W. Jiang, A. Gow, The Unfolded Protein Response Modulates Disease Severity in Pelizaeus-Merzbacher Disease. *Neuron* 36, 585-596 (2002).
67. M. Lu et al., Opposing unfolded-protein-response signals converge on death receptor 5 to control apoptosis. *Science* 345, 98-101 (2014).
68. J. A. Moreno et al., Sustained translational repression by eIF2alpha-P mediates prion neurodegeneration. *Nature* 485, 507-511 (2012).
69. K. A. Pirog et al., Abnormal chondrocyte apoptosis in the cartilage growth plate is influenced by genetic background and deletion of CHOP in a targeted mouse model of pseudoachondroplasia. *PloS one* 9, e85145 (2014).
70. K. L. Posey et al., Chop (Ddit3) is essential for D469del-COMP retention and cell death in chondrocytes in an inducible transgenic mouse model of pseudoachondroplasia. *Am J Pathol* 180, 727-737 (2012).
71. C. Jousse et al., Inhibition of a constitutive translation initiation factor 2α phosphatase, CReP, promotes survival of stressed cells. *The Journal of Cell Biology* 163, 767-775 (2003).

72. A. L. De Sousa-Coelho, P. F. Marrero, D. Harm, Activating transcription factor 4-dependent induction of FGF21 during amino acid deprivation. *Biochem J* 443, 165-171 (2012).
73. T. L. Cameron et al., Transcriptional Profiling of Chondrodysplasia Growth Plate Cartilage Reveals Adaptive ER-Stress Networks That Allow Survival but Disrupt Hypertrophy. *PloS one* 6, e24600 (2011).
74. A. Kharitonenkov et al., FGF-21 as a novel metabolic regulator. *The Journal of Clinical Investigation* 115, 1627-1635 (2005).
75. M. A. Gomez-Samano et al., Fibroblast growth factor 21 and its novel association with oxidative stress. *Redox Biol* 11, 335-341 (2017).
76. K. H. Kim, M. S. Lee, FGF21 as a mediator of adaptive responses to stress and metabolic benefits of anti-diabetic drugs. *J Endocrinol* 226, R1-16 (2015).
77. A. Salminen, K. Kaarniranta, A. Kauppinen, Regulation of longevity by FGF21: Interaction between energy metabolism and stress responses. *Ageing Res Rev* 37, 79-93 (2017).
78. K. H. Kim et al., Autophagy deficiency leads to protection from obesity and insulin resistance by inducing Fgf21 as a mitokine. *Nat Med* 19, 83-92 (2013).
79. Y. Sekine et al., Mutations in a translation initiation factor identify the target of a memory-enhancing compound. *Science* 348, 1027 (2015).
80. C. Sidrauski et al., Pharmacological dimerization and activation of the exchange factor eIF2B antagonizes the integrated stress response. *eLife* 4, e07314 (2015).
81. G. V. Di Prisco et al., Translational control of mGluR-dependent long-term depression and object-place learning by eIF2alpha. *Nature neuroscience* 17, 1073-1082 (2014).
82. R. Savarirayan, V. Cormier-Daire, R. S. Lachman, D. L. Rimoin, Schmid type metaphyseal chondrodysplasia: a spondylometaphyseal dysplasia identical to the "Japanese" type. *Pediatric Radiology* 30, 460-463 (2000).
83. D. Samartzis et al., Classification of Schmorl's nodes of the lumbar spine and association with disc degeneration: a large-scale population-based MRI study. *Osteoarthritis and Cartilage* 24, 1753-1760.
84. H. Wang et al., Role of death receptor, mitochondrial and endoplasmic reticulum pathways in different stages of degenerative human lumbar disc. *Apoptosis* 16, 990 (2011).
85. M. Franke et al., Formation of new chromatin domains determines pathogenicity of genomic duplications. *Nature* 538, 265-269 (2016).
86. S. Cuddapah et al., Global analysis of the insulator binding protein CTCF in chromatin barrier regions reveals demarcation of active and repressive domains. *Genome Research* 19, 24-32 (2009).
87. Darfo G. Lupiáñez et al., Disruptions of Topological Chromatin Domains Cause Pathogenic Rewiring of Gene-Enhancer Interactions. *Cell* 161, 1012-1025.
88. O. Symmons et al., Functional and topological characteristics of mammalian regulatory domains. *Genome Res* 24, 390-400 (2014).
89. Y. Hotta et al., Fibroblast Growth Factor 21 Regulates Lipolysis in White Adipose Tissue But Is Not Required for Ketogenesis and Triglyceride Clearance in Liver. *Endocrinology* 150, 4625-4633 (2009).
90. H. E. Ryan, J. Lo, R. S. Johnson, HIF-1α is required for solid tumor formation and embryonic vascularization. *The EMBO Journal* 17, 3005 (1998).
91. E. Schipani et al., Hypoxia in cartilage: HIF-1α is essential for chondrocyte growth arrest and survival. *Genes & development* 15, 2865-2876 (2001).
92. J. Quackenbush, Computational analysis of microarray data. *Nature reviews. Genetics* 2, 418-427 (2001).
93. A. K. Jain, Data clustering: 50 years beyond K-means. *Pattern Recognition Letters* 31, 651-666. (2010).
94. M. Ashburner et al., Gene ontology: tool for the unification of biology. The Gene Ontology Consortium. *Nat Genet* 25, 25-29 (2000).
95. G. Dennis, Jr. et al., DAVID: Database for Annotation, Visualization, and Integrated Discovery. *Genome Biol* 4, P3 (2003).
96. S. Heinz et al., Simple combinations of lineage-determining transcription factors prime cis-regulatory elements required for macrophage and B cell identities. *Molecular cell* 38, 576-589 (2010).
97. E. Wingender, P. Dietze, H. Karas, R. Knuppel, TRANSFAC: a database on transcription factors and their DNA binding sites. *Nucleic Acids Res* 24, 238-241 (1996).
98. P. J. Balwierz et al., ISMARA: automated modeling of genomic signals as a democracy of regulatory motifs. *Genome Res* 24, 869-884 (2014).
99. B. Langmead, C. Trapnell, M. Pop, S. L. Salzberg, Ultrafast and memory-efficient alignment of short DNA sequences to the human genome. *Genome Biology* 10, R25-R25 (2009).
100. V. Y. L. Leung, W. C. W. Chan, S.-C. Hung, K. M. C. Cheung, D. Chan, Matrix Remodeling During Intervertebral Disc Growth and Degeneration Detected by Multichromatic FAST Staining. *Journal of Histochemistry and Cytochemistry* 57, 249-256 (2009).
101. A. W. K. Wai et al., Disrupted expression of matrix genes in the growth plate of the mouse cartilage matrix deficiency (cmd) mutant. *Developmental Genetics* 22, 349-358 (1998).
102. L.-J. Ng et al., SOX9 Binds DNA, Activates Transcription, and Coexpresses with Type II Collagen during Chondrogenesis in the Mouse. *Developmental Biology* 183, 108-121 (1997).
103. C. Sidrauski et al., Pharmacological brake-release of mRNA translation enhances cognitive memory. *Elife* 2, e00498 (2013).
104. G. V. Di Prisco et al., Translational control of mGluR-dependent long-term depression and object-place learning by eIF2[alpha]. *Nature neuroscience* 17, 1073-1082 (2014).
105. H. Zeng et al., An inducible and reversible mouse genetic rescue system. *PLoS Genetics* 4(5):e1000069. doi: 10.1371/journal.pgen.1000069 (2008).
106. W. C. W. Chan et al., Activating the unfolded protein response in osteocytes causes hyperostosis consistent with craniodiaphyseal dysplasia. *Human Molecular Genetics* doi: 10.1093/hmg/ddx339 (2017).

What is claimed is:

1. A method for the amelioration and/or treatment of a disease caused by the activation of the integrated stress response (ISR) involving the p-eIF2α pathway in a subject, comprising: administering to the subject a modulator of a phosphorylated eukaryotic initiation factor 2α (p-eIF2α), wherein the modulator is represented by Formula I:

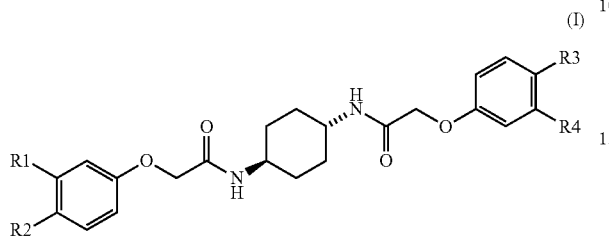

(I)

wherein each of R1, R2, R3 and R4 is independently selected from a group consisting of hydrogen, halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —CCH, —CH₂CCH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHOH, —OCF₃, —OCHF₂, —N₃, substituted or substituted or alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

2. The method of claim 1, wherein an effective amount of the modulator is capable of one or more of the following:
a) inhibiting the phosphorylation of eIF2α;
b) promoting the de-phosphorylation of eIF2α;
c) inhibiting the effect of phosphorylated-eIF2α;
d) inhibiting the transcription or expression of Sox9/SOX9;
e) inhibiting the transcription or expression, by translation control, of ATF4; and
promoting the assembly of GADD34-Pp1c.

3. The method of claim 1, wherein the modulator is selected from the following:

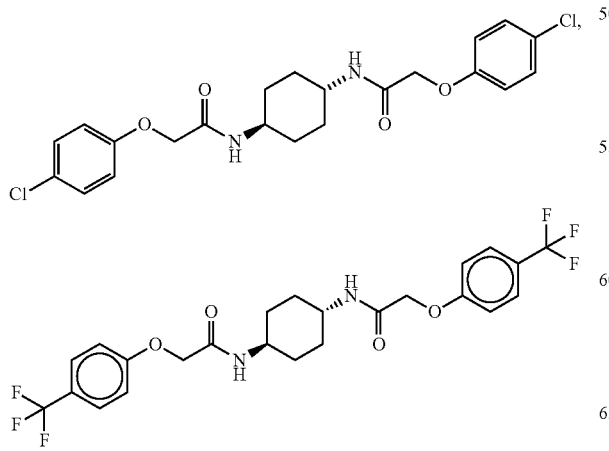

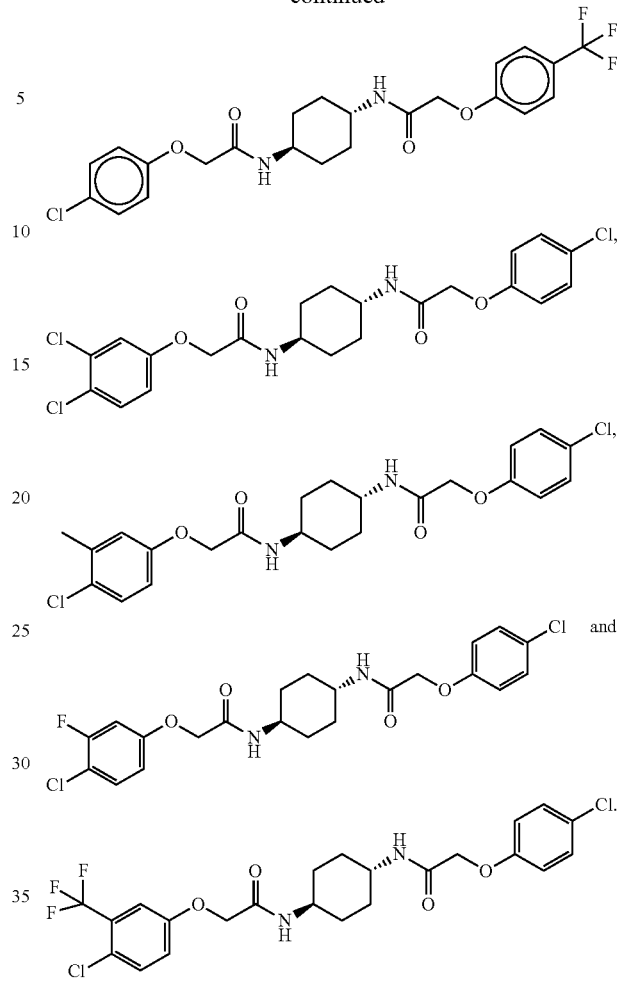

4. The method of claim 1, wherein the effective amount of the modulator is 0.1 mg/kg to 50 mg/kg per day.

5. A method of treating intervertebral disc degeneration (IDD), comprising a step of contacting a population of nucleus pulposus (NP) cells in an intervertebral disc with an effective amount of a molecule represented by Formula I:

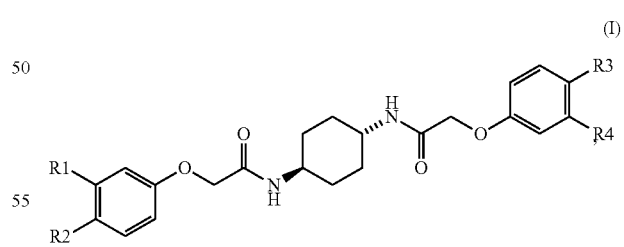

(I)

wherein each of R1, R2, R3 and R4 is independently selected from a group consisting of hydrogen, halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —CCH, —CH₂CCH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHOH, —OCF₃, —OCHF₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

6. The method of claim 5, wherein each of R1, R2, R3 and R4 is independently selected from a group consisting of hydrogen, halogen, —OCH$_3$, —OCH$_2$Ph, —C(O)Ph, —CH$_3$, —CF$_3$, —CCl$_3$, —CN, —COOH, —CONH$_2$, —NO$_2$, —C(O)CH$_3$, —CH(CH$_3$)$_2$, —CCH, —CH$_2$CCH, —SH, —SO$_2$NH$_2$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

7. The method of claim 5, wherein each of R1, R2, R3 and R4 is independently selected from a group consisting of hydrogen, halogen, —OCH$_3$, —OCH$_2$Ph, —C(O)Ph, —CH$_3$, —CF$_3$, —CCl$_3$, —CN, —COOH, —CONH$_2$, —NO$_2$, —C(O)CH$_3$, —CH(CH$_3$)$_2$, —CCH, —CH$_2$CCH, —SH, —SO$_2$NH$_2$, —OCF$_3$, —OCHF$_2$, substituted or unsubstituted alkyl, substituted or unsubstituted heteroalkyl, substituted or unsubstituted cycloalkyl, and substituted or unsubstituted heterocycloalkyl.

* * * * *

SEQUENCE LISTING

<160> NUMBER OF SEQ ID NOS: 41

<210> SEQ ID NO 1
<211> LENGTH: 8

```
<212> TYPE: DNA
<213> ORGANISM: Mus musculus
<220> FEATURE:
<223> OTHER INFORMATION: ATF4 binding site on murine Sox9 locus

<400> SEQUENCE: 1 tgttgcaa                                                                 8

<210> SEQ ID NO 2
<211> LENGTH: 148
<212> TYPE: DNA
<213> ORGANISM: Mus musculus
<220> FEATURE:
<223> OTHER INFORMATION: Binding sites for ATF4 as reported in Han

<400> SEQUENCE: 2
gtcacccaaa catttgcttc caaaagacca tttctaagca cttttttttgg aagccggcag        60 actccaggcg cagaagccca gctccgcttt gacgagcagc tgttgcaatt tccattgctg       120
taaacgccag cgaagtcccg ggtaccac                                          148

<210> SEQ ID NO 3
<211> LENGTH: 8
<212> TYPE: DNA
<213> ORGANISM: Homo sapiens
<220> FEATURE:
<223> OTHER INFORMATION: ATF4 binding site

<400> SEQUENCE: 3 tgttgcaa                                                                 8

<210> SEQ ID NO 4
<211> LENGTH: 8
<212> TYPE: DNA
<213> ORGANISM: Mus musculus
<220> FEATURE:
<223> OTHER INFORMATION: Amino Acid Response Element (AARE) sequence

<400> SEQUENCE: 4 ttgcatca                                                                 8

<210> SEQ ID NO 5
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 5
gagttgccac agcttccctg gtggtagcac agatgttgtc tggcagacag agacagaggc        60
ttacaggaca gtctcaagaa cgaccagagt caacctgaac a                           101

<210> SEQ ID NO 6
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 6 tacccccaa aaatataaaa taaatccct tagtctaaaa ttccatgcaa ttaacattgt          60
ttacttaagg aggaagctct ccaggacaat gttcacatct a                           101

<210> SEQ ID NO 7
```

```
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 7
cagttctttc aggaagaaaa acaaacattc cactcaaagt taaaactgaa ttgtttccca     60
tttgaacaaa ttatgacttt tgatatataa tagagaagac t                       101

<210> SEQ ID NO 8
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 8
ggaagtgggg gtggtgacaa aggaggtggt aagggagggg aaattgtgat caggatgtaa     60
cataggcgag aataaattca taatgttaac taacaaaaaa a                       101

<210> SEQ ID NO 9
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 9
catccagaag gacaatgtca acatctagcc tcagcatgtg gtcactgaga cttcccacaa     60
ggatttgata ttttttaacat taccaaagca cggtacacaa c                      101

<210> SEQ ID NO 10
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 10
ttcaaccttg tacaactcca gactcggtga ctctagacac agtaggagag aaggaaacta     60
aagaagagtg tgggaagctt acatgctcac attctgaccc a                       101

<210> SEQ ID NO 11
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 11
acagccattt cctccttagc tgcctcctac aaaacatcac accctggcct ccatcctcag     60
cccagtgcca ggcccatcat tggggaagac accgcacttc c                       101

<210> SEQ ID NO 12
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 12
agtgacagag agtgtcagga tgtgatgggg cctccagtga ccacctcgct cacccgggaa     60
```

```
ctttccaaat gtcacacata aaccctctca ctaattagct g                          101
```

<210> SEQ ID NO 13
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 13

```
gaagaatgca ggcaagaaac ataggagaga agcactcctg aatggagcct tcccgctcag     60
agagcaattg ttgctgctca ctcttttgga gctcaacaaa c                         101
```

<210> SEQ ID NO 14
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 14

```
attaaataaa gttgtaatga tggcgttttg atccaacagg cctctttttt tttaaatatt     60
tttattatta tgtattttcc tcaattacat ttagaatgct a                         101
```

<210> SEQ ID NO 15
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 15

```
cctgagagct tttcagactc aattatccct aaagccataa tgagaactgc atcatggaaa     60
ggagacttgg accctatgac atgcagtaac aaagagtctg c                         101
```

<210> SEQ ID NO 16
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 16

```
cctttgcaga tgaagtaata cacaatcctg gaaggtgcac taaaaatcct aggaagaaga     60
cagagtgatt cagcctgaat attgagaaga gaatccaggg a                         101
```

<210> SEQ ID NO 17
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 17

```
aagagagacg aggtgcaagt ggccccggtt tcgttctctg ttttccctcc ctcctcctcc     60
gctccgactc gccttccccg ggtttagagc cggcagctga g                         101
```

<210> SEQ ID NO 18
<211> LENGTH: 101
<212> TYPE: DNA
<213> ORGANISM: Mus musculus
<220> FEATURE:

<223> OTHER INFORMATION: Sequence from murine Chromosome 11

<400> SEQUENCE: 18
gtccttcttt cttattatgg ctgagggctc cagcccatct ctacttagaa ccacatccag    60
cgcatctctc attccactcc tccctgttc tctcagtctc c                         101

<210> SEQ ID NO 19
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 19
tacacacaaa catatacata catacacata catctttaca cacatatgta caaacacaca    60
ccaaacacat ccaccacaat aaatatttta agttgaaaag t                        101

<210> SEQ ID NO 20
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 20
gggttttcta taagagcact gcatgcttta aaccagagag tcctctttct gtttcttctt    60
tcgttttcta agaatgaatc tcatgtaccc caggctgact t                        101

<210> SEQ ID NO 21
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 21
gtaattcttt gactcttgac ttcttgggat agcatgcttg ataatgatca aagcagcaaa    60
cagacctggt taggaaaatg gccgttctcc cttccactgc t                        101

<210> SEQ ID NO 22
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 22
ctcacatggt gttccccggt aggaggaatg gcatggctgc ctctacataa atgcaggggg    60
gttgggaggg tgcaagggca tctcctgaag gaggacctgc t                        101

<210> SEQ ID NO 23
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 23
tcccaaagga tgggattata ggtctatgcc accacatgcc ccctgggcgc tgattttga     60 tccctgccac tgatccagta ggacactgag gtgcagtagc a                        101

```
<210> SEQ ID NO 24
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 24
gcttctactc agttgcaata agacctttag gctgatttta atagagggca atacaaataa    60
agtcgcaatt aatattccta ttcagtttct taaaagaaat a                       101

<210> SEQ ID NO 25
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 25
tctcagctcc tcctgcgcca tgcctgcctg gatactgcca tgctcccacc ttgatgataa    60
tggactgaac ctctgaatct gtaagccagc cccaattaaa t                       101

<210> SEQ ID NO 26
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 26
aaaaaaaaat agagagagag gtgcctgtgc gccatttaca acacatttaa gtaaatcaat    60
aggaaaaaaa tagcagaaat aattagaatt gcctgtcctt g                       101

<210> SEQ ID NO 27
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 27
tcagtgctct tacccgctga gccatctcgc cagccctcaa cattttttaaa attatgccca   60 acttggagct ggagagatgg ctcaacagtt aagagcactg g                       101

<210> SEQ ID NO 28
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 28
tgggtggctt gtgtgaagcc tgccctgagc cttttaaaaa ttatactttg tattcatttc    60
tttgtgtacg tgtgcacgtg tgtgaggtca gaggacaagt c                       101

<210> SEQ ID NO 29
<211> LENGTH: 101
<212> TYPE: DNA
<213> ORGANISM: Mus musculus
<220> FEATURE:
<223> OTHER INFORMATION: Sequence from murine Chromosome 11

<400> SEQUENCE: 29
```

```
tacttttgtg tgtgtgtgtg tgcgtgtaca tgtgtgcaca tgcatgctca cttaattgac      60
tttcattatg cttgtgaggg gttgtttatc agctcattga t                         101
```

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30

```
cagatcagtg atgggctatg                                                  20
```

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31

```
gaaccacctg gagaaggcag att                                              23
```

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32

```
gaggtggcca agcacttgaa a                                                21
```

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33

```
gaaccacctg gagaaggcag att                                              23
```

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34

```
gcttccccag tggagccaat                                                  20
```

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35

```
ccacctctgc ttagctctgc aat                                              23
```

<210> SEQ ID NO 36
<211> LENGTH: 25

-continued

```
<212> TYPE: DNA
<213> ORGANISM: Artificial Sequence
<220> FEATURE:
<223> OTHER INFORMATION: Primer

<400> SEQUENCE: 36
atgaggatct gcaggaggtc ctgtc                                       25

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
gatgcccact gttcatgctt ggt                                         23

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aagactacaa aagcttcttg                                             20

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
aagaattctc atcgaagtgc aa                                          22

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40 cagggggtcat tcaaatcctg                                            20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
aggaatcctg cttggtcttg                                             20
```